United States Patent
Gravett et al.

(10) Patent No.: US 7,829,118 B1
(45) Date of Patent: Nov. 9, 2010

(54) MODIFIED HYALURONIC ACID POLYMER COMPOSITIONS AND RELATED METHODS

(75) Inventors: David M. Gravett, Mountain View, CA (US); George Y. Daniloff, Los Altos, CA (US); Pingren He, Sunnyvale, CA (US)

(73) Assignee: Carbylan Biosurgery, Inc., Palo Alto, CA (US)

( * ) Notice: Subject to any disclaimer, the term of this patent is extended or adjusted under 35 U.S.C. 154(b) by 0 days.

(21) Appl. No.: 12/842,762

(22) Filed: Jul. 23, 2010

Related U.S. Application Data

(60) Provisional application No. 61/230,074, filed on Jul. 30, 2009, provisional application No. 61/311,953, filed on Mar. 9, 2010.

(51) Int. Cl.
*A61K 9/14* (2006.01)
*C07H 5/02* (2006.01)

(52) U.S. Cl. ........................ 424/488; 536/122

(58) Field of Classification Search ........... None
See application file for complete search history.

(56) References Cited

U.S. PATENT DOCUMENTS

| 6,096,728 A | 8/2000 | Collins et al. |
| 7,034,127 B2 | 4/2006 | Parent et al. |
| 2006/0110458 A1 | 5/2006 | Hahn et al. |
| 2007/0134334 A1 | 6/2007 | Hahn et al. |
| 2008/0031854 A1 | 2/2008 | Prestwich et al. |
| 2009/0148534 A1 | 6/2009 | Yasugi et al. |
| 2009/0226519 A1 | 9/2009 | Claude et al. |

FOREIGN PATENT DOCUMENTS

EP  2103631 A1  9/2009

*Primary Examiner*—Robert A Wax
*Assistant Examiner*—Jeffrey T Palenik
(74) *Attorney, Agent, or Firm*—Susan T. Evans; King & Spalding LLP

(57) ABSTRACT

The present application provides compositions comprising hyaluronic acid having low levels of functional group modification, mixtures formed by controlled reaction of such lightly modified hyaluronic acid with suitable difunctional or multi-functional crosslinkers, and hydrogel precursor compositions and the resulting hydrogels. The compositions are lightly cross-linked and possess low pro-inflammatory properties when injected in vivo, and can be used as, for example, medical devices, biomedical adhesives and sealants, and for localized delivery of bioactive agents, among other uses.

20 Claims, 14 Drawing Sheets

Group 1 HA-VS Gel Animal 3171

Group 1 0.9% NaCl Animal 3171

Group 2 HA-VS/TA Gel Animal 3174

Group 2 0.9% NaCl Animal 3174

Group 3 TA 2mg/ml Animal 3833

Group 3 0.9% NaCl Animal 3833

Group 4 TA 8mg/ml Animal 3589

Group 4 0.9% NaCl Animal 3589

Group 5 HA-VS Gel Animal 3595

Group 5 0.9% NaCl Animal 3595

Group 6 HA-VS/TA Gel Animal 3173

Group 6 0.9% NaCl Animal 3173

Group 7 TA 2mg/ml Animal 3594

Group 7 0.9% NaCl Animal 3594

Group 8 TA 8mg/ml Animal 3162

Group 8 0.9% NaCl Animal 3162

MODIFIED HYALURONIC ACID POLYMER COMPOSITIONS AND RELATED METHODS

CROSS-REFERENCE TO RELATED APPLICATIONS

This application claims the benefit of priority to U.S. Provisional Application No. 61/230,074, filed Jul. 30, 2009 and to U.S. Provisional Application No. 61/311,953, filed Mar. 9, 2010, the contents each of which is incorporated herein by reference in its entirety.

FIELD

The disclosure relates generally to hyaluronic acid having low levels of functional group modification, mixtures formed by controlled reaction of such lightly modified hyaluronic acid with suitable difunctional or multi-functional reactants, and related hydrogel and hydrogel precursor compositions. The compositions described herein are lightly cross-linked and possess low pro-inflammatory properties when injected in vivo, and can be used as, for example, medical devices, biomedical adhesives and sealants, and for localized delivery of bioactive agents, among other uses.

BACKGROUND

Hyaluronic acid is a naturally-occurring, anionic, non-sulfated glycosaminoglycan that is distributed widely throughout connective, epithelial, and neural tissues. The average 70 kg (154 lbs) person possesses roughly 15 grams of hyaluronic acid in his/her body, one-third of which is turned over (degraded and synthesised) every day (Stern R. *Eur J Cell Biol* 83 (7): 317-25, (2004)). Since hyaluronic acid is found naturally in many tissues of the body and is therefore biocompatible, it is believed to be well suited to biomedical applications. Indeed, many polymeric materials, including hyaluronic acid (also referred to as hyaluronan), derivatized forms thereof, and its conjugates, can be used as injectable biomaterials, as well as in medical devices and implantable materials. Applications include delivery of therapeutic molecules to a localized site, use as adhesives or sealants, in tissue engineering, as viscosupplements, and in wound healing. Hyaluronic acid, when administered and used as a therapeutic in its naturally occurring form, is typically rapidly cleared from the body, making frequent administration necessary. Although often a polymeric gel or gel precursor may demonstrate favorable properties in terms of reaction chemistry and conditions, gellation characteristics, and/or therapeutic effect in one or more in-vitro models, in certain instances, such effects fail to translate into beneficial properties in vivo or in a clinical setting.

SUMMARY

In a first aspect, provided is a hyaluronic acid modified to a degree of 10% or less by reaction with divinyl sulfone. Specifically, the hyaluronic acid possesses 10% or less of its hydroxyl groups derivatized by an addition reaction with divinyl sulfone.

In a particular embodiment, the hyaluronic acid has 1-10% of its hydroxyl groups derivatized to 2-(vinylsulfonyl)ethoxy groups. The resulting activated hyaluronic acid, having a low level of divinyl sulfone activation is referred to generally herein as (2-(vinylsulfonyl)ethoxy)$_{1-10\%}$hyaluronic acid or "VS-HA".

In yet another embodiment, the hyaluronic acid has a degree of conversion of hydroxyl groups to 2-(vinylsulfonyl)ethoxy groups selected from 1%, 2%, 3%, 4%, 5%, 6%, 7%, 8%, 9%, and 10%.

In yet a more specific embodiment, the hyaluronic acid has a degree of conversion of hydroxyl groups to 2-(vinylsulfonyl)ethoxy groups of about 4-5% per disaccharide repeat unit.

In yet another embodiment, the (2-(vinylsulfonyl)ethoxy)$_{1-10\%}$ hyaluronic acid possesses a molecular weight ranging from about 700 to about 3 million Daltons.

In a second aspect, provided is a hydrogel formed by reaction of (2-(vinylsulfonyl)ethoxy)$_{1-10\%}$hyaluronic acid with a thiol crosslinker having two or more thiol groups.

In a related embodiment, the thiol crosslinker possesses from two to about 8 thiol groups. In yet another embodiment, the thiol crosslinker possesses a number of thiol groups selected from 2, 3, 4, 5, 6, 7, and 8.

In yet another embodiment directed to the second aspect, the thiol crosslinker is a thiol-functionalized polyethylene glycol (PEG) (i.e., a PEG-thiol).

In an additional embodiment of the foregoing, the polyethylene glycol thiol possesses a molecular weight ranging from about 250 about 20,000 daltons.

In a related embodiment, the thiol-functionalized polyethylene glycol is linear and possesses a thiol group at each terminus, i.e., is polyethylene glycol dithiol (PEG dithiol).

In yet another embodiment, the thiol-functionalized polyethylene glycol is four-armed and possesses a pentaerythritol core.

In yet another embodiment, the thiol-functionalized polyethylene glycol possesses a polyol core selected from glycerol, glycerol dimer (3,3'-oxydipropane-1,2-diol) trimethylolpropane, sorbitol, pentaerythritol, and hexaglycerol.

In a further embodiment, the hydrogel formed by reaction of (2-(vinylsulfonyl)ethoxy)$_{1-10\%}$hyaluronic acid with a thiol crosslinker contains less than ten percent of unreacted thiol and less than 10% of unreacted vinyl sulfone groups. The quantity of residual, unreacted thiol groups can be determined, for example, using the Ellman's test.

In yet an additional embodiment, a hydrogel formed by reaction of (2-(vinylsulfonyl)ethoxy)$_{1-10\%}$hyaluronic acid with a thiol crosslinker contains a percent by weight (wt/wt) of polymer to water ranging from about 0.5 to 5.0 percent. Illustrative percents by weight of polymer to water for the resulting hydrogel are, in one or more embodiments, selected from 0.5, 1.0, 1.5, 2.0, 2.5, 3.0, 3.5, 4.0, 4.5 and 5 percent.

In yet another embodiment, the hydrogel formed by reaction of (2-(vinylsulfonyl)ethoxy)$_{1-10\%}$hyaluronic acid with a thiol crosslinker is in the form of particles having a size ranging from about 0.10 to 3.0 millimeters.

In yet another embodiment, the foregoing hydrogel particles are in the form of an aqueous slurry.

In yet a further embodiment, the hydrogel as described in any one or more of the foregoing embodiments is dispersed in an aqueous solution of unmodified hyaluronic acid.

In yet an additional and more specific embodiment, provided is a composition comprising crosslinked hydrogel particles in a solution of hyaluronic acid in saline, where the hydrogel particles are formed by reaction of polyethylene glycol dithiol (PEG-dithiol) with hyaluronic acid having 1-10% of its hydroxyl groups derivatized with 2-(vinylsulfonyl)ethoxy groups.

In yet an additional embodiment, the hydrogel as described in any one or more of the foregoing embodiments comprises a bioactive agent. In a specific embodiment, the bioactive agent is a corticosteroid. In yet a more particular embodiment, the bioactive agent is triamcinolone acetonide.

In yet an alternative embodiment, the hydrogel as described in any one or more of the foregoing embodiments comprises living cells.

In a further embodiment, the hydrogel formed by reaction of (2-(vinylsulfonyl)ethoxy)$_{1-10\%}$hyaluronic acid with a bifunctional or greater thiol crosslinker exhibits low pro-inflammatory properties in a goat joint injection model.

In a particular embodiment, the hydrogel exhibits low pro-inflammatory properties as indicated by leukocyte response in associated synovial fluid.

In yet another particular embodiment, the hydrogel exhibits low pro-inflammatory properties in a goat joint injection model as indicated by gross observational scoring.

In yet an additional embodiment, the hydrogel is sterile.

In yet a further embodiment, a hydrogel as provided herein is packaged in a syringe.

In yet a further embodiment, provided is a method of administering any of the herein described hydrogel compositions into an intra-articular space of a joint of a subject.

In yet a third aspect, provided is a method of preparing (2-(vinylsulfonyl)ethoxy)$_{1-10\%}$ hyaluronic acid. The method comprises reacting hyaluronic acid with divinyl sulfone under reaction conditions effective to react no more than about 10% of hydroxyl groups on the hyaluronic acid disaccharide repeat units with the divinyl sulfone to form (2-(vinylsulfonyl)ethoxy)$_{1-10\%}$hyaluronic acid.

In a related embodiment, the reacting comprises reacting hyaluronic acid with a molar excess of divinyl sulfone.

In a further embodiment, the reacting step is carried out under ambient conditions.

In yet another embodiment, the reacting step is carried out for 10 seconds to about 120 seconds under ambient conditions.

In yet another embodiment, the reacting step is carried out in aqueous base.

In a further embodiment, the method further comprises quenching the reaction by addition of acid. In a related embodiment, sufficient acid is added to adjust the pH to a range from about 4 to 6.5.

In a fourth aspect, described herein is a method of preparing a hydrogel. The method comprises reacting (2-(vinylsulfonyl)ethoxy)$_{1-10\%}$hyaluronic acid with a thiol crosslinker having two or more thiol groups under reaction conditions effective to form a crosslinked hydrogel. Suitable thiol crosslinking agents include thiol-functionalized polyethylene glycol, alkane-dithiols and the like.

In a related embodiment, the reacting is carried out at physiological pH.

In yet another embodiment, the reacting is carried out in the absence of a polymerization initiator.

In yet another embodiment, the reacting is carried out in the absence of application of an external energy source.

In yet another embodiment, the reacting is carried out at a temperature ranging from 20° C. to 45° C.

In yet a further embodiment, the hydrogel comprises 10% or less of unreacted vinyl sulfone or thiol groups. Preferably, the hydrogel comprises 5% or less of unreacted sulfone or thiol groups. In a specific embodiment, the hydrogel comprises essentially no detectable unreacted vinyl sulfone or thiol groups.

In a fifth aspect, provided is a kit comprising syringe, where the syringe comprises a hydrogel formed by reaction of (2-(vinylsulfonyl)ethoxy)$_{1-10\%}$hyaluronic acid with a thiol crosslinker as described above.

In yet another related embodiment, the syringe comprises a hydrogel as described in any one or more of the above embodiments where the hydrogel is dispersed in an aqueous solution of unmodified hyaluronic acid. In a related embodiment, the aqueous solution is saline.

In a related embodiment, the syringe is in a form suitable for intra-articular injection of the hydrogel using a 18-21 gauge needle.

In yet another related embodiment, the syringe comprises a hydrogel as described in any one or more of the above embodiments where the hydrogel further comprises a bioactive agent. In a related embodiment, the bioactive agent is selected from the group consisting of steroids, growth factors, anti-proliferative agents, and antibiotics. In yet a more specific embodiment, the hydrogel comprises from about 0.01% to about 20% by weight bioactive agent, depending of course on the potency of the bioactive agent. That is to say, a less potent agent will typically be contained in the hydrogel at the higher end of the foregoing range, e.g., from about 10-20% by weight, while a potent bioactive agent will be at the lower end of the range, e.g., from about 0.01 to 3% by weight. In a specific embodiment in which the bioactive agent is triamcinolone acetonide, the hydrogel comprises from about 0.1 to 1% by weight bioactive agent.

In yet another embodiment, the syringe comprises a hydrogel as described in any one or more of the above embodiments where the hydrogel further comprises living cells. Exemplary living cells include stem cells, parenchimal stem cells, blood-derived cells, and bone marrow cells.

In a sixth aspect, provided is a method for delivering a poorly water soluble bioactive agent by administering a hydrogel as described herein comprising the poorly water soluble bioactive agent dispersed in the hydrogel.

In a seventh aspect, described is a method of treating acute and chronic inflammation associated with osteoarthritis, rheumatoid arthritis, other inflammatory arthritides, and repetitive use by injecting a hydrogel in accordance with any one or more aspects or embodiments described herein into the intra-articular space of a joint such as the knee in a subject. In a particular embodiment, i.e., when the hydrogel comprises a corticosteroid incorporated therein, the method is effective to result in damage to the cartilage that is reduced from the cartilage damage that occurs upon administration of an equivalent amount of the corticosteroid absent hydrogel entrapment, as characterized in a goat joint injection model by total Mankin score at 28 days post injection. In a related embodiment, the foregoing method, i.e., injection of the hydrogel into the intra-articular space of a joint, is effective to provide to the subject a degree of pain relief relative to the pain experienced by the subject prior to injection of the subject hydrogel. Typically, initiation of pain relief is experienced by the subject within anywhere from about one hour to about one week following the injection, more preferably within about one hour to about 3 days following injection. That is to say, initiation of pain relief typically commences within about 1, 2, 3, 4, 5, 6, 7, 8, 9, 10, 11, 12, 13, 14, 15, 16, 17, 18, 19, 20, 21, 22, 23, or 24 hours post injection, or, if not within the first twenty four hours, within 1, 2, 3, 4, 5, 6, or 7 days post-injection. Typically, the duration of pain relief is expected to last anywhere from about 3 to 9 months, i.e., from 3, 4, 5, 6, 7, 8, 9 months or even longer.

In an eighth aspect, provided is a method for reducing damage to cartilage upon administration of a corticosteroid into the intra-articular space of a joint of a subject suffering from osteoarthritis by incorporating the corticosteroid into a cross-linked hydrogel prior to or upon administration to the subject. The cross-linked hydrogel is generally a hyaluronic acid-based hydrogel to be described in greater detail below. An exemplary cross-linked hydrogel is one that is a hyaluronic acid modified to a degree of 10% or less by reaction with divinyl sulfone, followed by cross-linking with a thiol crosslinker having two or more thiol groups. Surprisingly, by virtue of incorporating the corticosteroid into the cross-linked hydrogel, less damage occurs to the cartilage than occurs upon administration of an equivalent dose of corticosteroid absent hydrogel incorporation.

In a ninth aspect related to the foregoing, in a method for treating osteoarthritis by administering a therapeutically effective amount of a corticosteroid into the intra-articular space of a joint of a subject, provided herein is an improvement comprising administering the corticosteroid in the form of a cross-linked hydrogel composition comprising the corticosteroid, whereby damage to the cartilage is lessened when compared to administration of an equivalent amount of the corticosteroid absent hydrogel incorporation.

In a particular embodiment related to the seventh, eighth and ninth aspects, the corticosteroid is selected from the group consisting of hydrocortisone, hydrocortisone acetate, cortisone acetate, tixocortol pivalate, prednisolone, methylprednisolone, prednisone, triamcinolone, triamcinolone salts such as triamcinolone acetonide, triamcinolone benetonide, triamcinolone furetonide, triamcinolone hexacetonide, triamcinolone diacetate, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, beclomethasone dipropionate monohydrate, flunisolide, fluticasone propionate, mometasone furoate monohydrate, and fluticasone furoate.

In an even more specific embodiment, the corticosteroid is triamcinolone acetonide.

In a tenth aspect, provided is a formulation comprising a poorly water-soluble soluble drug such as a steroid entrapped within the 3-dimensional structure of a hydrogel as described herein, followed by injecting such formulation into the intra-articular space of a joint.

In one embodiment related to the foregoing, the trapping of steroid particles within the hydrogel is effective to prevent direct contact of the majority of the steroid particles with the joint tissues.

In yet another related embodiment, the trapping of steroid particles in the hydrogel is effective to maximize the localized concentration of the steroid in the joint, while minimizing its systemic concentration.

In yet a further embodiment, the entrapment of steroid particles in the hydrogel is effective to protect the steroid particles from premature clearance from the joint.

In yet an additional embodiment, by entrapping the steroid in the hydrogel, therapeutic efficacy of the steroid is attained at a lower total dose than would be attained absent hydrogel entrapment, while minimizing unwanted local and systemic side effects.

In a related aspect, provided is the use of a hydrogel as described herein for injecting or implanting onto or into bone, teeth, nerves, cartilage, blood vessels, soft tissues or other tissues of a mammalian subject.

Additional embodiments of the compositions, methods, kits, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description, particularly when considered in conjunction with the accompanying examples and drawings.

DETAILED DESCRIPTION

Figure 1:
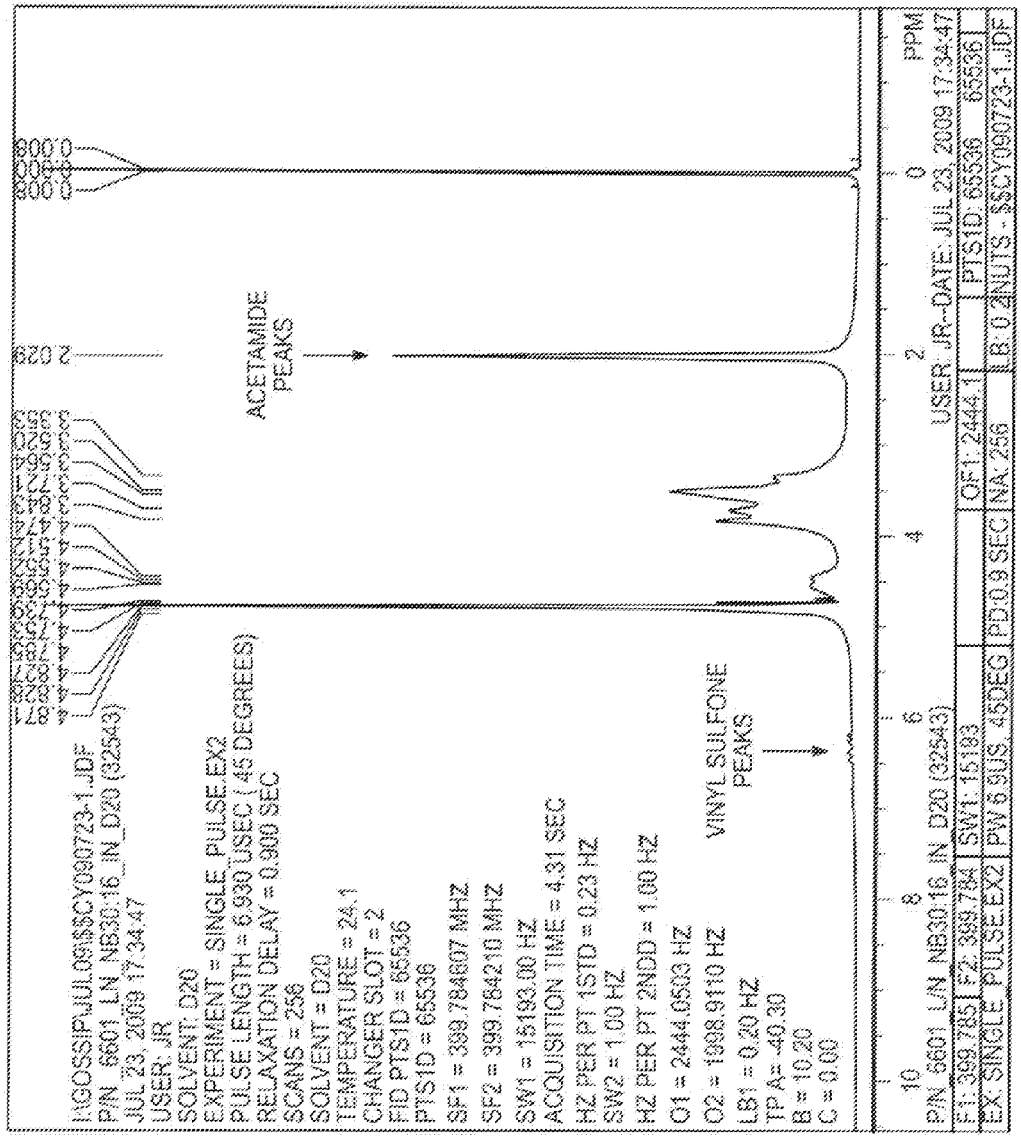
FIG. 1 is a $^1$H NMR spectrum of vinyl-sulfone modified hyaluronic acid (HA-VS) prepared as described in Example 1. Based upon the NMR, the hyaluronic acid was determined to possess a level of vinyl sulfone substitution of approximately four percent per disaccharide.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

DEFINITIONS

It must be noted that, as used in this specification, the singular forms "a," "an," and "the" include plural referents unless the context clearly dictates otherwise. Thus, for example, reference to a "polymer" includes a single polymer as well as two or more of the same or different polymers.

Unless specifically noted otherwise, definitions of the terms herein are standard definitions used in the arts of organic synthesis, and polymer and pharmaceutical science.

In describing and claiming the present invention, the following terminology will be used in accordance with the definitions described below.

A "biocompatible polymer" is a polymer having degradation products that are compatible with living tissue, or that may have beneficial biological properties. The biocompatible polymer may be biocompatible in itself, and/or may be synergistically biocompatible when employed in conjunction with a biologically active agent.

The term "hyaluronic acid polymer" refers to a polymer comprising repeat disaccharide subunits of hyaluronan, where the repeat units may be derivatized at one or more positions of the D-glucuronic acid and/or the D-N-acetylglucosamine unit of the disaccharide repeat subunit. A hyaluronic acid polymer is meant to encompass hyaluronic acid (also referred to as hyaluronan), derivatized hyaluronic acid, salts forms, hyaluronic acid linker complexes, and hyaluronic acid conjugates. The term, "hyaluronic acid", is meant to refer to unmodified or non-derivatized hyaluronic acid.

The terms "hyaluronic acid derivative" or "derivatized hyaluronic acid" or "modified hyaluronic acid" refers to hyaluronic acid that has been derivatized by reaction with, e.g., one or more small chemical moieties such as divinyl sulfone or the like.

A thiol-derivatized hyaluronic acid polymer refers to a hyaluronic acid polymer as described above having three or more disaccharide repeat units and comprising at least one sulfhydryl (thiol) group.

The term "reactive" refers to a functional group (e.g., present in a polymer) that reacts readily or at a practical rate under conventional conditions of organic synthesis. This is in contrast to those groups that either do not react or require strong catalysts or impractical reaction conditions in order to react (i.e., a "nonreactive" or "inert" group).

"Molecular mass" or molecular weight, as used herein, in the context of a water-soluble polymer such as hyaluronic acid, refers to the nominal average molecular mass of a polymer determined by multi angle light scattering. Molecular weight can be expressed as either a number-average molecular weight or a weight-average molecular weight. Unless otherwise indicated, all references to molecular weight herein refer to the number-average molecular weight.

The term "hydrogel" refers to a water-containing three dimensional hydrophilic polymer network or gel in which the water is the continuous phase and in which the water content is greater than 50% (w/w). The hydrogels described herein typically do not require the incorporation of cross-linking initiators or accelerants to achieve the desired degree of crosslinking.

A "sterile" composition is one that is free of viable microbes as determined using the USP sterility test. See "The United States Pharmacopeia", 30th Revision, The United States Pharmacopeial Convention: 2008.

The term "lightly crosslinked" as used herein or "having a low degree of crosslinking" means that the crosslinking reaction occurs such that about 40% to about 100% of the available crosslinking sites are reacted to generate the final crosslinked gels, where the modified hyaluronic acid starting material used to form the gel possesses 10% or less of its hydroxyl groups in activated/derivatized form, to thereby provide an hydrogel that is considered overall to be lightly crosslinked.

A hydrogel that exhibits low pro-inflammatory properties in a goat joint injection model is one that when evaluated in a goat joint injection model as described herein exhibits a synovial fluid leukocyte count of less than 20,000 cells per cubic millimeter at 24 hours post-injection, and preferably, a synovial fluid leukocyte count of less than 15,000 cells per cubic millimeter at 24 hours post-injection, where the count is an average count taken from three individual injected animals.

A hydrogel containing a corticosteroid that "reduces damage to the cartilage" or "that produces less cartilage damage" than an equivalent dose of a corticosteroid administered absent incorporation into the subject hydrogel is typically characterized by any suitable model for assessing cartilage damage, but preferably, is measured using an in-vivo goat knee injection model as described in detail herein. Post injection data is typically collected at least 7 days but no more than 28 days post injection. A preferred standard of measure is total Mankin score; a material that reduces damage to cartilage over drug alone, assessed as described previously, is one that demonstrates an improvement in the average score over the drug (i.e., corticosteroid), when administered in an equivalent amount. Preferably, the total Mankin score for hydrogel-incorporated drug is improved by at least one or more points over the total Mankin score for drug when administered in non-hydrogel entrapped form.

The term "drug," or "pharmaceutically active agent" or "bioactive agent," or "active agent" as used interchangeably, means any organic or inorganic compound or substance having bioactivity and adapted or used for therapeutic purposes. Proteins, hormones, anti-cancer agents, small molecule chemical compounds and mimetics, oligonucleotides, DNA, RNA and gene therapies are included under the broader definition of "drug". As used herein, reference to a drug, as well as reference to other chemical compounds herein, is meant to include the compound in any of its pharmaceutically acceptable forms, including isomers such as diastereomers and enantiomers, salts, solvates, and polymorphs, particular crystalline forms, as well as racemic mixtures and pure isomers of the compounds described herein, where applicable.

The term "solid" as used herein, means a non-fluid substance, including crystalline forms, their polymorphs, non-crystalline amorphous substances, precipitates, and particles, or the like. Each of these solid forms may vary in size, from about 0.01 microns to 2,000 microns, for example, from about 0.01 microns to 1 micron, from 1 micron to 100 microns, from 100 microns to 1,000 microns, from 1000 microns to 2000 microns, from 1100 microns to 1500 microns, and from 1500 microns to 2000 microns.

Particle sizes, as referred to herein, refer to particle diameters, and are typically determined by sieve analysis. The sizes or ranges described typically correspond to a sieve or mesh opening size. One may refer to a particle size conversion chart to determine the size, e.g., in mm, corresponding to a particular mesh or screen number. See, e.g., Examples 39 and 40.

A "water insoluble drug" or "poorly water soluble drug" is one having an aqueous solubility below 10 mg/mL.

The terms "effective amount" or "pharmaceutically effective amount" or "therapeutically effective amount" of a composition (or hydrogel or polymer), as provided herein, refer to a non-toxic but sufficient amount of the composition to provide the desired response, such as preventing, diminishing, or eliminating pain in a subject. The exact amount required will vary from subject to subject, depending on the species, age, and general condition of the subject, the severity of the condition being treated, the particular drug or drugs employed, specifics of the composition, mode of administration, and the like. An appropriate "effective" amount in any individual case may be determined by one of ordinary skill in the art using routine experimentation.

"Treatment" or "treating" acute or subchronic pain includes: inhibiting pain, i.e., arresting the development or reversing pain, or relieving pain, i.e., decreasing the amount of pain experienced by the subject.

"Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about", particularly in reference to a given quantity, is meant to encompass deviations of plus or minus five percent.

Additional definitions may also be found in the sections which follow.

Overview

The present application is based, at least in part, on the inventors' discovery of hydrogels having extremely low pro-inflammatory properties when administered in vivo. In conducting studies related to the present disclosure, the inventors recognized that many biocompatible hydrogels having seemingly beneficial chemical, rheological, and other physical properties, and which behave favorably in a number of biocompatible and accepted in-vitro and in-vivo models, can cause inflammation and pain, in particular upon intra-articular injection. The materials described herein were discovered to possess remarkably low pro-inflammatory properties when examined in a goat joint injection model and compared to similar hydrogel compositions. See, e.g., Example 17 and FIGS. 4-8. Generally, the instant hydrogels, when administered into an intra-articular space of a joint (e.g., when examined in a goat joint injection model), exhibited reduced adverse or undesirable side effects on the cartilage when compared to the administration into an intra-articular space of a joint of an equivalent amount of either a commercially available viscosupplement or the administration of an equivalent amount of active agent absent hydrogel incorporation as described herein.

Unexpectedly, it has also been discovered that the incorporation of a corticosteroid into a cross-linked hydrogel such as described herein actually results in less damage to cartilage than observed upon administration of an equivalent or higher dose of corticosteroid in non-hydrogel entrapped form. See, e.g., Example 34 and FIGS. 9-13. Moreover, provided herein are results indicating that intra-articular injection of the instant hydrogels produces no local or systemic effects—either when administered alone (i.e., absent active agent) or when administered in combination with a corticosteroid such as triamcinolone acetonide.

The superior hydrogels described herein are generally formed by controlled reaction of hyaluronic acid having well-characterized, low levels of functional group modification with suitable difunctional or multi-functional crosslinkers. The resulting hydrogels are formed under mild conditions—without the need for initiators or accelerants or other deleterious additives. The resulting hydrogels are designed to possess a minimal number of unreacted, reactive groups, and are formed from a minimal number of reactants and reaction components. The hydrogels are lightly cross-linked, and have also been shown to be useful for entrapping and releasing bioactive agents in a sustained and steady fashion over time. See, e.g., FIGS. 2-3.

The features of the composition, method and kits, and the like will now be discussed in greater detail below.

Derivatized Hyaluronic Acid Polymers

The present hydrogels can be formed from a variety of polymer materials. Preferred are biodegradable or bioabsorbable polymers modified to a certain extent to contain one or more reactive functionalities. Preferably, the polymer is a polyanionic polysaccharide (PAS). Non-exclusive examples of polyanionic polysaccharides include, for example, hyaluronic acid (HA), carboxymethylcellulose (CMC), carboxymethylamylose (CMA), chondroitin-4-sulfate, chondroitin-6-sulfate, dermatan sulfate, dermatin-6-sulfate, heparin sulfate, heparin, keratin sulfate and their derivatives, and combinations thereof. Such polymers are known in the art, and described, for example, in U.S. Pat. No. 6,056,970. Other biodegradable polymers include fibrin, fibrinogen, starch, poly(amino acids); peptides, proteins, gelatin and collagen.

A preferred polymer is hyaluronic acid also referred to as hyaluronan. Hyaluronic acid is a naturally occurring linear polysaccharide composed of alternating disaccharide units of N-acetyl-D-glucosamine and D-glucuronic acid joined by alternating β 1->3 glucuronidic and β 1->4 glucosaminidic bonds, so that the repeating unit is (1->4)-β-D-GlcA-(1->3)-β-D-GlcNAc. The hyaluronic acid for use in preparing one or more of the subject hydrogels is typically derivatized with one or more reactive moieties such as vinyl sulfone, acrylate, methacrylate, and the like. Preferably, the hyaluronic acid is derivatized with a single reactive moiety. The extent of modification or derivatization can range anywhere from 1% to 100% modification of reactive functional groups within the polymer, although low levels of polymer modification are generally preferred.

One exemplary modified hyaluronic acid is hyaluronic acid derivatized by reaction of its hydroxyl groups with divinyl sulfone. The hyaluronic acid will typically have a degree of modification of reactive hydroxyl groups ranging from about 1 to about 80%. That is to say, a 1% degree of modification or substitution means that an average of 1% of the hyaluronic acid disaccharide units contain a vinyl sulrone group. Preferably, the hyaluronic acid will possess a degree of modification of reactive hydroxyl groups ranging from about 1-50%. More, preferably, the hyaluronic acid will possess a degree of modification of reactive hydroxyl groups ranging from about 1 to about 25%. In a particular embodiment, the hyaluronic acid is modified to a degree of 10% or less by reaction with divinyl sulfone. Specifically, in a preferred embodiment, the hyaluronic acid possesses 10% or less of its hydroxyl groups derivatized by an addition reaction with divinyl sulfone. The hyaluronic acid hydroxyl groups are transformed to (2-(vinylsulfonyl)ethoxy) groups. The resulting activated hyaluronic acid is referred to generally herein as (2-(vinylsulfonyl)ethoxy)hyaluronic acid or VS-HA. In particular, the hyaluronic acid may possess a degree of conversion of hydroxyl groups to (2-(vinylsulfonyl)ethoxy) groups selected from the following: 1%, 2%, 3%, 4%, 5%, 6%, 7%, 8%, 9%, and 10%. Alternatively, the hyaluronic acid may possess a degree of conversion of hydroxyl groups falling within a range between any two of the foregoing percentages: e.g., from 1-10%, 2-10%, 3-10%, 4-10%, and so forth for each and every combination of integers provided, e.g., from 2-7%, from 2-6%, from 3-8%, from 3-7%, and so forth. In yet a more specific embodiment, the hyaluronic acid has a degree of conversion of hydroxyl groups to (2-(vinylsulfonyl) ethoxy) groups of about 4-5% per disaccharide repeat unit. In certain instances, the level of hyaluronic acid functional group modification is well-characterized (i.e., determined) to allow adjustment and optimization of crosslinker concentration, along with other parameters, to thereby control the subsequent crosslinking reaction. The degree of substitution/ modification of the parent polymer can be determined by any of a number of suitable methods, e.g., NMR, UV, or IR analysis, or elemental analysis. A preferred method for calculating percent substitution of a polymer such as hyaluronic acid is NMR, e.g., proton NMR. See, e.g., Example 1 in which degree of hyaluronic acid modification was determined based upon the ratio of relative peak areas corresponding to the vinyl sulfone and the acetamide methyl group of the hyaluronic acid in the $^1$H NMR spectrum.

The polymer may also comprise hydrazide-reactive groups and/or aminooxy-reactive groups as described in PCT/US/ 2004/040726 (WO 2005/056608), relevant portions of the disclosure related to derivatization of such polymers and the resulting polymers themselves being incorporated herein by reference in their entireties.

Alternatively, the polymer may be thiol-derivatized, such as a thiol-derivatized hyaluronic acid. Exemplary thiol-derivatized hyaluronic acid polymers include those described in U.S. Pat. Nos. 6,884,788; 6,620,927; 6,548,081, 6,537,979; 6,013,679; U.S. Pat. No. 5,502,081; and 5,356,883, relevant portions of which related to such thiol-derivatized polymers being incorporated herein by reference in their entireties.

Additional examples of hyaluronic acid polymers include cysteine-derivatized hyaluronic acid, including but not limited to those polymers disclosed in "*Controlled Release from Glycosaminoglycan Drug Complexes*" R. V. Sparer et al., Chapter 6, pages 107-119, in T. J. Roseman et al., CONTROLLED RELEASE DELIVERY SYSTEMS, Marcel Dekker, Inc., New York (1983).

Examples of additional preferred polymers include hyaluronic acid derivatized by a pendent thiol group linked to an N-acyl urea group via a hydrocarbyl, aryl, substituted-hydrocarbyl, or substituted aryl group. Illustrative polymers for use in the compositions and methods provided herein include Carbylan™-S (described in detail in International Patent Publication No. WO 2005/056608).

Additional derivatized polymers include hyaluronic acid covalently attached to a reactive linker such as a difunctional or multi-functional acrylate, allyl or methacrylate compound. Representative linkers for modification of hyaluronic acid include, but are not limited to, poly (ethylene glycol)-diacrylate (PEGDA), poly (ethylene glycol)-dimethacrylate (PEGDM), poly (ethylene glycol)-diacrylamide (PEGDAA) and poly (ethylene glycol)-dimethacrylamide (PEGDMA), and derivatives thereof. The PEG-moieties of the foregoing linkers may be oliogomeric or polymeric, for example, comprising from 2 to 100 or more subunits. Additional linkers suitable for modification/functionalization of a polymer such as hyaluronic acid include dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate, sorbitol acrylate and derivatives thereof.

The derivatized hyaluronic acid or other polymer will typically possess an average molecular weight in the range of about 700 to 3,000,000 daltons, Illustrative molecular weight ranges are from about 1,000 to 2,000,000 daltons, or from about 5,000 to 1,000,000 daltons. Additional suitable molecular weight ranges include from about 50,000 daltons to about 1,000,000 daltons, or from about 100,000 daltons to about 1,200,000 daltons, or from about 90,000 daltons to about 300,000 daltons. Molecular weights of hyaluronic acid are generally average molecular mass values, which can be determined, for example, by multi-angle laser light scattering exlusion chromatography (MALLS-SEC). Depending upon its source, hyaluronic acid may have a polydispersity ($M_w/M_n$) of up to around 3, or more preferably, up to around 2. Generally, the hyaluronic acid starting material will have a rather narrow molecular weight distribution, with values less than about 2.5, more preferably less than about 2. Exemplary polydispersities of hyaluronic acid range from about 1.02 to about 2.5, where the starting hyaluronic acid may possess a polydispersity of about 1.02, 1.05, 1.1, 1.2, 1.3, 1.3, 1.5, 1.6, 1.7, 1.8, 1.9, 2.0, 2.1, 2.2, 2.3, 2.4 or 2.5, or even greater. Alternatively, a suitable hyaluronic acid starting material for derivatization may have a viscosity, typically in centipoise, at a specific concentration in water, that corresponds to any one or more of the average molecular weight ranges provided above.

Crosslinker

Examples of crosslinkers effective to form hydrogels having the advantageous features described herein include compounds having two or more reactive groups positioned upon a central molecule, "C". The central molecule may be a linear or cyclic alkane, a PEG oliogomer or polymer, or any other such suitable central molecule. In the case of crosslinkers that are PEG-based, the PEG may be linear, branched (having two polymer arms), or multi-armed (e.g., having 3, 4, 5, 6, 7, 8 or more polymer arms). Thus, in such instances, the central molecule will typically a linear PEG, a branched PEG having 2 arms, or a multi-armed PEG having PEG arms emanating from a central core. Illustrative cores for such multi-armed polymers include erythritol, pentaerythritol, trimethylolpropane, glycerol, glycerol dimer (3,3'-oxydipropane-1,2-diol), glycerol oligomers, sorbitol, hexaglycerol, and the like.

For example, the crosslinker may be a central molecule "C" having thiol or acrylate groups positioned thereon. A' thiol-containing crosslinker comprises two or more thiol groups. Such thiol groups will react with a vinyl sulfone such as within a vinyl-sulfone derivatized hyaluronic acid. Illustrative thiol cross linkers include PEG-dithiol (HS-PEG-SH), 3-arm PEG-tri-thiol (glycerine core), 4-arm PEG-tetrathiol (pentaerythritol core), or 8-arm PEG-octa-thiol (hexaglycerine core). The foregoing multi-armed PEG reagents may also have fewer than all arms functionalized with thiol. Additional suitable thiol reagents having PEG as the central molecule are available from Laysan Bio (Arab, Ala.), as well as aromatic dithiols such as those available from NanoScience. Other suitable thiol crosslinkers include dimercaptosuccinic acid, 2,3-dimercapto-1-propanesulfonic acid, dihydrolipoic acid, thiol functionalized dextran, and thiol-functionalized hyaluronic acid. Crosslinking agents having terminal acrylate groups positioned upon a central molecule may also be used. For example, suitable for use as crosslinking agents are central molecules as described above wherein the thiol groups are replaced with acylate or methacrylate groups. Further examples of crosslinkers include those described in PCT/US/2004/040726.

Crosslinkers also include molecules comprising acrylate, allyl or methacrylate groups. The acrylate, allyl or methacrylate crosslinkers can be small molecules or polymeric in nature. In one embodiment, the linker is selected from the group comprising poly (ethylene glycol)-diacrylate (PEGDA), poly (ethylene glycol)-dimethacrylate (PEGDM), poly (ethylene glycol)-diacrylamide (PEGDAA) and poly (ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof.

The molecular weight of the crosslinker is typically less than that of the modified hyaluronic acid or other polymer as described above. Generally, the molecular weight of the crosslinker ranges from about 200 to about 20,000 daltons. Additional exemplary molecular weight ranges for the crosslinker are from about 1,000 to about 10,000 daltons (e.g., having a molecular weight of about 1 kD, 2 kD, 3 kD, 4 kD, 5 kD, 6 kD, 7 kD, 8 kD, 9 kD, or 10 kD, where kD equals kilodalton) or even from about 1,000 to 5,000 daltons. Exemplary molecular weights for a crosslinker such as PEG dithiol, or any of the other suitable crosslinkers described above, include about 3350, 3400, and 5000 daltons, among others.

Bioactive Agents

The hydrogels, hydrogel precursors, and related compositions and/or kits provided herein may optionally comprise a bioactive agent. Bioactive agents that may be included in the compositions and combinations provided herein include antimicrobials, antibiotics, analgesics, antibiotics, antiproliferative/antimitotic agents including natural products such as vinca alkaloids (e.g. vinblastine, vincristine, and vinorelbine), paclitaxel, epipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine [cladribine]); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (such as brefeldin A); anti-inflammatory agents such as adrenocortical steroids (hydrocortisone, hydrocortisone acetate, cortisone acetate, tixocortol pivalate, prednisolone, methylprednisolone, prednisone, triamcinolone acetonide (or any other pharmaceutically acceptable salts of triamcinolone), triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, and fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Beclomethasone dipropionate monohydrate, flunisolide, fluticasone propionate, mometasone furoate monohydrate, triamcinolone acetonide, fluticasone, furoate, non-steroidal agents (salicylic acid derivatives e.g. aspirin); para-aminophenol derivatives, i.e. acetominophen; indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive (cyclosporine, tacrolimus (FK-506), sirolimus (rapamycin), azathioprine, mycophenolate mofetil); mitogenic or morphogenic growth factor proteins, peptides or mimetics; vascular endothelial growth factor (VEGF), fibroblast growth factor (FGF), transforming growth factor-β (TGF-β) superfamily members including TGF-β's and bone morphogenic proteins (BMP's) such as BMP-2,3,4,5,6,7,8; insulin and insulin-like growth factors (IGF's), hepatocyte growth factor (HGF), epidermal growth factors (EGF's), Hedgehog proteins (SHH and IHH), activins, inhibins, demineralized bone (DBM) and platelet-derived growth factors (PDGF's), hematopoietic growth factors (G-CSF, CSF-1, GM-CSF, erythropoietin, cytokines and lymphokines including the interleukin family (IL-1 to 34)), interferons, nerve growth factors (NGF's), neutralizing, antagonist or agonist antibodies, growth factor receptor agonists or antagonists, nitric oxide donors; anti-sense oligonucleotides, transcription factors, signaling cascade mediators, and combinations thereof.

Antibiotics include antibiotics of the lincomycin family (referring to a class of antibiotic agents originally recovered from *streptomyces lincolnensis*); antibiotics of the tetracycline family (referring to a class of antibiotic agents originally recovered from *streptomyces aureofaciens*); sulfur-based antibiotics such as the sulfonamides; and so forth. Exemplary antibiotics of the lincomycin family include lincomycin itself (6,8-dideoxy-6-[[(1-methyl-4-propyl-2-pyrrolidinyl)-carbonyl]amino-]-1-thio-L-threo-☐-D-galacto-octopyranoside), clindamycin, the 7-chloro derivative of lincomycin (e.g., 7-chloro-6,7,8-trideoxy-6-[[(1-methyl-4-propyl-2-pyrrolidinyl)carbonyl]amino]-1-thio-L-threo-☐-D-galacto-octopyranoside), and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Antimicrobials and/or antibiotics further include compounds such as erythromycin, bacitracin, neomycin, penicillin, polymyxin B, tetracyclines, viomycin, chloromycetin and streptomycins, cefazolin, ampicillin, azactam, tobramycin, clindamycin and gentamycin.

Analgesics include compounds such as lidocaine, benzocaine, and marcaine.

A hydrogel as provided herein may also include living cells. Exemplary living cells include stem cells, parenchimal stem cells, blood-derived cells, and bone marrow cells.

In one preferred embodiment, the hydrogel comprises a corticosteroid. Examples of suitable corticosteroids include hydrocortisone, hydrocortisone acetate, cortisone acetate, tixocortol pivalate, prednisolone, methylprednisolone, prednisone, triamcinolone, triamcinolone salts such as triamcinolone acetonide, triamcinolone benetonide, triamcinolone furetonide, triamcinolone hexacetonide, triamcinolone diacetate, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, beclomethasone dipropionate monohydrate, flunisolide, fluticasone propionate, mometasone furoate monohydrate, and fluticasone furoate.

One preferred compound for use in a hydrogel formulation as provided herein is triamcinolone (11β,16α)-9-fluoro-11,16,17,21-tetrahydroxypregna-1,4-diene-3,20-dione), or a pharmaceutically acceptable salt or solvate thereof. The structure of triamcinolone acetonide is shown below.

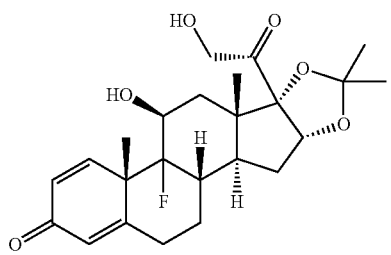

The bioactive agent will typically be admixed, suspended in, or entrapped within a hydrogel as provided herein. Alternatively, the bioactive agent may be in the form of a polymer conjugate, or, may be covalently attached, in a releasable fashion, to a component used to prepare the hydrogel, e.g., the modified hyaluronic acid or crosslinker.

Hydrogels

The hydrogels provided herein are typically formed by reacting a modified hyaluronic acid or other suitable polymer as described above with a crosslinking agent (also described above) under conditions effective to form a gel. Generally, the relative amounts of reagents and reactive groups, along with reaction conditions, are adjusted to provide optimal reaction. Gel formation is carried out under mild and controlled conditions. Preferably, the resulting hydrogel contains less than twenty percent of combined unreacted functional groups contained within the modified hyaluronic acid and the crosslinker starting materials, more preferably 5% or less of unreacted functional groups contained within the modified hyaluronic acid and the crosslinker starting materials, or ideally, essentially no detectable amounts of unreacted functional groups such as unreacted vinyl sulfone or thiol groups. Such low levels of unreacted functional groups in the resulting gel material are beneficial in terms of providing a gel material having low pro-inflammatory properties when administered in vivo, e.g., into a joint. In a particular embodiment, a hydrogel formed by reaction of (2-(vinylsulfonyl)ethoxy)$_{1-10\%}$hyaluronic acid with a thiol crosslinker contains less than ten percent of unreacted thiol and vinyl sulfone groups. The number of unreacted functional groups is controlled by careful monitoring of reaction conditions, adjustment of reactant ratios, and knowledge of the degree of modification of the hyaluronic acid starting material.

Hydrogels thus formed will typically contain a percent by weight (wt/wt) of polymer to water (POLY/HOH) ranging from about 0.5 to 5.0 percent or even more. Illustrative percents by weight of polymer to water for the resulting hydrogel are, in one or more embodiments, selected from 0.5, 1.0, 1.5, 2.0, 2.5, 3.0, 3.5, 4.0, 4.5 and 5 percent.

Formation of the lightly crosslinked hydrogels provided herein is due at least in part to the low level of modification in the modified-hyaluronic acid starting material. For instance, the degree of modification of hyaluronic acid by reaction with divinyl sulfone can be controlled by appropriate adjustment of reaction times as shown in Example 6. For example, in order to maintain a degree of modification below about 20%, the reaction time under ambient conditions (e.g., from 20-25° C.) is generally kept under about 3 minutes to form 2-(vinylsulfonyl)ethoxy)$_{1-20\%}$hyaluronic acid. The reaction is preferably conducted using a molar excess of divinyl sulfone or other appropriate modification reactant, such as a difunctional or greater acrylate or methyacylate reagent. As can be seen from the results in Example 6, and as would be expected, shorter reactions times result in lower degrees of modification of the starting polymer, e.g., hyaluronic acid. For example, under ambient conditions, a very short reaction time, i.e., on the order of seconds, resulted in vinyl-sulfone modified hyaluronic acid having about 4% substitution of vinyl sulfone groups, while a reaction time of one minute resulted in 8% vinyl sulfone-substituted hyaluronic acid. See Table 1 for illustrative reaction times and conditions and the resulting degrees of substitution of polymer obtained. In one embodiment, the reaction conditions are adjusted to result in vinyl-sulfone-substituted hyaluronic acid having from about 1% to about 10% substitution. In a related embodiment, the modification reaction is carried out under ambient conditions for about 10 seconds to about 120 seconds. The modification reaction, e.g., reaction of hyaluronic acid and divinyl sulfone, can be carried out under basic conditions, e.g., in aqueous base such as aqueous sodium hydroxide, aqueous potassium hydroxide, or using any other suitable base that is soluble in water, followed by quenching of the reaction by addition of acid, such as hydrochloric acid, sulfuric acid, phosphoric acid, or the like. Generally, acid is added at such time and in an amount sufficient to adjust the pH down to a range from about 4 to 6.5 or so, to quench the reaction to thereby achieve a desired degree of functional group modification of the parent polymer. The product may then be optionally purified, e.g., by dialysis, and optionally dried such as by lyophilization.

The hydrogel precursor composition is then lightly cross-linked, optionally in the presence of a cross-linking agent if necessary. For example, a vinyl-sulfone modified hyaluronic acid such as 2-(vinylsulfonyl)ethoxy$_{120\%}$hyaluronic acid, or 2-(vinylsulfonyl)ethoxy$_{1-10\%}$hyaluronic acid, such as described above, is reacted with a suitable crosslinker such as a thiol-functionalized PEG reagent such as PEG-dithiol or other appropriate crosslinking agent as described above under reaction conditions effective to form a crosslinked hydrogel. In a preferred embodiment, the crosslinking reaction is carried out in aqueous solution, e.g., under physiological conditions. In one embodiment, the reaction is carried out in saline solution. See, e.g., Examples 2, 3, 4, and 5. The volume ratios of reactants can be adjusted according to the desired properties of the resulting hydrogel, and will depend upon the concentrations of the reactant solutions, the particular molecular weights and structures of the reactants, and the like. For instance, illustrative relative molar ratios of functional group to crosslinker include the following, where, e.g., an exemplary functional group is vinyl sulfone as contained in the vinyl-sulfone modified hyaluronic acid and relative amount of crosslinker refers to crosslinker itself, for example, the crosslinker molecule rather than the number of reactive groups such as thiol groups contained in a crosslinker molecule such as in PEG-dithiol: from about 1 to 2.5, or from about 1.25 to 2.0, or from about 1.3 to about 1.8. Alternatively, the crosslinker may be added as a solid to a solution of the modified hyaluronic acid. In an instance in which a sterile formulation is desired, the crosslinker is sterilized prior to addition, e.g., by electron-beam treatment. The crosslinking reaction is typically carried out under mild reaction conditions, e.g., at temperatures ranging from about 20° C. to about 45° C., e.g., at any one of the following temperatures: 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. Following mixing or reacting of the modified hyaluronic acid and crosslinker reactants, and any other optional reactant components, the resulting composition is typically allowed to react, e.g., in an incubator, for a period of time suitable to result in formation of a gel. Depending on the reaction temperature, the reactants are typically allowed to react for a period of about 8 to about 36 hours, or from about 10 to about 24 hours, or for about 12 to about 18 hours.

The crosslinking reaction may be carried out under sterile conditions, i.e., using sterile reactants and under sterile conditions as described generally in the accompanying examples, to provide a sterile hydrogel. For instance, all solution components may be sterile filtered prior to reaction to thereby form a sterile composition.

Additional exemplary lightly crosslinked hydrogels are formed, e.g., by cross-linking of thiol-modified hyaluronic acid materials such as Carb-S™. Carb-S™ is produced by carboxymethylation of hyaluronic acid, followed by reaction with 3,3' dithiobis(propanoic dihydrazide), DTPH, in the presence of a coupling agent, followed by reduction of the disulfide groups with a reagent such as dithiothreitol. See, e.g., U.S. Patent Publication No. US2008-002595. Additional thiol-modified hyaluronic acid materials are described in U.S. Patent Publication No. US2009-0105093; an illustrative material described in the foregoing publication is a hyaluronic acid derivatized by reaction with a thiol-containing hydrazide reactant. The hydrogel may also be formed from a thiol-modified hyaluronic acid material as described in U.S. Pat. No. 6,884,788. In a preferred embodiment, the foregoing thiol-modified hyaluronic acid materials are prepared using the synthetic approaches described, with the exception that the degree of modification of the hyaluronic starting material is low, such that less than about 20% or even more preferably, less than about 10% of the hyaluronic acid hydroxyl groups are chemically modified. Such thiol-derivatized hyaluronic acid materials can be lightly self-crosslinked, due to the ability of thiols to self-react. Alternatively, the lightly cross-linked hydrogel may be formed by reaction with a cross-linking agent such as a PEG-acrylate.

In one or more particular embodiments, the crosslinked hydrogel composition contains an active agent. Preferred classes of bioactive agents include steroids, growth factors, anti-proliferative agents, and antibiotics. One particularly advantageous class of active agent for incorporation into the instant hydrogels are the corticosteroids. Illustrative corticosteroids include but are not limited to the following: triamcinolone, triamcinolone salts such as triamcinolone acetonide, triamcinolone hexacetonide, triamcinolone benetonide, triamcinolone furetonide, and triamcinolone diacetate and the like, and methylprednisolone. Generally, the resultant hydrogel contains from about 0.01% by weight to about 20% by weight bioactive, depending on its potency. Illustrative amounts of bioactive agent contained in the hydrogel (based on overall wet gel weight) are from about 10% to about 20% by weight, e.g., for a less potent bioactive agent, and from about 0.01% to about 10% by weight, or from about 0.01% to about 5%, or from about 0.01% to about 3%, or from about 0.1 to about 2% bioactive agent, or even from about 0.1 to about 1% bioactive agent, e.g., for a more potent bioactive agent such as triamcinolone acetonide. In certain embodiments, the hydrogel is used for delivering a poorly water soluble bioactive agent by incorporating such bioactive agent in the hydrogel.

Advantageously, the present hydrogels are formed both under mild reaction conditions and can be formed in the absence of a polymerization initiator. Moreover, sufficient gellation occurs in the absence of the application of an external energy source. For example, the gel-formation reaction can be carried out at a temperature ranging from about 20° C. to 45° C.—and in the absence of initiators and accelerants. Additionally, the gelation, i.e., hydrogel formation, occurs without the release of any small molecule chemical by-products. Thus, the hydrogels provided herein contain a minimal number of additives or contaminants that could potentially lead to a pro-inflammatory response upon in-vivo administration.

Sterile hydrogels can be formed under sterile conditions, e.g., by placing aqueous solutions of each of the modified hyaluronic acid and crosslinker into a sterile syringe and or centrifuge tube, followed by thorough mixing. Typically the mixed reactants (i.e., modified hyaluronic acid and crosslinker) are placed in an incubator set at an appropriate temperature (e.g., ranging from about 20° C. to 45° C.) until the material forms a gel. See, e.g., Example 2, 18, 21, 22, 23, 24, 25, 27, 28, 29 and 30 for representative preparations of hydrogel formulations, including exemplary volume ratios of reactants.

Additional unmodified hyaluronic acid, typically in the form of an aqueous solution or mixture, may optionally be added to either the gel precursor formulation, prior to gel formation, or after gel formation (e.g., to a gel slurry), to provide a composition comprising crosslinked hydrogel particles in an aqueous solution of hyaluronic acid. See, e.g., Example 8. The average molecular weight of the hyaluronic acid (i.e., unmodified hyaluronic acid) in the solution typically ranges from about 750,000 to about 1,200,000 daltons or even higher. A preferred aqueous solution is a saline solution of hyaluronic acid, where exemplary aqueous solutions of hyaluronic acid added to the hydrogel have concentrations ranging from about 0.3% to about 4%, or from about 0.5% to about 2% by weight. One representative formulation comprises the following relative amounts of components: 4 mL of gel slurry ((2-(vinylsulfonyl)ethoxy)$_{1-10\%}$hyaluronic acid/PEG-dithiol) with 2 mL of hyaluronic acid at a concentration of 20 mg/mL. A particularly preferred formulation comprises 4 mL of gel slurry ((2-(vinylsulfonyl)ethoxy)$_{4\%}$hyaluronic acid/PEG-dithiol) with 2 mL of hyaluronic acid at a concentration of 20 mg/mL. Typically, the final hyaluronic acid content in the resulting swollen gel ranges from about 0.05 to 5 percent (0.5 mg/mL to 50 mg/mL). Preferably, the final hyaluronic acid content in the resulting swollen gel is from about 0.1 to 3 percent, or from about 0.1 to 1 percent, or from about 0.5-0.8%. Illustrative final hyaluronic acid content in the resulting swollen gel may, for example, correspond to any of the following percentages: 0.1, 0.2, 0.3, 0.4, 0.5, 0.6, 0.7, 0.8, 0.9, 1.0, 2.0, 3.0, 4.0, and 5.0. For example, representative relative amounts (weight ratios) of hyaluronic acid to crosslinked (e.g., (2-(vinylsulfonyl)ethoxy)$_{1-10\%}$hyaluronic acid/PEG-dithiol) hydrogel particles in the resultant composition typically fall within a range from about 10:1, or from about 5:1, or from about 3:1, or from about 1:1. The resulting composition may also optionally contain one or more surfactants. Illustrative surfactants include sodium carboxymethylcellulose, polysorbate 80, Tween 80, polyethylene glycol (e.g., PEG 3350), and the like.

If desired, a bioactive agent may be added to the reaction mixture prior to crosslinking or alternatively, added to the crosslinked gel after formation. Examples 9-16 demonstrate hydrogel formation, as well as incorporation and subsequent sustained release of a bioactive agent, triamcinolone acetonide, from representative hydrogel compositions. Alternatively, living cells such as stem cells, parenchimal stem cells, blood derived cells, and bone marrow cells can be incorporated into the subject hydrogels.

For the subject hydrogels, with or without a bioactive agent, the hydrogel can be dispersed in a solution of one or more polyanionic polysaccharides (PAS) as described above. Non-exclusive examples of polyanionic polysaccharides include, for example, in addition to hyaluronic acid (HA), carboxymethylcellulose (CMC), carboxymethylamylose (CMA), chondroitin-4-sulfate, chondroitin-6-sulfate, dermatan sulfate, dermatin-6-sulfate, heparin sulfate, heparin, keratin sulfate and their derivatives, and combinations thereof. Such polymers are known in the art, and described, for example, in U.S. Pat. No. 6,056,970. Other solutions of polymers that the subject hydrogels can be dispersed in include fibrin, fibrinogen, starch, poly(amino acids); peptides, proteins, gelatin, collagen and poly(ethylene glycol). A solution containing one or more combinations of the above polymers can be used to disperse the subject hydrogel particles. The polymer solutions can be prepared in a concentration range from at least 0.1 mg/mL to the maximum water or 0.9% saline solubility. As described previously, one preferred polymer is hyaluronic acid having a molecular weight between about 500,000 and 3 million at a concentration range of about 10 mg/mL to about 25 mg/mL. The combination of polymer solution and hydrogel can be manufactured under aseptic conditions such that the final packaged combination is sterile.

As described in Example 8, the subject hydrogels can be mixed in different ratios with the selected polymer solution. Volume ratios of mixing the subject hydrogel and the polymer solution can include but are not limited to about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1. The preferred volume ratios of mixing the subject hydrogel and the polymer solution are about 3:1, 2:1 and 1:1.

The pH of the subject hydrogels and subject hydrogel/polymer solution dispersions can be modified by the addition of buffers, acid and bases. The preferred pH range for the subject hydrogels and subject hydrogel/polymer solution dispersions is from about 5-8 and more preferably from about 6-7.6.

The ionic strength of the subject hydrogels and subject hydrogel/polymer solution dispersions can be modified by the addition of salts. One preferred salt used to modify the ionic strength of the subject hydrogels and subject hydrogel/polymer solution dispersions is sodium chloride. A preferred final ionic strength of the subject hydrogels and subject hydrogel/polymer solution dispersions is selected such that the subject hydrogels and subject hydrogel/polymer solution dispersions are about isotonic.

Pharmaceutically acceptable preservatives may also be added to the subject hydrogels and subject hydrogel/polymer solution dispersions. These can include agents such as sodium benzoate or benzyl alcohol.

The subject hydrogels and subject hydrogel/polymer solution dispersions may, in certain embodiments, be packaged in a syringe. The syringe can be made from plastic (e.g. polypropylene, polycarbonate, polystyrene) or glass or any other pharmaceutically acceptable material. The volume of the subject hydrogels and subject hydrogel/polymer solution dispersions contained within the syringe may range from 0.5 mL to 20 mL with preferable volumes being 1 mL, 2 mL, 3 mL, 4 mL, 5 mL, 6 mL and 7 mL.

The resulting hydrogel material may be processed into particles having a size ranging from about 0.10 to 3.0 millimeters (See, e.g., Examples 3 and 4), or may be in the form of an aqueous gel slurry. For example, gelled material can be broken up into pieces, mixed with saline, and allowed to swell. Appropriately sized particles can then be formed from the gel material by extrusion through a mesh having the desired screen size, e.g., from about 0.10 to 3.0 millimeters. The resulting particles, when placed in an aqueous medium, form a gel slurry. In one embodiment, the gel is packaged in a syringe suitable for use with a 18-21 gauge needle, such that the hydrogel can be injected, i.e., into an intra-articular space. Generally, the volume of hydrogel composition injected into an intra-articular space of a subject ranges from about 0.5 to about 8 mL, preferably from about 3 to 6 mL, or even from about 4-6 mL.

As illustrated in the accompanying Examples, the hydrogels can be provided as sterile compositions.

As described above, and in the Examples, the hydrogels may be provided in a sealed container such as a syringe (which can be capped, optionally with a vented cap). The syringe may then be placed in a container, such as a foil pouch which is then sealed. The pouch may be vacuum sealed, sealed under an inert gas such as nitrogen or argon, or sealed following one or more vacuum/back fill cycles where the back fill gas is an inert gas such as nitrogen or argon. For the pouch sealed under one or more vacuum/back fill cycles, the cycle can be adjusted such that the pouch is finally sealed under either vacuum or an inert gas. The pouch may optionally contain a dessicant and/or an oxygen scavenger.

Uses

The gel compositions described herein advantageously exhibit reduced undesirable side effects on the cartilage in comparison to commercially available viscosupplements and, in embodiments in which the hydrogel further comprises a bioactive agent, exhibit reduced undesirable side effects on the cartilage when compared to administration of an equivalent amount of active agent absent hydrogel incorporation. The gel compositions provided herein possess extremely low pro-inflammatory properties as illustrated in Example 17 and in FIGS. 4-8, amongst having other beneficial features.

The hyaluronic acid polymer compositions described herein may be used in injectable or implantable formulations, for use, e.g., embryonic development, tissue organization, wound healing, angiogenesis and tumorigenesis. See D. D. Allison and K. J. Grande-Allen, *Tissue Engineering*, Vol. 12, Number 8, 2131-2140 (2006); G. D. Prestwich et al, *Tissue Engineering*, Vol. 12, Number 8, 2171-2180 (2006); G. D. Prestwich et al, *Tissue Engineering*, Vol. 12, Number 12, 3405-3416 (2006). Hydrogel compositions comprising a corticosteroid such as triamcinolone acetonide are useful for providing relief of pain experienced by a subject. Injection of a therapeutically effective amount of the hydrogel composition into an intra-articular space of a joint can be effective, e.g., for providing sustained relief of joint pain experienced by a subject. Ideally, a measurable degree of pain relief is initially experienced by the subject from within about one hour to one week post-injection, or more preferably, from about one hour to about one day post-injection. Typically, injection of the hydrogel results in a degree of relief of pain lasting from about three to nine months post-injection. Depending upon the particular subject and condition to be treated, a therapeutically effective dosage volume of hydrogel typically ranges from about 0.5 mL to 20 mL, with exemplary volumes including 2 mL, 3 mL, 4 mL, 5 mL, 6 mL and 7 mL.

For example, the hydrogel compositions provided herein, optionally containing one or more bioactive agents, may be used as adhesive compositions, e.g., as tissue adhesives and sealants that may be used for various applications, including preventing bleeding, covering open wounds, and other biomedical applications. These compositions may be used in, for example, apposing surgically incised or traumatically lacerated tissues, retarding blood flow such as those from wounds, preventing restenosis or blood clotting, drug delivery; dressing burns, and aiding repair and regrowth of living tissue. The hyaluronic acid-based polymer composition as provided herein may be used for supplementing or inducing and regenerating damaged organs or tissues in a mammalian subject, such as a human. The composition is decomposed or absorbed, or alternatively, remains in the subject (e.g., mammalian subject) without having adverse influences on subject when embedded or contained therein.

The subject compositions may be used as tissue fillers, dermal fillers, bulking agents, and embolic agents as well as agents to repair cartilage defects/injuries and agents to enhance bone repair and/or growth.

The subject compositions may also be used in the treatment of osteoarthritis or rheumatoid arthritis, or for other inflammatory arthritides such as gout or calcium pyrophosphate deposition disease (e.g., by injection into the intra-articular space of a joint), or in the reduction or prevention of adhesions that can form following a surgical procedure. It has been discovered that the subject compositions are useful for reducing the damage to cartilage upon injection of a corticosteroid by incorporation of the corticosteroid into a hydrogel material as provided herein.

As one particular measure of the foregoing, i.e., when the hydrogel comprises a corticosteroid incorporated therein, and the method is effective to result in damage to the cartilage that is reduced from the cartilage damage that occurs upon administration of an equivalent amount of the corticosteroid absent hydrogel entrapment, such reduced damage to the cartilage is characterized in a goat joint injection model by total Mankin score at 28 days post injection. See Example 34 for a description of determination of total Mankin score. Additional indicators for assessing reduced cartilage damage are also available; such parameters and associated data are also provided in Example 34.

Several advantages are associated with the entrapment/incorporation of steroid particles within a hydrogel as provided herein, including one or more of the following. For instance, the trapping of steroid particles within the instant hydrogels is effective to prevent direct contact of the majority of the steroid particles with the joint tissues. Moreover, the trapping of steroid particles in the instant hydrogels is effective to maximize the localized concentration of the steroid in the joint, while minimizing its systemic concentration. Additionally, the entrapment of steroid particles in the instant hydrogel formulations is effective to protect the steroid particles from premature clearance from the joint. Finally, by entrapping the steroid in the hydrogel, therapeutic efficacy of the steroid is attained at a lower total dose than would be attained absent hydrogel entrapment, while minimizing unwanted local and systemic side effects. See, for example, Examples 14-16 along with FIGS. 2, 3, and 4, demonstrating linear release of drug from an exemplary hydrogel composition in a controlled and sustained linear fashion over time.

For hydrogel-based compositions comprising a bioactive agent, such compositions may be used as delivery systems for the treatment of conditions such as osteoarthritis, sinusitis, allergic rhinitis and chronic rhinosinusitis, among others. Such compositions may also be used as dermal fillers, agents to repair cartilage defects/injuries and agents to enhance bone repair and/or growth.

The present application will now be described in connection with certain embodiments, which are not intended to limit the scope of the invention. On the contrary, the present application covers all alternatives, modifications, and equivalents as included within the scope of the claims. Thus, the following will illustrate the practice of the present application, for the purposes of illustration of certain embodiments and is presented to provide what is believed to be a useful and readily understood description of its procedures and conceptual aspects.

EXAMPLES

The following examples are put forth to provide those of ordinary skill in the art with a complete disclosure and description of how the compounds, compositions, and methods provided herein are made and evaluated, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize product characteristics such as purity, yield, and the like. Such are considered as well within the scope of the present disclosure.

Example 1

Synthesis of Vinyl Sulfone Derivatized Hyaluronic Acid (Ha-Vs)

Low Degree of Modification

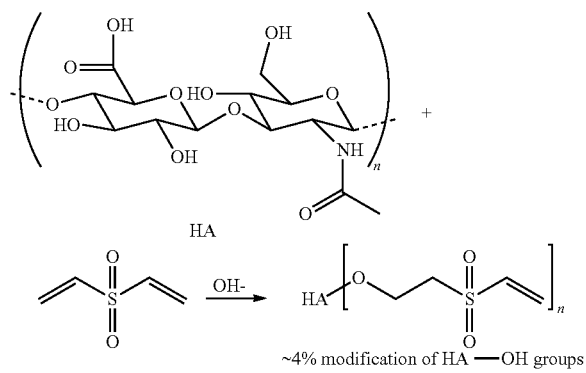

~4% modification of HA—OH groups 5 g hyaluronic acid (HA) [9.4×10⁴ cps (3% in water)] was weighed into a 1 L round bottom flask. 500 mL sterile filtered water was added to the HA. The flask was placed on a rotary evaporator which was set to rotate at between 20-100 rpm. The solution was rotated until all the HA was dissolved (approx. 16-18 hrs). The HA solution (10 mg/mL) was then transferred to a 1 L glass beaker. A stirring paddle that was connected to an overhead stirrer was inserted into the solution and was set to a stirring speed that ensured efficient stirring of the solution. 333 mL of a 0.25 N NaOH solution (83.2 mL 1N NaOH added to 249.8 mL deionized water) was added to the stirring HA solution. After about 1 min, 150 mL of a divinyl sulfone solution (18 mL divinyl sulfone dissolved in 132 mL deionized water) was added rapidly to the stirring solution. After 15 seconds (as measured from the completion of the divinyl sulfone solution addition), the pH of the solution was adjusted to between 5 and 6 by rapidly adding approx. 14 mL 6N HCl. The reaction solution was then dialysed using a tangential flow filtration system (spectrapor system, cartridge P/N M6-100S-301-01P). The total volume was 11 times the original solution volume. Once the purification step was completed, the solution was concentrated to approx. 14-20 mg/mL. The vinyl sulfone functionalized HA (HA-VS) was removed from the TFF system and was placed in a plastic container which was then closed with a screw top lid. A sample of the HA-VS was removed, frozen at −80° C. and then lyophilized. The dried sample was sent for H-NMR analysis.

Determination of Percentage Vinyl Sulfone Substitution for HA-VS

Approx. 15-17 mg of the dried sample was weighed into a tared 2 mL tube. The sample was reconstituted in 1.5 mL D₂O. The sample was transferred to an NMR tube. The ¹H-NMR (256 scans) of the sample was taken and the spectrum was printed out with the specific peaks in the 6.3-6.5 ppm (2 peaks from the 2 CH₂=protons from the vinyl sulfone residue) and 1.5-2.5 ppm (singlet from the 3 CH₃-protons from the N-acetyl group of the HA) regions being integrated. The percent modification is calculated as follows:

$$\% \text{ modification} = 150 \times \frac{\text{Integral vinyl sulfone peaks}}{\text{Intergral Acetamide peak}}$$

The ¹H-NMR spectrum (FIG. 1) showed that the HA had a vinyl sulfone substitution level of approximately 4%, based upon an integration of vinyl sulfone peaks relative to the acetamide methyl group of the hyaluronic acid.

A sample of the HA-VS was used to determine the dry weight which was used to determine the specific concentration of the HA-VS solution. The HA-VS concentration was 18 mg/mL.

Example 2

Synthesis of a Gel Prepared from Vinyl Sulfone Modified Hyaluronic Acid (Ha-Vs) and PEG3400-Dithiol A solution of HA-VS, prepared as described in Example 1, was diluted using deionized water to a concentration of 14 mg/mL. 11 mL of the HA-VS solution was placed into a 20 mL sterile syringe. The HA-VS solution was filtered through a 0.2 µm sterile syringe filter into a sterile 50 mL centrifuge tube. A 50 mg/mL solution of PEG-(SH)₂ [Laysan Bio Inc, Item# SH-PEG-SH-3400-1 g] was prepared by dissolving 40.1 mg PEG-(SH)₂ in 0.802 mL deionized water. The PEG-(SH)₂ solution was transferred to a 1 mL sterile syringe and was filtered through a 0.2 µm sterile syringe filter. 10 mL of the sterile filtered HA-VS was transferred to a sterile 50 mL centrifuge tube. 250 µL of a 0.5 M sodium phosphate solution (filtered through a 0.2 µm sterile syringe filter) was added to the HA-VS solution. The resultant solution was mixed thoroughly. 380 µL [19 mg PEG-(SH)₂] of the sterile 50 mg/mL PEG-(SH)₂ solution was added to the HA-VS solution. The resultant solution was mixed thoroughly. The above steps were performed in a biohood to maintain sterility. The HA-VS/PEG-(SH)₂ solution was then placed in a 37° C. incubator for at least 16 hours to promote gel formation. After at least 16 hours, the HA-VS/PEG-(SH)₂ solution had crosslinked to form a gel. The gelled material was then removed from the incubator.

Example 3

Preparation of a HA-VS/PEG-(SH)₂ Gel Slurry

Single Extrusion

The HA-VS/PEG-(SH)₂ gel from Example 2 was physically broken into pieces using a glass rod. The gel was transferred to a sterile 60 mL syringe that was capped with a syringe cap. 40 mL 0.9% sterile NaCl was added to the gel. The plunger was inserted into the syringe barrel and the syringe was inverted. The syringe cap was opened to release any pressure and was then closed. The syringe was inverted several times to ensure good mixing of the saline and the gel pieces. The gel was allowed to swell overnight (at least 16 hrs).

A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved. The syringe cap of the syringe was removed and the syringe filter containing the mesh was attached to the syringe. The gel was extruded through the mesh into a sterile 50 mL centrifuge tube. The centrifuge tube was capped with a screw top lid. The resulting product is a slightly viscous slurry of the particles, where the particles do not really settle out but typically remain suspended. The above steps were performed in a biohood.

Example 4

Preparation of a HA-VS/PEG-(SH)$_2$ Gel Slurry

Double Extrusion

The HA-VS/PEG-(SH)$_2$ gel from Example 2 was physically broken into pieces using a glass rod. The gel was transferred to a sterile 60 mL syringe that was capped with a syringe cap. 40 mL 0.9% sterile NaCl was added to the gel. The plunger was inserted into the syringe barrel and the syringe was inverted. The syringe cap was opened to release any pressure and was then closed. The syringe was inverted several time to ensure good mixing of the saline and the gel pieces. The gel was allowed to swell overnight (at least 16 hrs).

A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved. The syringe cap of the syringe was removed and the syringe filter containing the mesh was attached to the syringe. The gel was extruded through the mesh into a sterile 50 mL centrifuge tube. The extruded gel was then put into a sterile 60 mL syringe and the syringe filter that contained the mesh was attached to the syringe. The gel was extruded through the through the mesh into a sterile 50 mL centrifuge tube. The centrifuge tube was capped with a screw top lid. The above steps were performed in a biohood.

Example 5

Preparation of Syringes Loaded with HA-VS/PEG-(SH)$_2$ Gel Slurry 5 mL of the prepared HA-VS/PEG-(SH)$_2$ gel slurry (from Example 3 or Example 4) was transferred into a sterile 10 mL glass syringe (B&D) that had a syringe cap applied. A sterile stopper was inserted into the top of the syringe. A plunger rod was screwed into the stopper. The syringe was inverted and once the gel slurry had reached the stopper, the syringe cap was loosened slightly and the plunger was depressed until the majority of the air in the syringe was removed. The syringe cap was tightened. The above steps were performed in a biohood.

Example 6

Synthesis of Vinyl Sulfone-Derivatized Hyaluronic Acid

HA-VS compositions having different degrees of substitution were prepared using the method described in Example 1, with the exception that reaction times were increased. By increasing the reaction time, a greater degree of vinyl sulfone substitution was obtained. The results of these reactions are shown in the table below:

TABLE 1

| REACTION TIME | DEGREE OF SUBSTITUTION FOR VSMODIFIED HA |
| --- | --- |
| 15 sec | 4% |
| 1 minute | 8% |
| 3 minutes | 20% |
| 5 minutes | 26% |
| 25 minutes | 29% |

Example 7

Synthesis of HA-VS/PEG-(SH)$_2$ Gel

The HA-VS samples having varying levels of vinyl sulfone substitution (Example 6) were used to prepare HA-VS/PEG-(SH)$_2$ gels using the method and reagent ratios described in Example 2. Each of the starting materials formed a gel upon reaction with PEG-dithiol.

Example 8

Preparation of HA-VS/PEG-(SH)$_2$ Gel Slurry With Hyaluronic Acid 2 g hyaluronic acid [$9.4 \times 10^4$ cps (3% in water)] was weighed into a 250 mL round bottom flask. 100 mL sterile saline was added to the hyaluronic acid in the flask. The flask was attached to a rotary evaporator (Buchi) and was rotated at 50 rpm for at least 16 hrs to form a 2% hyaluronic acid solution. The following series of steps were performed in a biohood. The hyaluronic acid solution was filtered through a 0.2 um sterile filter. Using the HAVS/PEG-(SH)2 gel slurry (as prepared in Example 3 or 4), a series of formulations were prepared in which the prepared HA-VS/PEG-(SH)2 gel slurry was mixed with hyaluronic acid. The volumes of the hyaluronic acid solution and the HA-VS/PEG(SH)$_2$ gel slurry used to prepare these formulations are shown in the table below:

TABLE 2

| FORMULATION | VOLUME HYALURONIC ACID (ML) | VOLUME HA-VS/PEG-(SH)$_2$ GEL SLURRY (ML) |
| --- | --- | --- |
| 1 | 1 | 5 (single extrusion slurry) |
| 2 | 2 | 4 (single extrusion slurry) |
| 3 | 3 | 3 (single extrusion slurry) |
| 4 | 4 | 2 (single extrusion slurry) |

TABLE 2-continued

| FORMULA-TION | VOLUME HYALURONIC ACID (ML) | VOLUME HA-VS/PEG-(SH)$_2$ GEL SLURRY (ML) |
|---|---|---|
| 5 | 5 | 1 (single extrusion slurry) |
| 6 | 1 | 5 (double extrusion slurry) |
| 7 | 2 | 4 (double extrusion slurry) |
| 8 | 3 | 3 (double extrusion slurry) |
| 9 | 4 | 2 (double extrusion slurry) |
| 10 | 5 | 1 (double extrusion slurry) |

The indicated volumes of hyaluronic acid solution and HA-VS/PEG-(SH)2 gel slurry, as identified in the table above, were added to a 15 mL sterile centrifuge tube. The cap was placed on the tube and the tube was inverted back and forth until the components were well mixed. Each formulation was then transferred into a 10 mL glass syringe that had a syringe cap after which the plunger was inserted and the excess air was expelled. The syringe cap was then tightened.

Example 9

Synthesis of HA-VS-PEG-(SH)$_2$ Gel Containing Triamcinolone Acetonide

A solution of the HA-VS, prepared as in Example 1, was diluted using deionized water to a concentration of 14 mg/mL. 11 mL HA-VS solution was placed into a 20 mL sterile syringe. The HA-VS solution was filtered through a 0.2 um sterile syringe filter into a sterile 50 mL centrifuge tube. A 50 mg/mL solution of PEG-(SH)$_2$ was prepared by dissolving 40.1 mg PEG3400-(SH)$_2$ in 0.802 mL deionized water. The PEG-(SH)$_2$ solution was transferred to a 1 mL sterile syringe and was filtered through a 0.2 um sterile syringe filter. 10 mL of the sterile filtered HA-VS was transferred to a sterile 50 mL centrifuge tube. 100 mg of triamcinolone acetonide (Spectrum Chemicals, U.S.P grade, micronized) was added to the HAVS solution. The cap of the centrifuge tube was placed on the tube and the solution was inverted back and forth until the triamcinolone acetonide was homogeneously mixed with the HA-VS. 250 μL of a sterile filtered (0.2 um sterile filter) 0.5 M sodium phosphate solution was added to the HA-VS solution. The resultant solution was mixed thoroughly. 380 μL of the sterile 50 mg/mL PEG-(SH)$_2$ solution was added to the HA-VS solution. The resultant solution was mixed thoroughly. The above steps were performed in a biohood. The HA-VS/PEG-(SH)$_2$ solution was then placed in a 37° C. incubator for at least 16 hours. At this stage the HA-VS/PEG(SH)$_2$ solution had crosslinked to form a gel. The gelled material was then removed from the incubator. The resulting gel contains approximately 0.2% triamcinolone acetonide.

The above procedure was also carried out as set forth above with the exception that 20 mg of triamcinolone acetonide (Spectrum Chemicals, U.S.P grade, micronized) was added to the HA-VS solution.

Example 10

Preparation of HA-VS-PEG-(SH)$_2$ Gel Slurry Containing Triamcinolone Acetonide: Single Extrusion The triamcinolone acetonide-containing HA-VS/PEG-(SH)$_2$ gel (Example 9) was physically broken into pieces using a glass rod. The gel was transferred to a sterile 60 mL syringe that was capped with a syringe cap. 40 mL 0.9% sterile NaCl was added to the gel. The plunger was inserted into the syringe barrel and the syringe was inverted. The syringe cap was opened to release any pressure and was then closed. The syringe was inverted several time to ensure good mixing of the saline and the gel pieces. The gel was allowed to swell overnight (at least 16 hrs).

A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved. The syringe cap of the syringe was removed and the syringe filter containing the mesh was attached to the syringe. The gel was extruded through the mesh into a sterile 50 mL centrifuge tube. The centrifuge tube was capped with a screw top lid. The above steps were performed in a biohood.

Example 11

Preparation of HA-VS-PEG-(SH)$_2$ Gel Slurry Containing Triamcinolone Acetonide: Double Extrusion The triamcinolone acetonide-containing HA-VS/PEG-(SH)$_2$ gel (Example 9) was physically broken into pieces using a glass rod. The gel was transferred to a sterile 60 mL syringe that was capped with a syringe cap. 40 mL 0.9% sterile NaCl was added to the gel. The plunger was inserted into the syringe barrel and the syringe was inverted. The syringe cap was opened to release any pressure and was then closed. The syringe was inverted several time to ensure good mixing of the saline and the gel pieces. The gel was allowed to swell overnight (at least 16 hrs).

A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved. The syringe cap of the syringe was removed and the syringe filter containing the mesh was attached to the syringe. The gel was extruded through the mesh into a sterile 50 mL centrifuge tube. The extruded gel was then put into a sterile 60 mL syringe and the syringe filter that contained the mesh was attached to the syringe. The gel was extruded through the through the mesh into a sterile 50 mL centrifuge tube. The centrifuge tube was capped with a screw top lid. The above steps were performed in a biohood.

Example 12

Preparation of Syringes Containing Triamcinolone Acetonide Gel Slurry 5 mL of the prepared triamcinolone acetonide-containing HA-VS/PEG(SH)$_2$ gel slurry (Example 10 or Example 11) was transferred into a sterile 10 mL glass syringe (B&D) that had a syringe cap applied. A sterile stopper was inserted into the top of the syringe. A plunger rod was screwed into the stopper. The syringe was inverted and once the gel slurry had reached the stopper, the syringe cap was loosened slightly and the plunger was depressed until the majority of the air in the syringe was removed. The syringe cap was tightened. The above steps were performed in a biohood.

Example 13

Preparation of a Triamcinolone Acetonide Containing HA-VS/PEG-(SH)$_2$ Gel Slurry with Hyaluronic Acid 4

2 g hyaluronic acid [$9.4 \times 10^4$ cps (3% in water)] was weighed into a 250 mL round bottom flask. 100 mL sterile saline was added to, the hyaluronic acid in the flask. The flask was attached to a Rotavap (Buchi) and rotated at 50 rpm for at least 16 hrs to form a 2% hyaluronic acid solution. Using the HA-VS/PEG-(SH)$_2$ gel slurry containing triamcinolone acetonide (as prepared in Example 10 or 11), a series of formulations were prepared in which the a triamcinolone acetonide containing HA-VS/PEG-(SH)$_2$ gel slurry was mixed with hyaluronic acid. The volumes of hyaluronic acid solution and the triamcinolone acetonide-containing HA-VS/PEG-(SH)$_2$ gel slurry used to prepare these formulations are shown in the table below:

TABLE 3

| FORMULATION | VOLUME HYALURONIC ACID (ML) | VOLUME TRIAMCINOLONE ACETONIDE CONTAINING HA-VS/PEG-(SH)2 GEL SLURRY, (ML) |
|---|---|---|
| 1 | 1 | 5 (single extrusion slurry) |
| 2 | 2 | 4 (single extrusion slurry) |
| 3 | 3 | 3 (single extrusion slurry) |
| 4 | 4 | 2 (single extrusion slurry) |
| 5 | 5 | 1 (single extrusion slurry) |
| 6 | 1 | 5 (double extrusion slurry) |
| 7 | 2 | 4 (double extrusion slurry) |
| 8 | 3 | 3 (double extrusion slurry) |
| 9 | 4 | 2 (double extrusion slurry) |
| 10 | 5 | 1 (double extrusion slurry) |

The indicated volumes of hyaluronic acid solution and the triamcinolone acetonide-containing HA-VS/PEG-(SH)$_2$ gel slurry, as identified in the table above, were added to a 15 mL sterile centrifuge tube. The cap was placed on the tube and the tube was inverted back and forth until the components were well mixed. Each formulation was then transferred into a 10 mL glass syringe that had a syringe cap after which the plunger was inserted and the excess air was expelled. The syringe cap was then tightened. The above steps were performed in a biohood.

Example 14

Preparation of Samples for Release Study of Triamcinolone Acetonide 1.5 mL of the triamcinolone acetonide-containing HA-VS/PEG-(SH)$_2$ gel (prepared according to Example 11) was transferred to a 20 mL glass scintillation vial. 15 mL PBS (pH 7.4) was pipetted into the scintillation vial containing the gelled material. The scintillation vial was closed with a screw lid and the vial was placed on a rocking shaker (Barnstead International, Model M26125) in a 37° C. oven.

Example 15

Sampling of Release Study Buffer

At various time points, the scintillation vial that contained the triamcinolone acetonide-loaded gel and PBS buffer (as described in Example 14) was removed from the 37° C. oven. The residual gel slurry was allowed to settle to the bottom of the scintillation vial. The screw lid was removed and 13 mL of the PBS buffer was removed using a serological pipette and transferred into a 50 mL plastic centrifuge tube. 13 ml fresh PBS (pH 7.4) was then pipetted into the gel-containing scintillation vial.

Example 16

HPLC Analysis of the Triamcinolone Acetonide Containing Release Media

Figure 2:
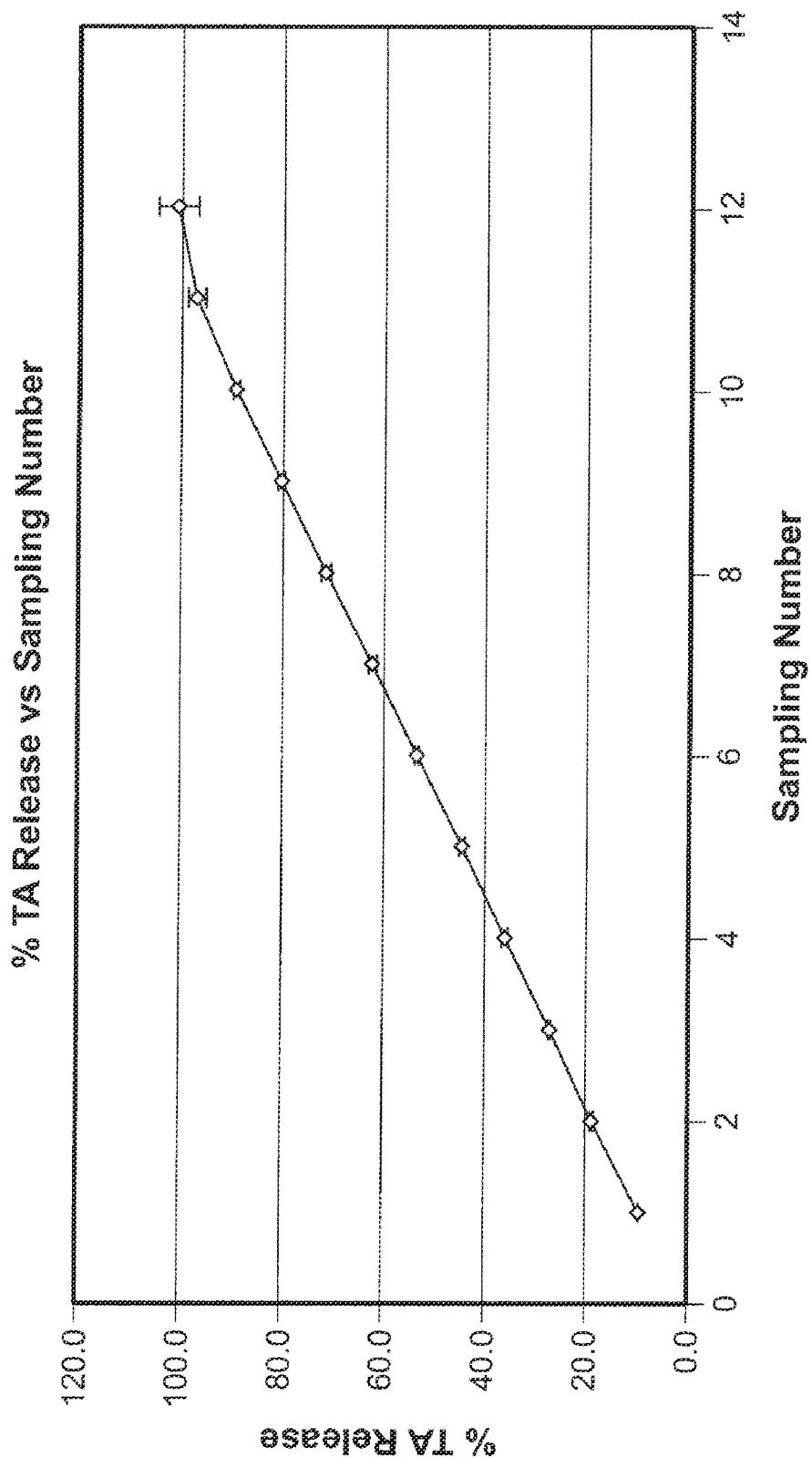
FIG. 2 is a plot demonstrating percent release of a poorly water soluble model drug, triamcinolone acetonide, versus sampling number as described in Example 16.
Figure 3:
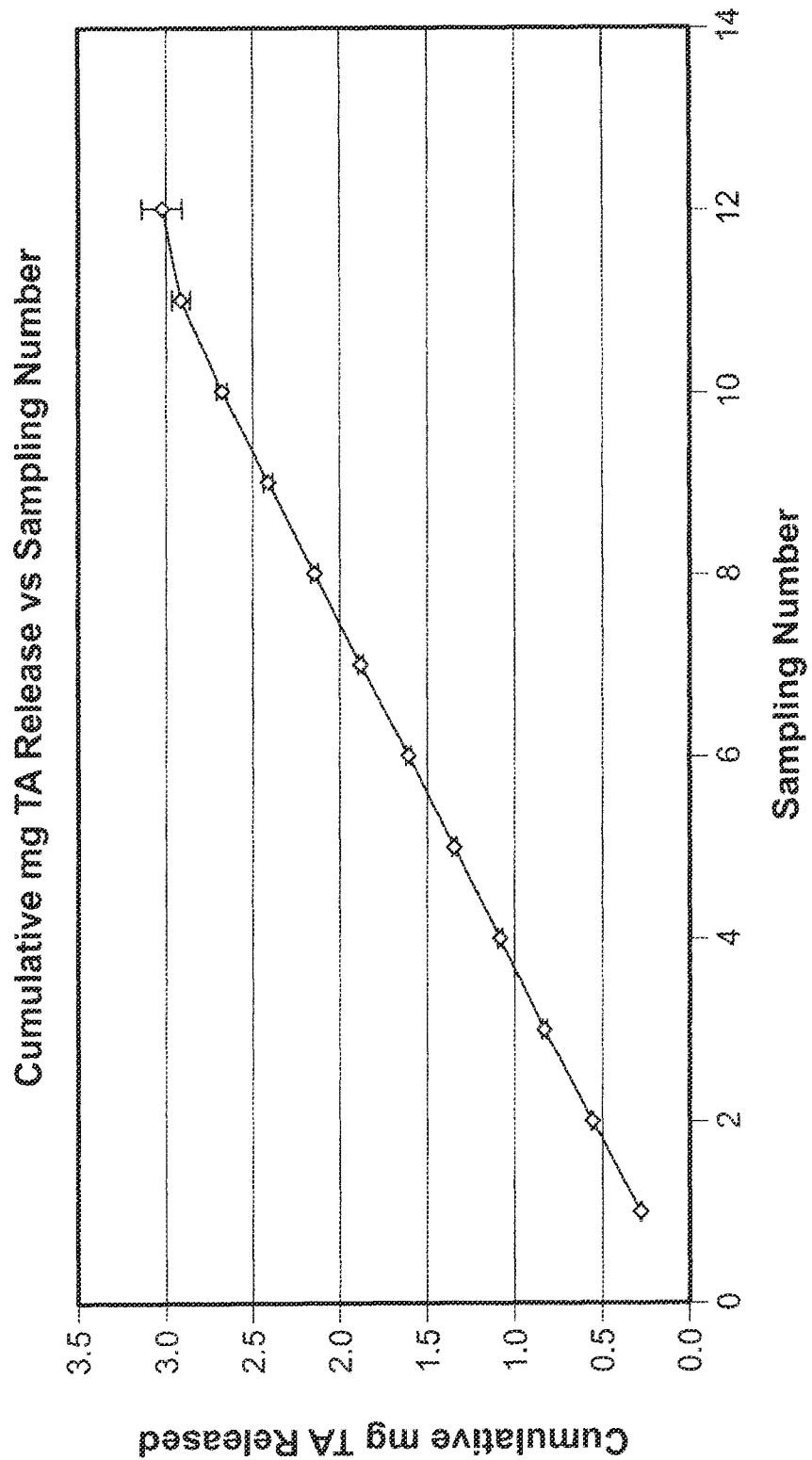
FIG. 3 is a plot demonstrating the cumulative mass released of a poorly water soluble model drug, triamcinolone acetonide, per sampling point as described in Example 16.
Figure 4:
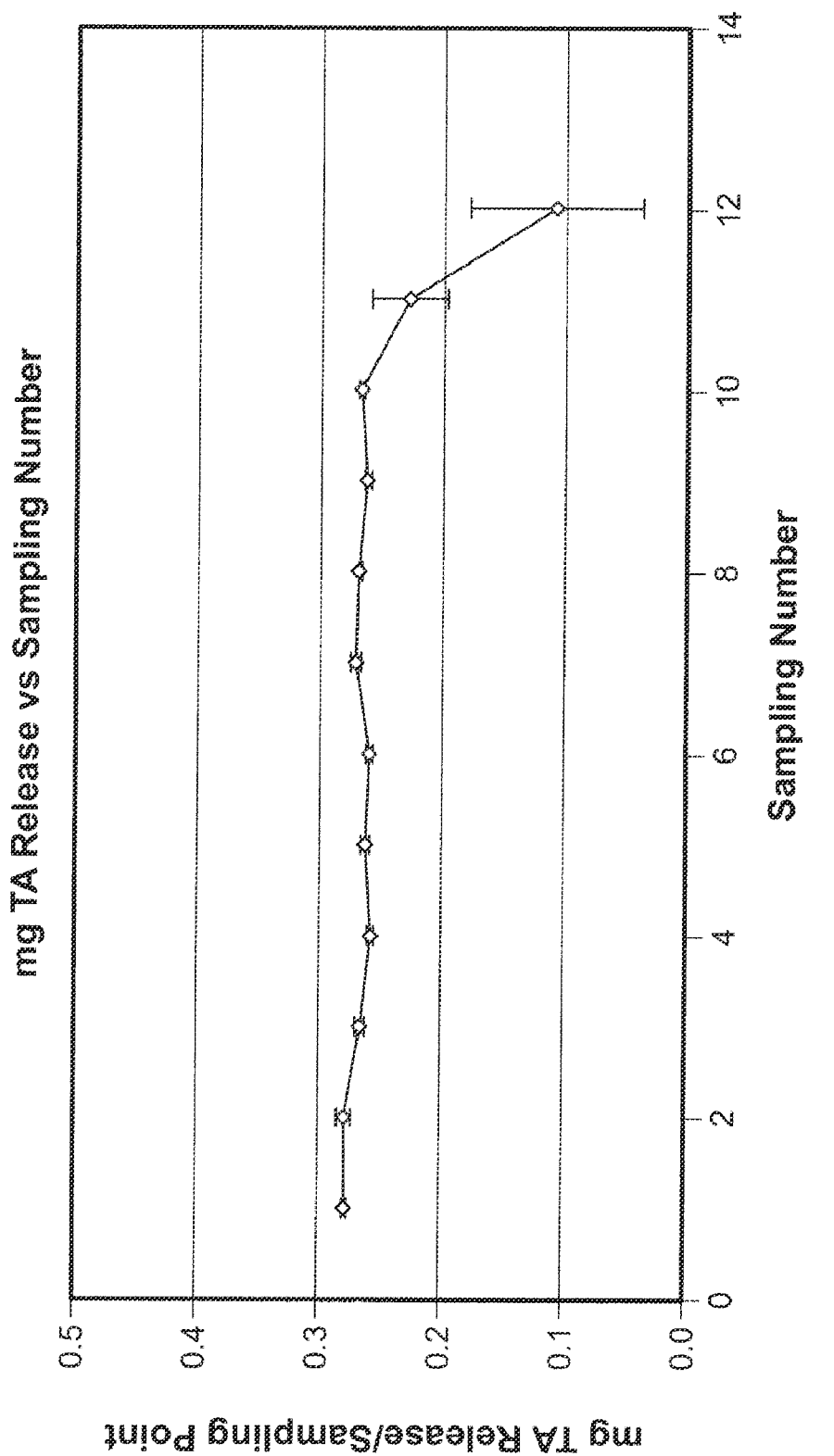
FIG. 4 is a plot demonstrating the amount of triamcinolone acetonide released per sampling point as described in Example 16.

The 13 mL buffer sample (Example 15) was diluted to 40 mL with 80:20 MeOH:H2O. The sample was vortexed and approx 1 mL was transferred to a HPLC vial. The triamcinolone acetonide content of the buffer sample was determined using the following chromatographic conditions: HPLC: Agilent 1100 series Column: Zorbax SB-C18, 5μ, 4.6×160 mm
Column Temperature: 30° C.
Flow rate: 1.0 mL/min
Detection: UV at 239 nm
Run Time: 8 minutes
Injection Volume: 50 μl
Mobile phase: 0.05% TFA in ACN: 0.05% TFA in H2O, 56:44
Retention Time of TA: ~3.3 min The amount of triamcinolone acetonide in the buffer samples was quantified by correlating the peak area to a triamcinolone acetonide concentration through a calibration curve. The samples for the triamcinolone acetonide calibration curves were prepared by taking a stock solution of triamcinolone acetonide in methanol and then serially diluting the stock solution with 0.05% TFA in ACN: 0.05% TFA in H$_2$O, 56:44. These samples were analyzed using the chromatographic conditions above and the peak area obtained was plotted against the triamcinolone acetonide concentration. The percent release is illustrated in FIG. 2; the cumulative mass released is shown in FIG. 3; and the amount release per sampling point is shown in FIG. 4.

Samples were drawn every 24 hours Monday-Friday; sampling was not conducted on Saturday/Sunday.

TABLE 4

| Sampling No. | Sampling Times (days) |
|---|---|
| 1 | 1 |
| 2 | 2 |
| 3 | 3 |
| 4 | 7 |
| 5 | 8 |
| 6 | 9 |
| 7 | 10 |
| 8 | 11 |
| 9 | 14 |
| 10 | 15 |

As shown in FIG. 2, essentially all drug was released by sampling point 12. Drug was released in a linear fashion over time, and in a controlled manner. Advantageously, essentially all drug was released rather than having a significant amount of drug remaining entrapped within the gel. Moreover, rather than releasing drug in an initial burst fashion, drug was released in a slow and sustained manner over time. FIG. 3 similarly illustrates cumulative release of drug, in milligrams, over sampling points. As illustrated in FIG. 4, the amount of drug released from the gel was essentially constant between sampling points, indicating a linear release of drug in a controlled and sustained manner over time.

Example 17

Intra-Articular Injection of an Exemplary HA-VS/PEG-(SH)$_2$ Gel Slurry

A sample of the HA-VS/PEG-(SH)$_2$ gel slurry (prepared as in Example 5) was injected intra-articularly into the stifle (knee) of skeletally mature female goats along with additional test materials 2-4 to provide points of reference. See also D. Jackson and T. Simon, Osteoarthritis and Cartilage, Vol. 14, Issue 12, p. 1248-125, for additional description related to the goat model used.

TEST MATERIAL 1: HA-VS/PEG-(SH)$_2$ gel (Example 5)
TEST MATERIAL 2: PEG diacrylate crosslinked with a bisthiol crosslinker
TEST MATERIAL 3: 4-arm lysine functionalized PEG that has been crosslinked to form a gel
TEST MATERIAL 4: gel made from PEG diacrylate (material was autoclaved)

See Examples 31-33 for preparations of Test Materials 2-4. All injections were performed under strict asepsis. The animals were anesthetized with an intravenous injection of diazepam (0.1-0.5 mg/kg) and ketamine (4.4-7.5 mg/kg) to effect. Each knee was physically examined for drawer, range of motion, swelling, temperature, crepitus, patella tracking, and valgus/varus abnormalities.

All injections were conducted utilizing routine aseptic techniques. The left and right stifles were prepared for injection by clipping the areas, then cleansing them with chlorohexidine scrub. The animal was placed in dorsal recumbency. The right stifle was cleansed with chlorohexidine scrub alternating with 70% isopropyl alcohol three times and painted with iodine solution.

A standard technique was used to inject each stifle joint. A 2-inch by 21 gauge sized sterile needle was introduced into the intra-articular space via an anteromedial approach. The lateral intercondylar notch wall of the medial femoral condyle was felt and the needle backed slightly off. 1.5 ml of the HA-VS/PEG(SH)$_2$ gel slurry was injected into the right joint. The injection needle was removed and pressure was maintained on the injection site. The injected stifle joint was then cycled 20-times through a full range of motion.

Post-injection checks were made for any animal displaying signs of distress and discomfort, and additional analgesics were given if needed. All treatments were recorded in the appropriate study documentation.

The injected animals were humanely sacrificed at 24±1 hours post initial injection with an intravenous injection consisting of diazepam 0.22 mg/kg and ketamine 10 mg/kg for induction of general anesthesia. Following this, the anesthetized animals were given an IV overdose of concentrated potassium chloride (KCl) until the cardiac arrest had been verified.

After collection of the knee joints, the joints were opened and gross evaluation as described in Table 5 of the injected stifle joints was performed. No photodocumentation was made.

TABLE 5

Gross Evaluation and Sample Collection

| Sample | Gross Evaluation | Sample collection | Score |
|---|---|---|---|
| Synovial Fluid (left and right) | X | X | X |
| Left and Right Knee joints | X |  | X |
| Left and Right synovium | X |  | X |

Additionally, semi-quantitative grading of the joint by a single observer as outlined in Table 6 was performed.

TABLE 6

Gross Joint Evaluation Grading Scale

| Score | Coloration | Hyperemia | Edema |
|---|---|---|---|
| 0 | Normal | None | None |
| 1 | Slightly yellow | Slight | Slight |
| 2 | Yellow | Moderate | Moderate |
| 3 |  | Marked | Marked |

The total joint gross evaluation score was the sum of the coloration, hyperemia, and edema scores (0-8 points). See FIG. 6.

After collection of the synovial fluid from the opened joints, the total volume was recorded. The fluid was grossly evaluated for viscosity, clarity and color and semi-quantitatively graded as per Table 7. With a hemocytometer, total white cell counts were done. Additionally, a synovial fluid smear was made for differential microscopic analysis.

Remaining synovial fluid was preserved frozen in individually labeled cryovials at −80° C. A synovial fluid smear was retained for potential future analysis.

TABLE 7

Description and Score for Synovial Fluid

| Score | Color | Clarity | String |
|---|---|---|---|
| 0 | S = STRAW | C = CLEAR | N = NORMAL |
| 1 | P = PINK | H = HAZY | A = ABNORMAL |
| 2 | Y = YELLOW/R = RED | D = CLOUDY | W = WATERY |
| 3 | B = BLOODY | T = TURBID |  |

Total synovial fluid score was the sum of the color, clarity and string scores (0-8 points).

Figure 5:
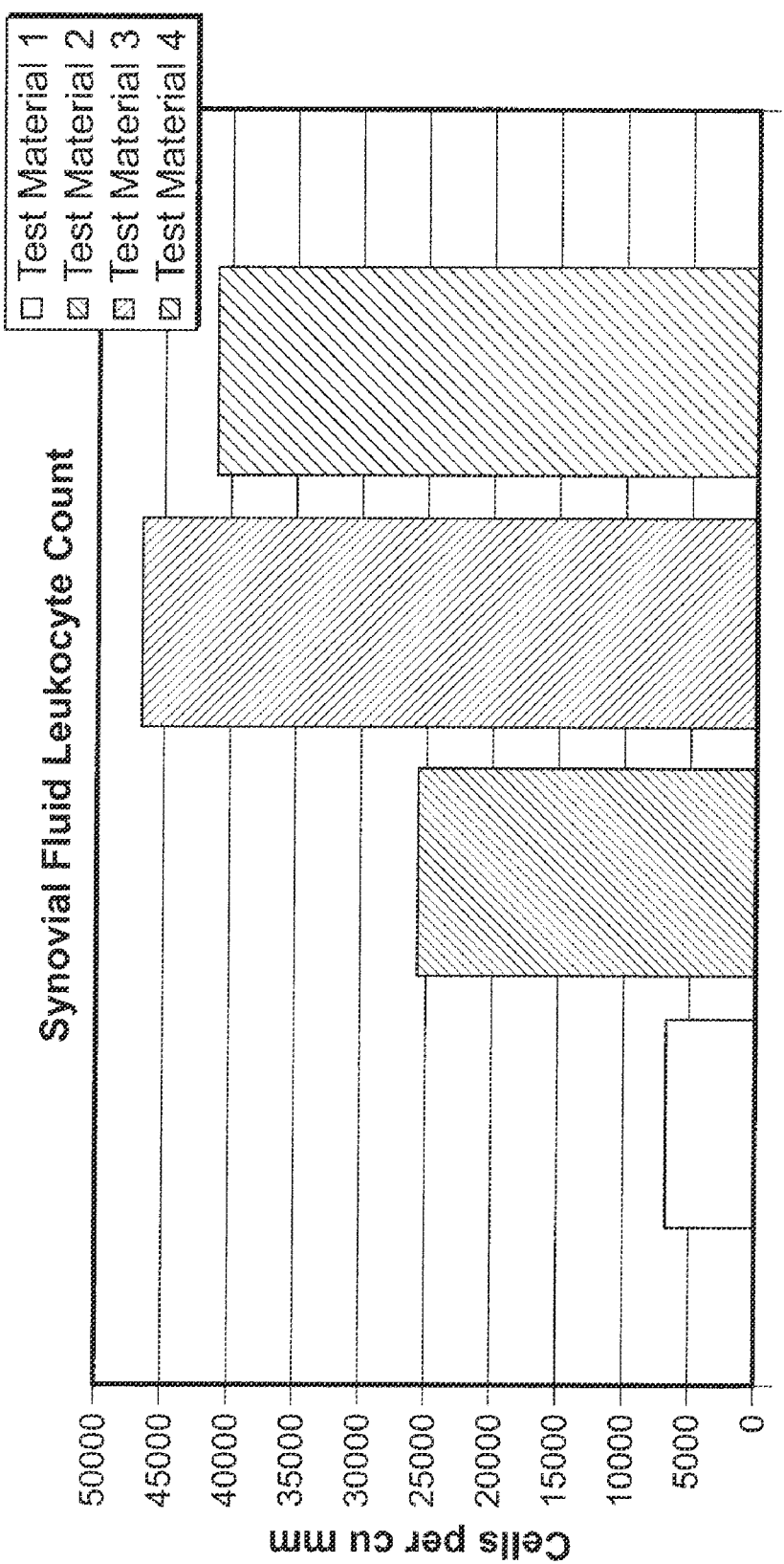
FIG. 5 is a graphical depiction of the synovial fluid leukocyte count (cells per cubic millimeter) in goat knees injected with Test Material 1 relative to the test material treatment group evaluated at 24 hrs after 1.5 ml injection as described in Example 17. Test Material 1=HA-VS/PEG-(SH)$_2$ gel.

Results are provided in graphical fashion in FIGS. 5-8. As can be seen in FIG. 5, an exemplary gel having the features described herein demonstrated a synovial fluid leukocyte count that was significantly lower than those observed for Test Materials 2-4. Indeed, the leukocyte counts for Test Materials 2-4 were approximately 5 times, 9 times and 8 times greater than observed for Test Material 1. While Test Materials 2-4 exhibit in-vitro behavior (e.g., chemistry, gel properties, ease of administration, etc.) indicating their suitability for pharmaceutical use, these results illustrate the clear superiority of Test Material 1 and materials similar thereto, in terms of having significantly low pro-inflammatory properties when examined in a goat model in comparison to seemingly comparable test materials. Surprisingly, all other indicators pointed to the suitability of the other test materials for viscosupplementation and other related uses.

Figure 6:
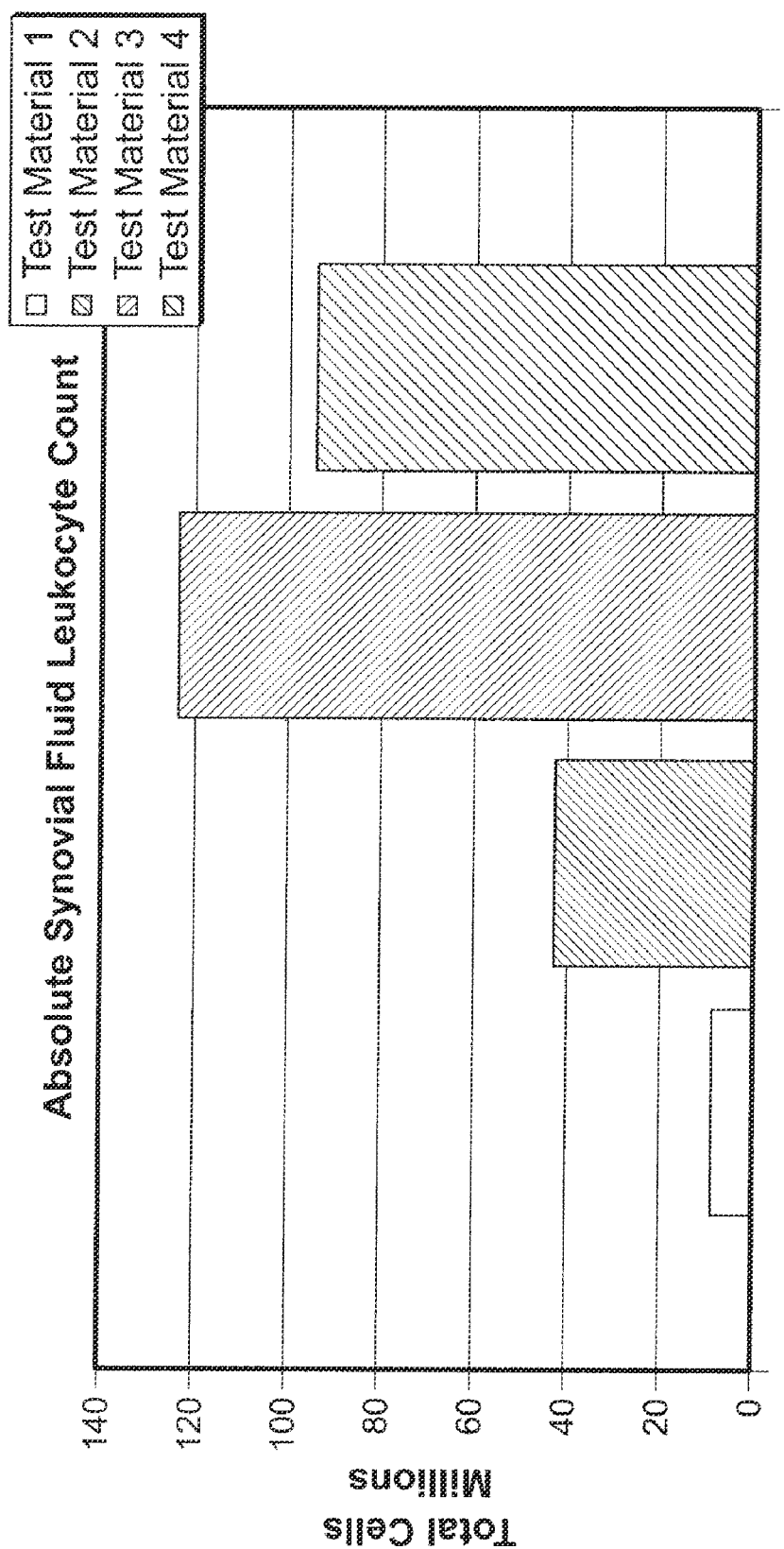
FIG. 6 is a graphical depiction of the absolute synovial fluid leukocyte count (absolute=total volume×synovial fluid leukocyte count) in goat knees injected with Test Material 1 relative to test material treatment group evaluated at 24 hrs after 1.5 ml injection as described in Example 17. Test Material 1=HA-VS/PEG-(SH)$_2$ gel.

FIG. 6, demonstrating absolute synovial fluid leukocyte count (absolute=total volume×synovial fluid leukocyte count) for the injected goat knees further supports the above.

That is, exemplary Test Material 1, demonstrates a strikingly lower inflammatory response in the goat model than do Test Materials 2-4, based upon absolute synovial fluid leukocyte count. Values for Test Materials 2-4 are approximately 4-fold, 12-fold, and over 9-fold greater than for Test Material 1—indicating the surprising and notable superiority of Test Material 1 when evaluated in the goat knee.

Figure 7:
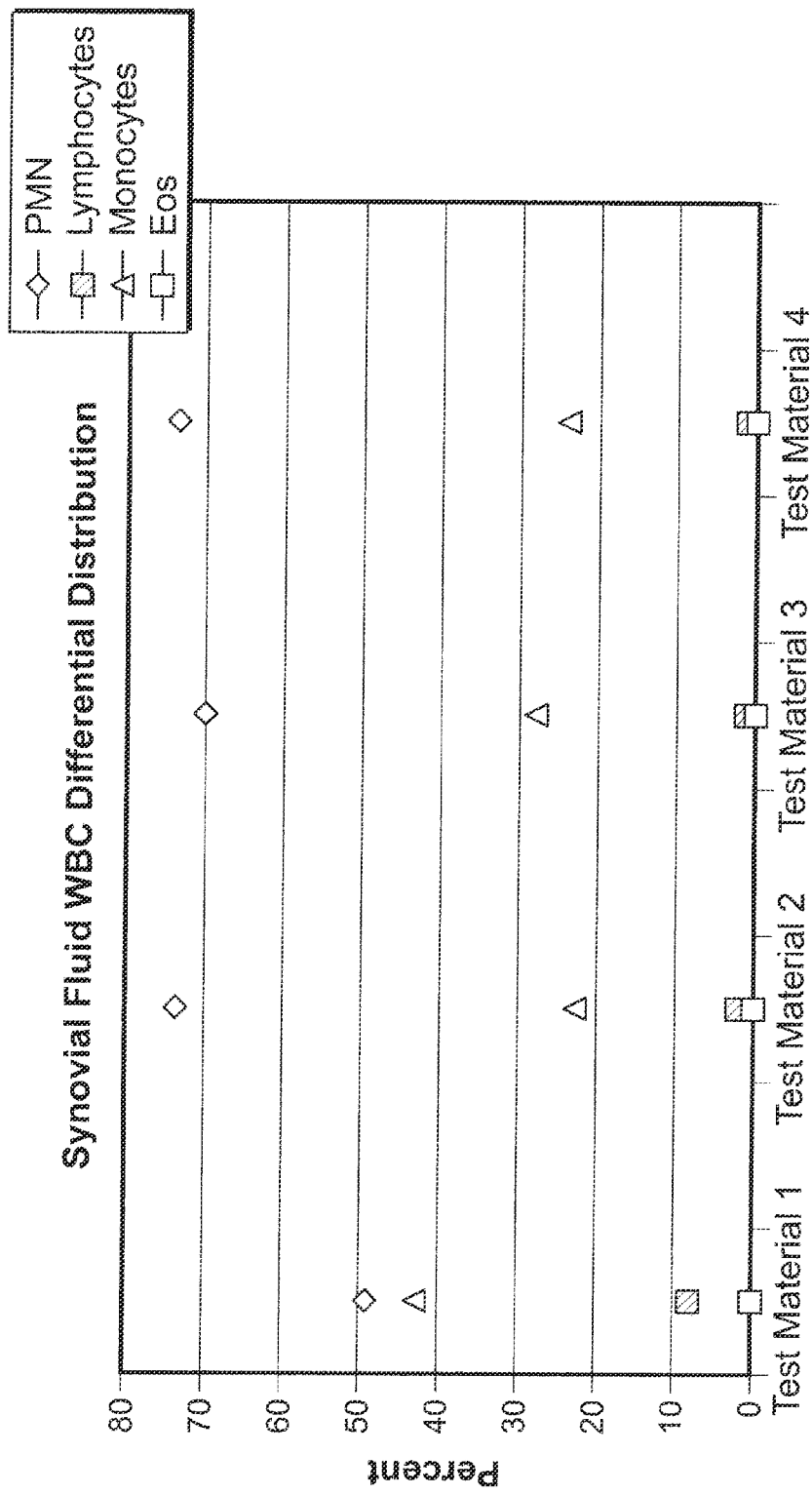
FIG. 7 provides a graphical representation of the synovial fluid leukocyte differential distribution (means for groups) for the injected goat knees relative to test material treatment group evaluated at 24 hrs after 1.5 ml injection as described in Example 17. Shown for each Test Material is the distribution of polymorphonuclear leukocytes (PMN), lymphocytes, monocytes, and eosinophils (Eos).

FIG. 7 is a graphical representation of the synovial fluid leukocyte differential distribution (means for groups) for the injected goat knees relative to test material treatment group evaluated at 24 hrs after 1.5 ml injection as described in Example 17. Shown for each Test Material is the distribution of polymorphonuclear leukocytes (PMN), lymphocytes, monocytes, and eosinophils (Eos). PMNs and Eos are important cellular participants in a variety of acute and chronic inflammation. The percentage of PMNs for Test Material 1 (relative to lympocytes, monocytes and eosinophils) was significantly lower than for other test materials (approx 50% relative to 70% and greater for test materials 2-4)—a yet additional indication of the advantageously low pro-inflammatory properties of exemplary Test Material 1 in comparison to the other materials examined.

Figure 8:
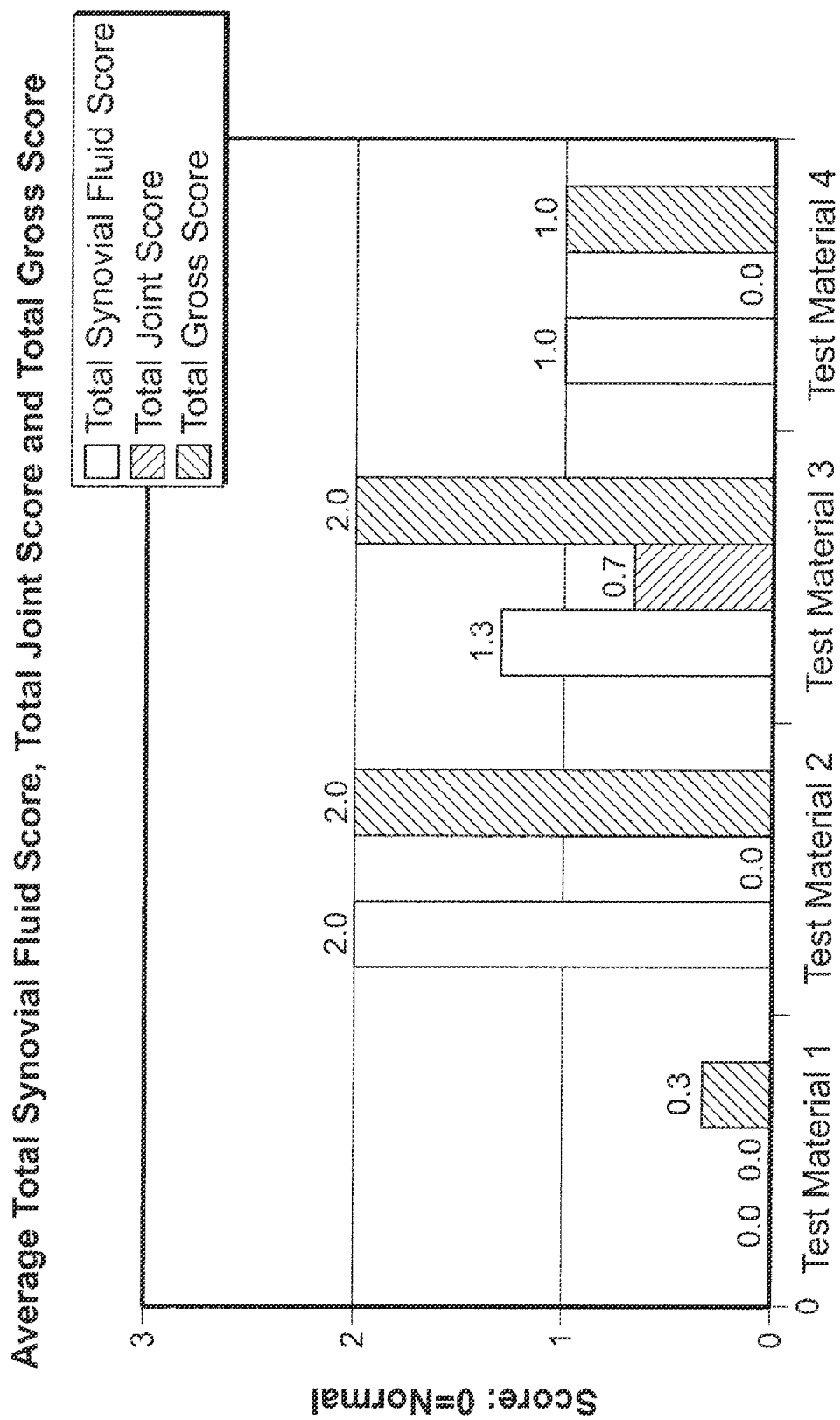
FIG. 8 is a graphical depiction of the average total scores for synovial fluid, joint tissues, and combined synovial fluid and joint tissues scores (Table 6) for the injected goat knees for each representative Test Material as described in Example 17, where Total Gross Score=Synovial Fluid Score+Total Joint Score. Maximum score for Synovial Fluid or Total Joint Score is 8 with 0 being normal; Maximum score for Total Gross Score is 16 with 0 being normal.

Finally, FIG. 8 illustrates the average total scores for synovial fluid, joint tissues, and combined synovial fluid and joint tissues scores (Table 6) for the injected goat knees for each representative Test Material.

Total Gross Score=Synovial Fluid Score+Total Joint Score.

Maximum score for Synovial Fluid or Total Joint Score is 8 with 0 being normal;

Maximum score for Total Gross Score is 16 with 0 being normal.

As illustrated in FIG. 8, a striking result is shown for Test Material 1. Indeed for all scores, determined by visual inspection as described above, Test Material 1 is shown to illicit essentially no inflammatory response, with scores for synovial fluid, joint tissues, and the combination considered to be normal or nearly normal. In contrast, representative Test Materials 2-4 resulted in visual characteristics in both the synovial fluid and joint that were non-normal, and indicated inflammation in the knee joint resulting from administration of the test material. These results demonstrate the surprising and beneficial properties of illustrative Test Material 1, in terms of suitability for therapeutic applications in-vivo.

Example 18

Synthesis of HA-VS/PEG-(SH)$_4$ Gel

A solution of the HA-VS, as prepared in Example 1, is diluted using deionized water to a concentration of 12.6 mg/mL. 18 mL HA-VS solution is placed into a 20 mL sterile syringe. The HA-VS solution is filtered through a 0.2 um sterile syringe filter into a sterile 50 mL centrifuge tube. 200 mg PEG(SH)$_4$, C(CH$_2$O(CH$_2$CH$_2$O)$_n$CH$_2$CH$_2$SH)$_4$, [Laysan Bio Inc, Mw 10,000, Item# 4armPEG-SH-10 kD-1 g] (e-beamed) is added to sterile filtered 2 mL 0.17M sodium phosphate in 1M saline (pH7.4). Once dissolved, the PEG-(SH)$_4$ solution is added to the HA-VS solution. The resultant solution is mixed thoroughly. The HA-VS/PEG-(SH)$_4$ solution is then allowed to gel at room temperature. The gelled material can be converted into a gel slurry in a similar manner to that described in Examples 3 and 4. The gel can be prepared in the presence of triamcinolone acetonide using a similar procedure to that described in Examples 9, 10 and 11. Hyaluronic acid can be added to the gel formulation in a similar procedure as that described in Example 8. Hyaluronic acid can be added to the triamcinolone acetonide gel formulation in a similar procedure as that described in Example 13.

Example 19

Synthesis of carboxymethyl-hyaluronic Acid (CM-HA or Carbylan™)

Aqueous NaOH solution (200 ml, 45% w/v) was added to a 500 mL beaker and was stirred (magnetic stirrer) at ambient temperature. Hyaluronic acid powder (20 g) [Novozymes, MW 0.8-1.0 million] was added to a 500-ml beaker. After standing for 2 hours, the hyaluronic acid mixture was transferred into a 4 L beaker with 1,500 ml isopropanol and a Teflon-coated magnetic stir bar, and then a solution of 20 g of chloroacetic acid in 500 ml isopropanol was added with magnetic stirring. After stirring for 1 hour at ambient temperature, the stirring was stopped and the material was allowed to settle for approx. 10-20 minutes. As much of the supernatant as possible was aspirated from the mixture. 1,000 ml of distilled water was added to the resultant mixture. Once dissolved, the solution pH was adjusted to ca. pH 7.0 by adding 6.0 N HCl. The solution is then made up to 2 L using DI water. The solution was purified by tangential flow filtration (TFF) using 10 L DI water as the exchange buffer.

Additionally, the structure, synthesis and characterization of carboxymethyl hyaluronic acid is described in International Patent Publication No. 2005/056608 (FIG. 5 and Example 3), related portions thereof are incorporated herein by reference in their entirety.

Example 20

Synthesis of Carboxymethyl-Hyaluronic Acid-Dithiobis(Propanoic Dihydrazide (CM-HA-DTPH or Carbylan™-S)

3,3'-Dithiobis (propanoic dihydrazide) (DTP) was synthesized as previously described. (Vercruysse, K. P.; Marecak, D. M.; Marecek, J. F.; Prestwich, G. D. "Synthesis and in vitro degradation of new polyvalent hydrazide cross-linked hydrogels of hyaluronic acid." Bioconjugate Chem. (1997) 8:686-694; Shu, X. Z.; Liu, Y.; Luo, Y.; Roberts, M. C.; Prestwich, G. D. "Disulfide crosslinked hyaluronan hydrogels." Biomacromolecules (2002) 3:1304-1311). DTP (16.7 g, 0.07 mol) was added to the Carbylan™ solution prepared above, and the solution pH was adjusted to 4.75 by adding either HCl or NaOH solution. Then, 0.384 g 1-ethyl-3[3-(dimethylamino) propyl]carbodiimide (EDC) [Sigma-Aldrich] was added, and the solution pH was maintained at a pH of 4.75 by adding 6.0 N HCl with continuous magnetic stirring at room temperature.

After 4 h, 50 g of dithiothreitol (DTT) [Biovectra] was added, and the solution pH was adjusted to 8.5 by adding conc. NaOH solution. Then after 12-24 h under magnetic stirring at room temperature, the pH of the reaction mixture was adjusted to pH 3.0 by the addition of 6.0 N HCl. The acidified solution was purified and concentrated using tangential fluid filtration (TFF) using 20 L 1 mM HCl, pH 3.0. The solution was then concentrated to approx The structure, synthesis, and characterization of carboxymethyl-hyaluronic acid-dithiobis(propanoic dihydrazide is described in International Patent Publication No. 2005/056608 (FIG. 5 and Example 4), related portions of which are incorporated herein by reference in their entirety.

Example 21

Synthesis of a CM-HA-DTPH/PEG-(Acrylate)$_2$ Gel

A solution of the CM-HA-DTPH, as prepared in Example 20, is diluted using deionized water to a concentration of 17.5 mg/mL. 30 mL CM-HA-DTPH solution is placed into a 60 mL sterile syringe. The CM-HA-DTPH solution is filtered through a 0.2 um sterile syringe filter into a sterile 50 mL centrifuge tube. A 40 mg/mL solution of PEG-(acrylate)2 [Laysan Bio Inc, MW 3400, Item# ACRL-PEG-ACRL3400-1 g] is prepared by dissolving 600 mg PEG-(acrylate)$_2$ in 15 mL 0.2M sodium phosphate buffer (pH 7.4). The PEG-(acrylate)$_2$ solution is transferred to a 20 mL sterile syringe and is filtered through a 0.2 um sterile syringe filter. 20 mL of the sterile filtered CM-HADTPH is transferred to a sterile 50 mL centrifuge tube. 10 mL of the PEG-(acrylate)$_2$ solution is added to the CM-HADTPH solution. The resultant solution is mixed thoroughly. The CM-HA-DTPH/PEG-(acrylate)$_2$ solution is then allowed to gel at room temperature.

Example 22

CM-HA-DTPH/PEG-(Acrylate)$_2$ Gel Slurry

The CM-HA-DTPH/PEG-(acrylate)$_2$ gel (as prepared in Example 21) is converted to a gel slurry using a procedure similar to that described in Examples 3 and 4 respectively.

Example 23

Triamcinolone Acetonide-Containing CM-HA-DTPH/PEG-(Acrylate)$_2$ Gel

A solution of the CM-HA-DTPH, as prepared in Example 20, is diluted using deionized water to a concentration of 14 mg/mL. 11 mL CM-HA-DTPH solution is placed into a 20 mL sterile syringe. The CM-HA-DTPH solution is filtered through a 0.2 um sterile syringe filter into a sterile 50 mL centrifuge tube. A 50 mg/mL solution of PEG-(acrylate)$_2$ [Laysan Bio Inc, MW 3400, Item# ACRL-PEG-ACRL-3400-1 g] is prepared by dissolving 40.1 mg PEG-(acrylate)$_2$ in 0.802 mL deionized water. The PEG-(acrylate)$_2$ solution is transferred to a 1 mL sterile syringe and is filtered through a 0.2 um sterile syringe filter. 10 mL of the sterile filtered CM-HA-DTPH is transferred to a sterile 50 mL centrifuge tube. 20 mg of triamcinolone acetonide (Spectrum Chemicals, U.S.P grade, micronized) was added to the CM-HA-DTPH solution. The cap of the centrifuge tube was placed on the tube and the solution was inverted back and forth until the triamcinolone acetonide was homogeneously mixed with the CM-HA-DTPH. 250 µL of a 0.5 M sodium phosphate solution is added to the CM-HA-DTPH solution. The resultant solution is mixed thoroughly. 380 µL [19 mg PEG-(acrylate)$_2$] of the sterile 50 mg/mL PEG-(acrylate)$_2$ solution is added to the CM-HA-DTPH solution. The resultant solution is mixed thoroughly. The CM-HA-DTPH/PEG-(acrylate)$_2$ solution that contained triamcinolone acetonide is then placed in a 37° C. incubator for at least 16 hours. At this stage the CM-HA-DTPH/PEG-(acrylate)$_2$ solution that contained triamcinolone acetonide is crosslinked to form a gel. The gelled material is then removed from the incubator.

The synthesis of the gel is repeated using 33 mg, 50 mg, 75 mg, 100 mg, 125 mg, 150 mg, 175 mg, 200 mg, 225 mg, 250 mg, 375 mg, 400 mg and 500 mg triamcinolone acetonide respectively.

The gels were converted into a gel slurry using a similar procedure to that described in Example 3 and 4.

Example 24

Synthesis Of Triamcinolone Acetonide-Containing HA-VS-PEG-(SH)$_2$ Gel Slurry Triamcinolone acetonide-containing HA-VS-PEG-(SH)$_2$ gels are prepared using a procedure similar to that described in Example 9 with the exception that 33 mg, 50 mg, 75 mg, 100 mg, 125 mg, 150 mg, 175 mg, 200 mg, 225 mg, 250 mg, 375 mg, 400 mg and 500 mg triamcinolone acetonide, respectively, were used to prepare each gel.

The gels were converted into a gel slurry using a similar procedure to that described in Example 3 and 4.

Example 25

Synthesis of a CM-HA-DTPH/PEG-(Acrylate)$_4$ Gel

A solution of the CM-HA-DTPH, as prepared in Example 20, is diluted using deionized water to a concentration of 14 mg/mL. 11 mL CM-HA-DTPH solution is placed into a 20 mL sterile syringe. The CM-HA-DTPH solution is filtered through a 0.2 um sterile syringe filter into a sterile 50 mL centrifuge tube. A 50 mg/mL solution of PEG-(acrylate)$_4$ [Laysan Bio Inc, Mw 10,000, Item# 4arm-PEG-ACRL10K-1 g] is prepared by dissolving 40.1 mg PEG-(acrylate)$_4$ in 0.802 mL deionized water. The PEG-(acrylate)$_4$ solution is transferred to a 1 mL sterile syringe and was filtered through a 0.2 um sterile syringe filter. 10 mL of the sterile filtered CM-HADTPH is transferred to a sterile 50 mL centrifuge tube. 250 µL of a 0.5 M sodium phosphate solution is added to the CM-HA-DTPH solution. The resultant solution is mixed thoroughly. 560 µL [28 mg PEG-(acrylate)$_4$] of the sterile 50 mg/mL PEG-(acrylate)$_4$ solution is added to the CM-HA-DTPH solution. The resultant solution is mixed thoroughly. The CM-HA-DTPH/PEG-(acrylate)$_4$ solution is then placed in a 37° C. incubator for at least 16 hours. At this stage the CM-HA-DTPH/PEG-(acrylate)$_4$ solution is crosslinked to form a gel. The gelled material is then removed from the incubator. The gelled material can be converted into a gel slurry in a similar manner as to that described in Example 3 and 4. The gel can be prepared in the presence of triamcinolone acetonide using a similar procedure to that described in Examples 9, 10 and 11. Hyaluronic acid can be added to the gel formulation in a similar procedure as that described in Example 8. Hyaluronic acid can be added to the triamcinolone acetonide gel formulation in a similar procedure as that described in Example 13.

Example 26

Synthesis Of Hyaluronic Acid-Dithiobis(Propanoic Dihydrazide (HA-DTPH)

3,3'-Dithiobis (propanoic dihydrazide) (DTP) was synthesized as described previously. (Vercruysse, K. P.; Marecak, D. M.; Marecek, J. F.; Prestwich, G. D. "Synthesis and in vitro degradation of new polyvalent hydrazide cross-linked hydrogels of hyaluronic acid." *Bioconjugate Chem.* (1997) 8:686-694; Shu, X. Z.; Liu, Y.; Luo, Y.; Roberts, M. C.; Prestwich, G. D. "Disulfide crosslinked hyaluronan hydrogels." *Biomacromolecules* (2002) 3:1304-1311). DTP (16.7 g, 0.07 mol) was added to a hyaluronic acid (20 g hyaluronic acid [Mw 0.8-1.0 million] dissolved in 1000 mL DI water) solution prepared above, and the solution pH was adjusted to 4.75 by adding either HCl or NaOH solution. Then, 0.384 g 1-Ethyl-3-[3 (dimethylamino) propyl]carbodiimide (EDC) [Sigma-Aldrich] was added, and the solution pH was maintained at a pH of 4.75 by adding 6.0 N HCl with continuous magnetic stirring at room temperature. After 4 h, 50 g of dithiothreitol (DTT) [Biovectra] was added, and the solution pH was adjusted to 8.5 by adding conc. NaOH solution. Then after 12-24 h under magnetic stirring at room temperature, the pH of the reaction mixture was adjusted to pH 3.0 by the addition of 6.0 N HCl. The acidified solution was purified and concentrated using tangential fluid filtration (TFF) using 20 L 1 mM HCl, pH 3.0. The solution was then concentrated to approx 1 L.

Example 27

Synthesis of a HA-DTPH/PEG-(Acrylate)$_2$ Gel

A solution of the HA-DTPH, as prepared in Example 26, is diluted using deionized water to a concentration of 14 mg/mL. 11 mL HA-DTPH solution is placed into a 20 mL sterile syringe. The HA-DTPH solution is filtered through a 0.2 um sterile syringe filter into a sterile 50 mL centrifuge tube. A 50 mg/mL solution of PEG-(acrylate)$_2$ [Laysan Bio Inc, MW 3400, Item# ACRL-PEG-ACRL-3400-1 g] is prepared by dissolving 40.1 mg PEG-(acrylate)$_2$ in 0.802 mL deionized water. The PEG-(acrylate)$_2$ solution is transferred to a 1 mL sterile syringe and is filtered through a 0.2 um sterile syringe filter. 10 mL of the sterile filtered HA-DTPH is transferred to a sterile 50 mL centrifuge tube. 250 µL of a 0.5 M sodium phosphate solution is added to the HA-DTPH solution. The resultant solution is mixed thoroughly. 380 µL [19 mg PEG-(acrylate)$_2$] of the sterile 50 mg/mL PEG-(acrylate)$_2$ solution is added to the HA-DTPH solution. The resultant solution is mixed thoroughly. The HA-DTPH/PEG-(acrylate)$_2$ solution is then placed in a 37° C. incubator for at least 16 hours. At this stage the HA-DTPH/PEG-(acrylate)$_2$ solution is crosslinked to form a gel. The gelled material is then removed from the incubator.

Example 28

HA-DTPH/PEG-(Acrylate)$_2$ Gel Slurry

The HA-DTPH/PEG-(acrylate)$_2$ gel (as prepared in Example 27) is converted to a gel slurry using a procedure similar to that described in Examples 3 and 4, respectively.

Example 29

Triamcinolone Acetonide Containing HA-DTPH/PEG-(Acrylate)$_2$ Gel

A solution of the CM-HA-DTPH, as prepared in Example 20, is diluted using deionized water to a concentration of 17.5 mg/mL. 30 mL CM-HA-DTPH solution is placed into a 60 mL sterile syringe. The CM-HA-DTPH solution is filtered through a 0.2 um sterile syringe filter into a sterile 50 mL centrifuge tube. 100 mg sterile triamcinolone acetonide powder is added and the resultant mixture is mixed thoroughly. A 40 mg/mL solution of PEG-(acrylate)$_2$ [Laysan Bio Inc, MW 3400, Item# ACRL-PEG-ACRL3400-1 g] is prepared by dissolving 600 mg PEG-(acrylate)$_2$ in 15 mL 0.2M sodium phosphate buffer (pH 7.4). The PEG-(acrylate)$_2$ solution is transferred to a 20 mL sterile syringe and is filtered through a 0.2 um sterile syringe filter. 20 mL of the sterile filtered CM-HADTPH is transferred to a sterile 50 mL centrifuge tube. 10 mL of the PEG-(acrylate)$_2$ solution is added to the CM-HA-DTPH solution. The resultant solution is mixed thoroughly. The CM-HA-DTPH/PEG-(acrylate)$_2$ solution is then allowed to gel at room temperature.

The synthesis of the gel is repeated using 33 mg, 50 mg, 75 mg, 125 mg, 150 mg, 175 mg, 200 mg, 225 mg, 250 mg, 375 mg, 400 mg and 500 mg triamcinolone acetonide, respectively.

The gels are converted into a gel slurry using a similar procedure to that described in Example 3 and 4.

Example 30

Synthesis of a HA-DTPH/PEG-(ACRYLATE)$_4$ Gel

A solution of the HA-DTPH, as prepared in Example 20, is diluted using deionized water to a concentration of 14 mg/mL. 11 mL HA-DTPH solution is placed into a 20 mL sterile syringe. The HA-DTPH solution is filtered through a 0.2 um sterile syringe filter into a sterile 50 mL centrifuge tube. A 50 mg/mL solution of PEG-(acrylate)$_4$ [Laysan Bio Inc, Mw 10,000, Item# 4arm-PEG-ACRL-10K-1 g] is prepared by dissolving 40.1 mg PEG-(acrylate)$_4$ in 0.802 mL deionized water. The PEG-(acrylate)$_4$ solution is transferred to a 1 mL sterile syringe and was filtered through a 0.2 um sterile syringe filter. 10 mL of the sterile filtered HA-DTPH is transferred to a sterile 50 mL centrifuge tube. 250 µL of a 0.5 M sodium phosphate solution is added to the HA-DTPH solution. The resultant solution is mixed thoroughly. 560 µL [28 mg PEG-(acrylate)$_4$] of the sterile 50 mg/mL PEG-(acrylate)$_4$ solution is added to the HA-DTPH solution. The resultant solution is mixed thoroughly. The HA-DTPH/PEG-(acrylate)$_4$ solution is then placed in a 37° C. incubator for at least 16 hours. At this stage the HA-DTPH/PEG-(acrylate)$_4$ solution is crosslinked to form a gel. The gelled material is then removed from the incubator. The gelled material can be converted into a gel slurry in a similar manner as to that described in Example 3 and 4. The gel can be prepared in the presence of triamcinolone acetonide using a similar procedure as to that described in Example 9, 10 and 11. Hyaluronic acid can be added to the gel formulation in a similar procedure as that described in Example 8. Hyaluronic acid can be added to the triamcinolone acetonide gel formulation in a similar procedure as that described in Example 13.

Example 31

Preparation of Peg-Diacrylate Gel

Test Material 4

1.466 g of Poly(ethylene glycol)-diacrylate [PEG-DA] (Laysan Bio, Item# ACRL-PEG-ACRL-3400-1 g) was weighed into a sterile 125 mL bottle. 22 mL of sterile saline was added to the PEG-DA. Once dissolved, the PEG-DA/NaCl was filtered through a 0.2 um syringe filter into sanitized Erlenmeyer flask. A 0.150M Carbonate Buffer, pH 8.2 was filtered through a 0.2 um syringe filter and 1 mL of this sterile solution was added to PEG-DA solution. The flask was capped with a rubber septum and the solution was degassed by bubbling with nitrogen for 10 minutes. A 0.2 um filter is attached to the gas line to ensure the air is sterile. A 400 mg/mL sodium ascorbate solution was prepared by adding 1.2 g sodium ascorbate into a scintered glass vial with a septum lid. 3 mL DI water was added to the vial. Once dissolved, the solution was filtered through 0.2 um syringe filter into a 15 ml sterile centrifuge tube. 0.8 mL of sterile filtered 400 mg/mL sodium ascorbate was added to the PEG-DA solution. 0.8 of a sterile filtered 400 mg/mL sodium persulfate solution was added to the PEG-DA solution. The solution was mixed by swirling the solution. The flask was capped with red rubber septa and the solution was degassed by bubbling with nitrogen for 15 minutes. A 0.2 um filter was attached to the gas line to ensure the nitrogen used to degas the solution. The solution was placed in a 37° C. for at least 18 hrs to form a gel. The gel was transferred to a 30 mL syringe. A 23 mm circular disk of the mesh was cut from a sheet of mesh using a 23 mm leather punch. The mesh disk was placed into a 25 mm polycarbonate syringe filter that has the support screens removed. The gel was extruded through a mesh (1 mm×1 mm openings) into a 250 mL beaker. 100 mL sterile saline was added to 25 mL of the extruded gel. After 40 min, the saline supernatant was poured off and an additional 125 mL sterile saline was added. This was repeated 3 times. After the final wash, 45 ml of the swollen gel was added to 45 mL saline and the slurry was gently mixed. The pH of the resultant solution was adjusted to between 7.0 and 7.4 using a combination of 1N NaOH and 1 N HCl. 1.5 mL of the this gel slurry was filled into a 5 mL glass syringe. A syringe cap was used to close the syringe. The syringe was then autoclaved at 250° C. for 15 min.

Example 32

Preparation of Peg-Diacrylate/Bisthiol Gel

Test Material 2

630 mg Poly(ethylene glycol)-diacrylate [PEG-DA] (Laysan Bio, Item# ACRL-PEG-ACRL-3400-1 g) was weighed into a 20 mL glass scintillation vial. 6 mL DI water was added. Once dissolved, the solution was filtered trough a 0.2 um syringe filter. 48 mg N,N'-Bis(acryloyl)cystamine (Sigma, A4929) was dissolved in 6 mL tetrahydrofuran (THF) in a glass scintillation vial. Once dissolved this solution was mixed with the PEG-DA solution. A septum screw cap was placed on the vial and the solution was degassed by bubbling with nitrogen for 10 minutes. 50 uL of a 400 mg/mL solution of sodium ascorbate (prepared using DI water and filtered through a 0.2 um syringe filter) was added to the PEG-DA solution. 50 uL of a 400 mg/mL solution of sodium persulfate (prepared using DI water and filtered through a 0.2 um syringe filter) was added to the PEG-DA solution. The septum lid was replaced and the solution was degassed by bubbling with nitrogen for 10 minutes. The solution was placed in an oven that was set at 60° C. The solution had turned into a gel after 15 minutes. The gel was removed from the oven and was allowed to cool to room temperature. The gel was transferred to a 30 mL syringe. A 23 mm circular disk of the mesh was cut from a sheet of mesh using a 23 mm leather punch. The mesh disk was placed into a 25 mm polycarbonate syringe filter that has the support screens removed. The gel was extruded through a mesh (~0.8 mm×~0.8 mm openings) into a 400 mL beaker. 200 mL DI water was added to the extruded gel. After 45 min, the supernatant was poured off and an additional 200 mL DI water was added. This was repeated 4 times. The wash steps were then repeated 3 times using 0.9% saline. The supernatant liquid was removed and the remaining gel was extruded through the mesh again (as described above). 1.5 mL of the this gel slurry was filled into a 5 mL glass syringe. A syringe cap was used to close the syringe. The syringe was then autoclaved at 250° C. for 15 min.

Example 33

Preparation of PEG-(LYS)$_4$ Gel

Test Material 3

1.0 g of a PEG-(lys)4 [a 4-arm polyethylene glycol (Mw 10,000) that has its terminal hydroxyl groups functionalized with gutarice anhydride and then with lysine] was weighed into a 60 mL glass bottle. 34 mL dichloromethane was added to the PEG-(lys)4. 333 uL of diisopropylcarbodiimide (Fluka, 38370) was added to the solution. The solution had changed to a gel after about 30 minutes. The gelation was allowed to continue for at least 18 hrs. The gel was transferred to a 30 mL syringe. A 23 mm circular disk of the mesh was cut from a sheet of mesh using a 23 mm leather punch. The mesh disk was placed into a 25 mm polycarbonate syringe filter that has the support screens removed. The gel was extruded through a mesh (~0.38 mm×~0.38 mm openings) into a 400 mL beaker. 33 mL of the gel was washed 330 mL acetone. After 30 min, the acetone was removed. The wash process was repeated 4 times. The gel was then dried under vacuum (Approx. 18 hr under vacuum). 771 mg of the dried gel was added to 52 mL saline and the gel was allowed to swell for 5 hrs. The gel was then meshed through a mesh (~0.38 mm×~0.38 mm openings). 1.5 mL of the this gel slurry was filled into a 5 mL glass syringe. A syringe cap was used to close the syringe. The syringe was then autoclaved at 250° C. for 15 min.

Example 34

In-Vivo Study: Intra-Articular Injection Of A Crosslinked HA-VS-PEG-(SH)$_2$ Hydrogel Containing a Corticosteroid A lightly crosslinked hydrogel prepared by reaction of vinyl-sulfone-modified hyaluronic acid with PEG-dithiol (HA-VS-PEG-(SH)$_2$), containing the corticosteroid, triamcinolone acetonide, was injected into the intraarticular space of the stifle joint of female goats. Morphological, synovial fluid and histological examinations were conducted to evaluate local and systemic effects of such injections. Details of the study are provided below.

A. Test Materials

Test Material 1. HA-VS-PEG-(SH)$_2$ (cross-linked HA-based hydrogel absent drug) was prepared as follows.

A solution of the HA-VS, prepared as in Example 1, was diluted using deionized water to a concentration of 14 mg1 mL. 11 mL HA-VS solution was placed into a 20 mL sterile syringe. The HA-VS solution was filtered through a 0.2 um sterile syringe filter into a sterile 20 mL syringe. A 50 mg/mL solution of PEG(SH)$_2$ was prepared by dissolving 40.1 mg PEG-(SH)$_2$ in 0.802 mL deionized water. The PEG-(SH)$_2$ solution was transferred to a 3 mL sterile syringe and was filtered through a 0.2 µm sterile syringe filter. 10 mL of the sterile filtered HA-VS was transferred to a sterile 50 mL centrifuge tube. 250 uL of a 0.5 M sodium phosphate solution was added to the HA-VS solution. The resultant solution was mixed thoroughly. 380 mL of the sterile 50 mg/mL PEG-(SH)$_2$ solution was added to the HA-VS solution. The resultant solution was mixed thoroughly. The HA-VS/PEG-(SH)$_2$ solution was then placed in a 37° C. incubator for at least 16 hours. At this stage the HA-VS/PEG-(SH)$_2$ solution had crosslinked to form a gel. The gelled material was then removed from the incubator.

Test Material 2. HA-VS-PEG-(SH)$_2$-triamcinolone acetonide ("HA-VS-PEG(SH)$_2$-TA") was prepared as follows.

100.2 mg of triamcinolone acetonide (Sicor, U.S.P grade, micronized) was mixed in 2 mL deionized water in a 20 mL scintillation vial. After sonicating for 20 minutes, the material was autoclaved at 250'F for 15 minutes. 9 mL of the HA-VS solution, prepared as in Example 1 at concentration of 18.3 mg/mL was placed into a 20 mL sterile syringe. The HA-VS solution was filtered through a 0.2 µm sterile syringe filter into a sterile 10 mL syringe. A 50 mg/mL solution of PEG-(SH)$_2$ was prepared by dissolving 35 mg PEG-(SH)$_2$ in 0.7 mL deionized water. The PEG(SH)$_2$ solution was transferred to a 3 mL sterile syringe and was filtered through a 0.2 um sterile syringe filter. 7.6 mL of the sterile filtered HA-VS was transferred to the triamcinolone acetonide solution. 370 µl deionized water and 250 uL of a 0.5 M sodium phosphate solution was added to the vial containing HA-VS and triamcinolone acetonide. The resultant solution was mixed thoroughly. 380 µL of the sterile 50 mglmL PEG-(SH)$_2$ solution was added to the HA-VS/triamcinolone acetonide solution. The resultant solution was mixed thoroughly. The HAVS/triamcinolone acetonide/PEG-(SH)$_2$ solution was then placed in a 37° C. incubator for at least 16 hours. At this stage the HA-VS-PEG-(SH)$_2$-TA solution had crosslinked to form a gel. The gelled material was then removed from the incubator.

Test Material 3. Triamcinolone acetonide, 2 mg/ml (Kenalog-10; 10 mg/mL triamcinolone acetonide diluted with saline to 2 mg/mL)

Test Material 4. Triamcinolone acetonide, 8 mg/ml (Kenalog-40; 40 mg/mL triamcinolone acetonide diluted with saline to 8 mg/mL)

Control. Saline, 0.9% sodium chloride.

All test materials were stored at room temperature prior to use. For each Test or Control Material, a 1.5 ml dosage was prepared for each individual intra-articular injection.

B. Animals

A total of 24 skeletally mature female goats were used for this study. They were acquired from an approved USDA source. Animals weighed between 63 and 97 lbs at the start of the study.

Goats were acquired from an approved USDA source and determined to be Caprine Arthritis Encephalitis (CAE) and Johne's negative prior to being placed in this study. Each animal was given a general health evaluation (subject to visual observation for attitude, ease in respiration, and freedom from diarrhea and nasal discharge) by a qualified veterinarian prior to being placed in the study. The animals were examined for any evidence of disease or lameness. Acceptability into the study was contingent on being disease free, clinically sound, and no history of prior use of the stifle joint. The goats were conditioned for an appropriate period of time as determined by the institution. Animal housing conditions conformed with applicable laws and regulations relating to laboratory animals. The goats were maintained in large indoor runs (pens) following injection. The goats had unrestricted activity at all times.

All animals received approximately 2 lbs. of small ruminant diet per day as well as loose hay. Tap water was provided ad libitum. Feed was withheld approximately 12-24 hours prior to anesthesia and water was withheld approximately 12 hours prior to injections.

Animals were observed daily for general health throughout the course of the study. If animals showed any signs of postoperative complications or other signs of disease, pain or stress, appropriate action was taken. Also, in the unlikely event that an animal became injured, ill, or moribund, care was conducted in accordance with current veterinary medical practice.

C. Treatment

Study design was as follows.

TABLE 8

Group and Treatment Assignment

| Group | Ear Tag | Right Stifle (1.5 ml) | Left Stifle (1.5 ml) | Sacrifice Time after Right Stifle Injection, Left Stifle Injection |
|---|---|---|---|---|
| 1 | 3171 | Test Material 1 | Normal Saline | 14 days |
| 1 | 3256 | Test Material 1 | Normal Saline | 14 days |
| 1 | 3831 | Test Material 1 | Normal Saline | 14 days |
| 2 | 3174 | Test Material 2 | Normal Saline | 14 days |
| 2 | 3596 | Test Material 2 | Normal Saline | 14 days |
| 2 | 3840 | Test Material 2 | Normal Saline | 14 days |
| 3 | 3133 | Test Material 3 | Normal Saline | 14 days |
| 3 | 3177 | Test Material 3 | Normal Saline | 14 days |
| 3 | 3833 | Test Material 3 | Normal Saline | 14 days |
| 4 | 3589 | Test Material 4 | Normal Saline | 14 days |
| 4 | 3593 | Test Material 4 | Normal Saline | 14 days |
| 4 | 3849 | Test Material 4 | Normal Saline | 14 days |
| 5 | 3267 | Test Material 1 | Normal Saline | 28 days |
| 5 | 3595 | Test Material 1 | Normal Saline | 28 days |
| 5 | 3837* | Test Material 1 | Normal Saline | 28 days (24 days*) |
| 6 | 3173 | Test Material 2 | Normal Saline | 28 days |
| 6 | 3264 | Test Material 2 | Normal Saline | 28 days |
| 6 | 3587 | Test Material 2 | Normal Saline | 28 days |
| 7 | 3591 | Test Material 3 | Normal Saline | 28 days |
| 7 | 3592 | Test Material 3 | Normal Saline | 28 days |
| 7 | 3594 | Test Material 3 | Normal Saline | 28 days |
| 8 | 3162 | Test Material 4 | Normal Saline | 28 days |
| 8 | 3588* | Test Material 4 | Normal Saline | 28 days (19 days*) |
| 8 | 3590 | Test Material 4 | Normal Saline | 28 days |

*animal died prematurely; (total days on study).

Bodyweight, joint circumference and range of motion measurements were taken from all animals prior to injection (Day 1) and just prior to sacrifice (Day 14 or 28) for each animal.

The basic procedure for injection was identical for all subjects. All injections were performed under strict asepsis. The animals were anesthetized with an intravenous injection of Diazepam (0.1-0.5 mg/kg) and Ketamine (4.4-7.5 mg/kg) to effect. Each knee was physically examined for drawer, range of motion, swelling, temperature, crepitus, patella tracking, and valgus/varus abnormalities All injections were conducted utilizing routine aseptic techniques. The left and right stifles were prepared for injection by clipping the areas, then cleansing them with chlorohexidine scrub. The animal was placed in dorsal recumbency. The right stifle was cleansed with chlorohexidine scrub alternating with 70% isopropyl alcohol three times and painted with iodine solution.

A standard technique was used to inject each stifle joint. A 2-inch by 21gauge sized sterile needle was introduced into the intra-articular space via an anteromedial approach. The lateral intercondylar notch wall of the medial femoral condyle was felt and the needle backed slightly off. 1.5 ml of the appropriate Test Material was injected into the right joint. The injection needle was removed and pressure was maintained on the injection site. The injected stifle joint was then cycled 20-times through a full range of motion. Immediately following this, the left stifle joint was cleansed with chlorohexidine scrub alternating with 70% isopropyl alcohol three times and painted with iodine solution and 1.5 ml of the Control Material was injected into the left stifle joint in a similar manner as described above for the right stifle. The injection needle was removed and pressure maintained on the injection site. The injected stifle joint was then cycled 20-times through a full range of motion.

Post-injection checks were made for any animal displaying signs of distress and discomfort, and additional analgesics were given if needed. All treatments were recorded in the appropriate study documentation.

D. Analysis

Blood Collection: Blood was collected from each animal just prior to the start of the study, and at 5 hours post-injection and at days 1, 4, 7, 14 and 28 from each of the remaining animals. CBC and blood chemistry panels were run at each time point.

Necropsy: Animals were humanely sacrificed at either 14 days or 28 days day post initial injection with an intravenous injection consisting of Diazepam 0.22 mg/kg and Ketamine 10 mg/kg for induction of general anesthesia. Following this, the anesthetized animals were given an IV overdose of concentrated potassium chloride (KCl) until the cardiac arrest had been verified.

Gross Morphological Observations: After collection of the knee joints, the joints were opened and gross evaluation as described in Table 2 of the injected stifle joints was done.

TABLE 9

Gross Evaluation and Sample Collection

| Sample | Gross Evaluation | Sample Collection | Photograph and Score |
|---|---|---|---|
| Synovial Fluid (left and right) | X | X | |
| Left and Right Knee joints | X | | X |
| Left and Right posterior synovial pouch | X | X | X |
| Left and Right cartilage Sample | X | X | X |
| Left and Right popliteal lymph node | X | X | X |

Additionally, semi-quantitative grading of the joint by a single observer as outline in Table 3 was performed.

TABLE 10

Gross Evaluation Grading Scale

| Score | Coloration | Hyperemia | Edema |
|---|---|---|---|
| 0 | Normal | None | None |
| 1 | Slightly yellow | Slight | Slight |
| 2 | Yellow | Moderate | Moderate |
| 3 | | Marked | Marked |

The total joint gross evaluation score was the sum of the coloration, hyperemia, and edema scores (0-8 points).

Synovial Fluid Evaluation

After collection of the synovial fluid from the opened joints, the total volume was recorded. The fluid was grossly evaluated for viscosity, clarity and color and semi-quantitatively graded as per Table 11. With a hemocytometer, total white cell counts were done. Additionally, a synovial fluid smear was made for differential microscopic analysis. Any remaining synovial fluid was preserved frozen in individually labeled cryovials at −80° C. A synovial fluid smear was retained for potential future analysis.

TABLE 11

Description and Score for Synovial Fluid

| Score | Color | Clarity | String |
|---|---|---|---|
| 0 | S = STRAW | C = CLEAR | N = NORMAL |
| 1 | P = PINK | H = HAZY | A = ABNORMAL |
| 2 | Y = YELLOW/R = RED | D = CLOUDY | W = WATERY |
| 3 | B = BLOODY | T = TURBID | |

Total synovial fluid score is the sum of the color, clarity and string scores (08 points).

Histological Evaluation:

Immediately after dissection and following gross joint surface evaluation a sagital section of each joint was cut through the medial femoral condyle (MFC). These sections were placed individually in 10% neutral buffered formalin. The fixed tissue was shipped by overnight carrier to Premier Laboratories for processing. The right and left MFC sections were processed using standard histological techniques and stained with hematoxylin and eosin (H&E) and Safranin-O (SAF-O) with a fast green counter stain. The slides from the MFC sections were evaluated by the Mankin Scoring System for osteoarthritis as described in Table 12.

TABLE 12

Modified Mankin Scoring System

| | |
|---|---|
| Structure | Normal [0] |
| | Surface Irregularities [1] |
| | Pannus & Surface Irregularities [2] |
| | Clefts to Transitional Zone [3] |
| | Clefts to Radial Zone [4] |
| | Clefts to Calcified Zone [5] |
| | Complete Disorganization [6] |
| Cells | Normal [0] |
| | Diffuse Hypercellularity [1] |
| | Cloning [2] |
| | Hypocellularity [3] |
| Safranin-O Staining | Normal [0] |
| | Slight Reduction [1] |
| | Moderate Reduction [2] |
| | Severe Reduction [3] |
| | No Dye Noted [4] |
| Tidemark Integrity | Intact [0] |
| | Crossed By Blood Vessels [1] |
| Maximal Score | 14 (Normal = 0) |

E. Results

Figure 9:
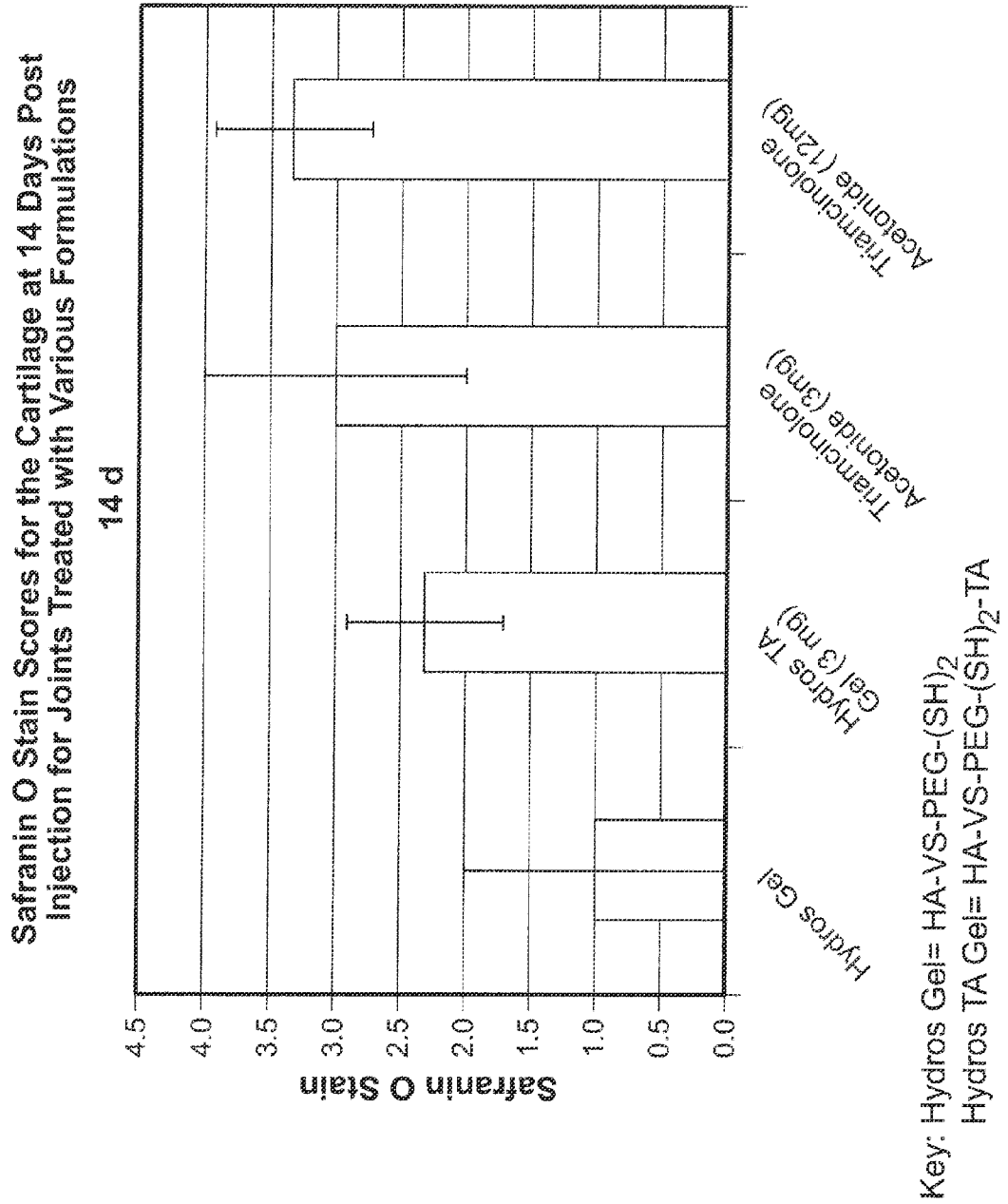
FIG. 9 illustrates the safranin O stain scores for cartilage samples from goat joints treated with the test materials as described in detail in Example 34 at 14 days post injection. Test Material 1: HA-VS-PEG-(SH)$_2$, Test Material 2: HA-VS-PEG-(SH)$_2$-TA.
Figure 10:
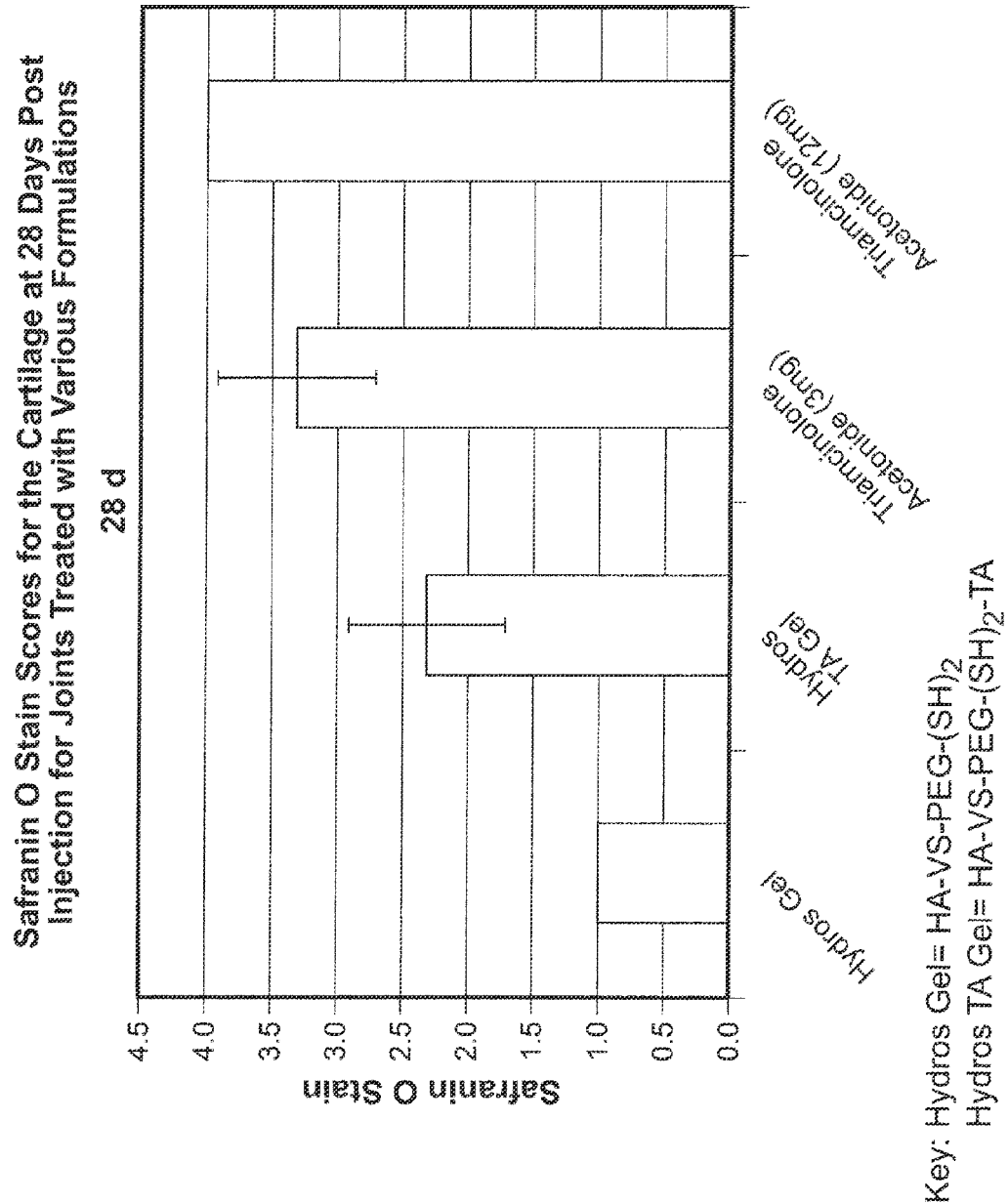
FIG. 10 illustrates the safranin O stain scores for cartilage samples from goat joints treated with the test materials as described in detail in Example 34 at 28 days post injection.
Figure 11:
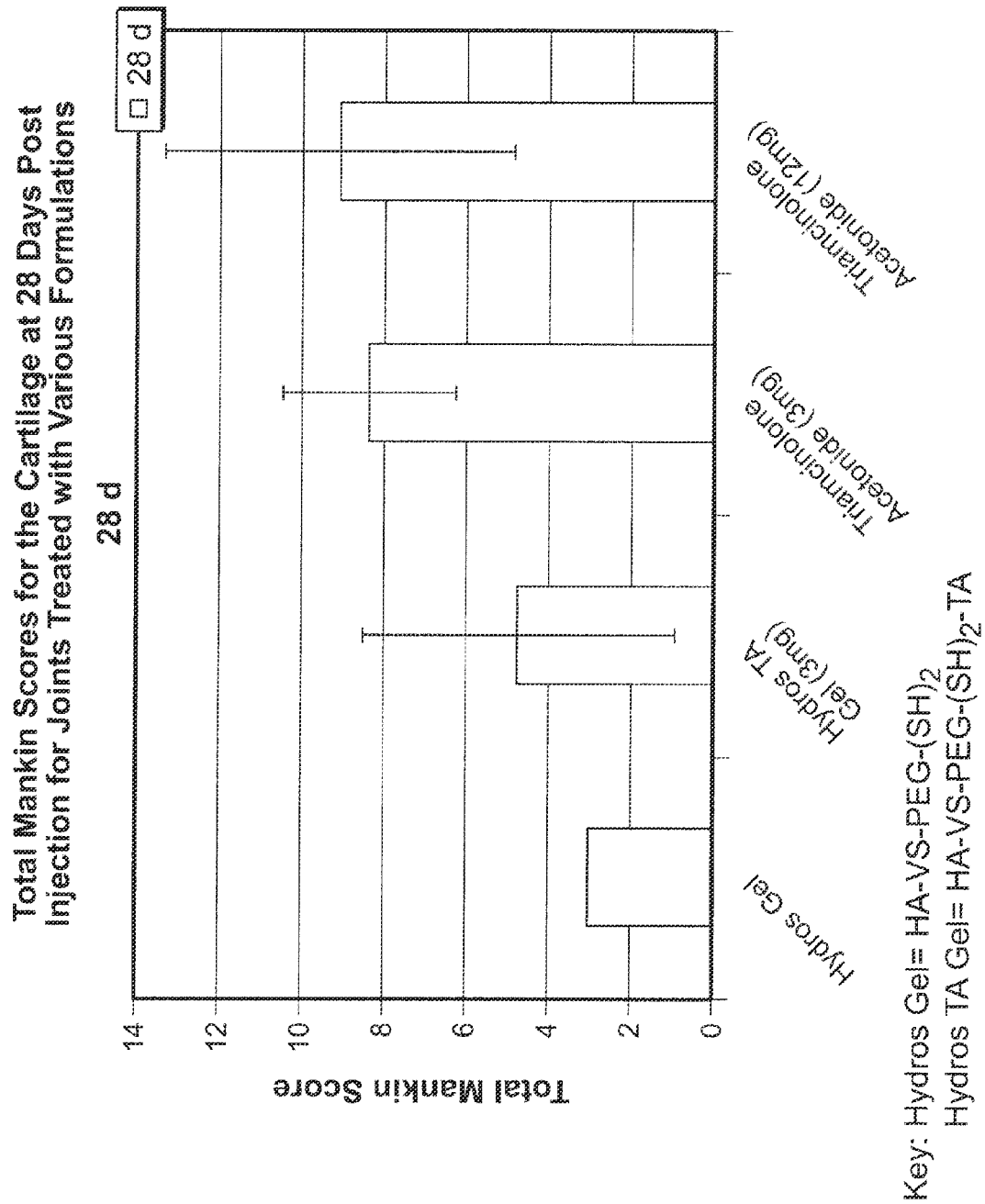
FIG. 11 illustrates the results of the Mankin scoring systems for cartilage samples from goat joints treated with the test materials as described in detail in Example 34 at 28 days post-treatment.

The results of the Mankin scoring systems for the cartilage samples for the joints treated with the various formulations are shown in Tables 13a-h and are shown in FIG. 11. FIGS. 9 (14 Days post-treatment) and 10 (28 Days posttreatment) show the safranin O stain score for cartilage samples for the joints treated with the various formulations at 14 and 28 Days post-treatment respectively.

TABLE 13a

Mankin Score of Femoral Cartilage at 14 day evaluation, Group 1

| Sample | Treatment | Structure | Cells | Safranin-O Stain | Tide Mark Integrity | Total Mankin Score |
|---|---|---|---|---|---|---|
| 3256 RFC | HA-VS Gel | 5 | 3 | 2 | 0 | 10 |
| 3171 RFC | HA-VS Gel | 4 | 1 | 0 | 0 | 5 |
| 3831 RFC | HA-VS Gel | 0 | 0 | 1 | 0 | 1 |

TABLE 13a-continued

Mankin Score of Femoral Cartilage at 14 day evaluation, Group 1

| Sample | Treatment | Structure | Cells | Safranin-O Stain | Tide Mark Integrity | Total Mankin Score |
|---|---|---|---|---|---|---|
| MEAN | | 3.0 | 1.3 | 1.0 | 0.0 | 5.3 |
| SD | | 2.6 | 1.5 | 1.0 | 0.0 | 4.5 |
| 3256 LFC | 0.9% NaCl | 4 | 1 | 2 | 0 | 7 |
| 3171 LFC | 0.9% NaCl | 4 | 1 | 0 | 0 | 5 |
| 3831 LFC | 0.9% NaCl | 0 | 0 | 1 | 0 | 1 |
| MEAN | | 2.7 | 0.7 | 1.0 | 0.0 | 4.3 |
| SD | | 2.3 | 0.6 | 1.0 | 0.0 | 3.1 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13b

Mankin Score of Femoral Cartilage at 14 day evaluation, Group 2

| Sample | Treatment | Structure | Cells | Safranin-O Stain | Tide Mark Integrity | Total Mankin Score |
|---|---|---|---|---|---|---|
| 3840 RFC | HA-VS/TA Gel | 3.0 | 1.0 | 2.0 | 0.0 | 6.0 |
| 3596 RFC | HA-VS/TA Gel | 0.0 | 0.0 | 3.0 | 0.0 | 3.0 |
| 3174 RFC | HA-VS/TA Gel | 4.0 | 2.0 | 2.0 | 0.0 | 8.0 |
| MEAN | | 2.3 | 1.0 | 2.3 | 0.0 | 5.7 |
| SD | | 2.1 | 1.0 | 0.6 | 0.0 | 2.5 |
| 3840 LFC | 0.9% NaCl | 3.0 | 1.0 | 0.0 | 0.0 | 4.0 |
| 3596 LFC | 0.9% NaCl | 0.0 | 0.0 | 1.0 | 0.0 | 1.0 |
| 3174 LFC | 0.9% NaCl | 4.0 | 2.0 | 2.0 | 0.0 | 8.0 |

TABLE 13b-continued

Mankin Score of Femoral Cartilage at 14 day evaluation, Group 2

| Sample | Treatment | Structure | Cells | Safranin-O Stain | Tide Mark Integrity | Total Mankin Score |
|---|---|---|---|---|---|---|
| MEAN | | 2.3 | 1.0 | 1.0 | 0.0 | 4.3 |
| SD | | 2.1 | 1.0 | 1.0 | 0.0 | 3.5 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild focal to Multifocal Hypocellularity [1]
Mild focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13c

Mankin Score of Femoral Cartilage at 14 day evaluation, Group 3

| Sample | Treatment | Structure | Cells | Safranin-O Stain | Tide Mark Integrity | Total Mankin Score |
|---|---|---|---|---|---|---|
| 3833 RFC | Triamcinolone Acetonide 2mg/ml | 4.0 | 1.0 | 3.0 | 0.0 | 8.0 |
| 3133 RFC | Triamcinolone Acetonide 2mg/ml | 0.0 | 0.0 | 4.0 | 0.0 | 4.0 |
| 3177 RFC | Triamcinolone Acetonide 2mg/ml | 4.0 | 1.0 | 2.0 | 0.0 | 7.0 |
| MEAN | | 2.7 | 0.7 | 3.0 | 0.0 | 6.3 |
| SD | | 2.3 | 0.6 | 1.0 | 0.0 | 2.1 |
| 3833 LFC | 0.9% NaCl | 0.0 | 0.0 | 1.0 | 0.0 | 1.0 |
| 3133 LFC | 0.9% NaCl | 0.0 | 0.0 | 2.0 | 0.0 | 2.0 |
| 3177 LFC | 0.9% NaCl | 0.0 | 0.0 | 1.0 | 0.0 | 1.0 |

TABLE 13c-continued

Mankin Score of Femoral Cartilage at 14 day evaluation, Group 3

| Sample | Treatment | Structure | Cells | Safranin-O Stain | Tide Mark Integrity | Total Mankin Score |
|---|---|---|---|---|---|---|
| MEAN | | 0.0 | 0.0 | 1.3 | 0.0 | 1.3 |
| SD | | 0.0 | 0.0 | 0.6 | 0.0 | 0.6 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13d

Mankin Score of Femoral Cartilage at 14 day evaluation, Group 4

| Sample | Treatment | Structure | Cells | Safranin-O Stain | Tide Mark Integrity | Total Mankin Score |
|---|---|---|---|---|---|---|
| 3593 RFC | Triamcinolone Acetonide 8mg/ml | 0.0 | 0.0 | 4.0 | 0.0 | 4.0 |
| 3849 RFC | Triamcinolone Acetonide 8mg/ml | 5.0 | 1.0 | 3.0 | 0.0 | 9.0 |
| 3589 RFC | Triamcinolone Acetonide 8mg/ml | 0.0 | 0.0 | 3.0 | 0.0 | 3.0 |
| MEAN | | 1.7 | 0.3 | 3.3 | 0.0 | 5.3 |
| SD | | 2.9 | 0.6 | 0.6 | 0.0 | 3.2 |
| 3593 LFC | 0.9% NaCl | 0.0 | 0.0 | 2.0 | 0.0 | 2.0 |
| 3849 LFC | 0.9% NaCl | 1.0 | 1.0 | 2.0 | 0.0 | 4.0 |
| 3589 LFC | 0.9% NaCl | 0.0 | 0.0 | 3.0 | 0.0 | 3.0 |

TABLE 13d-continued

Mankin Score of Femoral Cartilage at 14 day evaluation, Group 4

| Sample | Treatment | Structure | Cells | Safranin-O Stain | Tide Mark Integrity | Total Mankin Score |
|---|---|---|---|---|---|---|
| MEAN | | 0.3 | 0.3 | 2.3 | 0.0 | 3.0 |
| SD | | 0.6 | 0.6 | 0.6 | 0.0 | 1.0 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization
Normal [0]
Mild Focal to Multifocal Hypocellularity [1]
Mild Focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13e

Mankin Score of Femoral Cartilage at 28 day evaluation, Group 5

| Sample | Treatment | Structure | Cells | Safranin-O Stain | Tide Mark Integrity | Total Mankin Score |
|---|---|---|---|---|---|---|
| 3267 RFC | HA-VS Gel | 1 | 1 | 1 | 0 | 3 |
| 3837 RFC* | HA-VS Gel | 3 | 1 | 3 | 0 | 7 |
| 3595 RFC | HA-VS Gel | 1 | 1 | 1 | 0 | 3 |
| MEAN | | 1.0 | 1.0 | 1.0 | 0.0 | 3.0 |
| SD | | 0.0 | 0.0 | 0.0 | 0.0 | 0.0 |
| 3267 LFC | 0.9% NaCl | 1 | 1 | 1 | 0 | 3 |
| 3837 LFC* | 0.9% NaCl | 3 | 1 | 3 | 0 | 7 |
| 3595 LFC | 0.9% NaCl | 1 | 1 | 2 | 0 | 4 |

TABLE 13e-continued

Mankin Score of Femoral Cartilage at 28 day evaluation, Group 5

| Sample | Treatment | Structure | Cells | Safranin-O Stain | Tide Mark Integrity | Total Mankin Score |
|---|---|---|---|---|---|---|
| MEAN | | 1.0 | 1.0 | 1.5 | 0.0 | 3.5 |
| SD | | 0.0 | 0.0 | 0.7 | 0.0 | 0.7 |

*Animal died prematurely. Data recorded but not included in averages.

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13f

Mankin Score of Femoral Cartilage at 28 day evaluation, Group 6

| Sample | Treatment | Structure | Cells | Safranin-O Stain | Tide Mark Integrity | Total Mankin Score |
|---|---|---|---|---|---|---|
| 3264 RFC | HA-VS/TA Gel | 0.0 | 0.0 | 3.0 | 0.0 | 3.0 |
| 3587 RFC | HA-VS/TA Gel | 5.0 | 2.0 | 2.0 | 0.0 | 9.0 |
| 3173 RFC | HA-VS/TA Gel | 0.0 | 0.0 | 2.0 | 0.0 | 2.0 |
| MEAN | | 1.7 | 0.7 | 2.3 | 0.0 | 4.7 |
| SD | | 2.9 | 1.2 | 0.6 | 0.0 | 3.8 |
| 3264 LFC | 0.9% NaCl | 0.0 | 0.0 | 0.0 | 0.0 | 0.0 |
| 3587 LFC | 0.9% NaCl | 5.0 | 2.0 | 1.0 | 0.0 | 8.0 |
| 3173 LFC | 0.9% NaCl | 0.0 | 0.0 | 1.0 | 0.0 | 1.0 |

TABLE 13f-continued

Mankin Score of Femoral Cartilage at 28 day evaluation, Group 6

| Sample | Treatment | Structure | Cells | Safranin-O Stain | Tide Mark Integrity | Total Mankin Score |
|---|---|---|---|---|---|---|
| MEAN | | 1.7 | 0.7 | 0.7 | 0.0 | 3.0 |
| SD | | 2.9 | 1.2 | 0.6 | 0.0 | 4.4 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13g

Mankin Score of Femoral Cartilage at 28 day evaluation, Group 7

| Sample | Treatment | Structure | Cells | Safranin-O Stain | Tide Mark Integrity | Total Mankin Score |
|---|---|---|---|---|---|---|
| 3592 RFC | Triamcinolone Acetonide 2mg/ml | 4.0 | 3.0 | 3.0 | 0.0 | 10.0 |
| 3591 RFC | Triamcinolone Acetonide 2mg/ml | 0.0 | 2.0 | 4.0 | 0.0 | 6.0 |
| 3594 RFC | Triamcinolone Acetonide 2mg/ml | 4.0 | 2.0 | 3.0 | 0.0 | 9.0 |
| MEAN | | 2.7 | 2.3 | 3.3 | 0.0 | 8.3 |
| SD | | 2.3 | 0.6 | 0.6 | 0.0 | 2.1 |
| 3592 LFC | 0.9% NaCl | 4.0 | 1.0 | 1.0 | 0.0 | 6.0 |
| 3591 LFC | 0.9% NaCl | 1.0 | 1.0 | 1.0 | 0.0 | 3.0 |
| 3594 LFC | 0.9% NaCl | 2.0 | 1.0 | 1.0 | 0.0 | 4.0 |

TABLE 139-continued

Mankin Score of Femoral Cartilage at 28 day evaluation, Group 7

| Sample | Treatment | Structure | Cells | Safranin-O Stain | Tide Mark Integrity | Total Mankin Score |
|---|---|---|---|---|---|---|
| MEAN | | 2.3 | 1.0 | 1.0 | 0.0 | 4.3 |
| SD | | 1.5 | 0.0 | 0.0 | 0.0 | 1.5 |

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

TABLE 13h

Mankin Score of Femoral Cartilage at 28 day evaluation, Group 8

| Sample | Treatment | Structure | Cells | Safranin-O Stain | Tide Mark Integrity | Total Mankin Score |
|---|---|---|---|---|---|---|
| 3588 RFC* | Triamcinolone Acetonide 8mg/ml | 4.0 | 3.0 | 3.0 | 0.0 | 10.0 |
| 3590 RFC | Triamcinolone Acetonide 8mg/ml | 5.0 | 3.0 | 4.0 | 0.0 | 12.0 |
| 3162 RFC | Triamcinolone Acetonide 8mg/ml | 1.0 | 1.0 | 4.0 | 0.0 | 6.0 |
| MEAN | | 3.0 | 2.0 | 4.0 | 0.0 | 9.0 |
| SD | | 2.8 | 1.4 | 0.0 | 0.0 | 4.2 |
| 3588 LFC* | 0.9% NaCl | 4.0 | 3.0 | 3.0 | 0.0 | 10.0 |
| 3590 LFC | 0.9% NaCl | 3.0 | 1.0 | 2.0 | 0.0 | 6.0 |
| 3162 LFC | 0.9% NaCl | 3.0 | 1.0 | 2.0 | 0.0 | 6.0 |
| MEAN | | 3.0 | 1.0 | 2.0 | 0.0 | 6.0 |
| SD | | 0.0 | 0.0 | 0.0 | 0.0 | 0.0 |

*Animal died prematurely. Data recorded but not included in averages.

MODIFIED MANKIN SCORING SYSTEM
STRUCTURE
Normal [0]
Surface Irregularities [1]
More Widespread Surface Irregularities [2]
Clefts to Transitional Zone [3]
Clefts to Radial Zone [4]
Clefts to Calcified Zone [5]
Complete Disorganization [6]
CELLS
Normal [0]
Mild Focal to Multifocal Hypocellularity [1]
Mild Focal to Multifocal Hypocellularity with Cloning [2]
Focally Extensive to Diffuse Hypocellularity [3]
SAFRANIN-O STAINING
Normal [0]
Slight Reduction [1]
Moderate Reduction [2]
Severe Reduction [3]
No Dye Noted [4]
TIDEMARK INTEGRITY
Intact [0]
Crossed By Blood Vessels [1]

In the cartilage at Day 28 there was no difference in the modified Mankin scores for HA-VS-PEG-(SH)$_2$ gel compared to its control. There was a mild increase in the loss of Safranin O staining intensity portion of the modified Mankin score for Groups 7 and 8 compared to either Groups 5 or 6. From Day 14 to Day 28 there was an increase in the modified Mankin scores of both Triamcinolone Acetonide-alone-treated groups (Groups 7 and 8). Such an increase in these scores over time is not observed for the HA-VS-PEG-(SH)$_2$ gel-treated Group 5 or the HA-VS-PEG-(SH)$_2$-TA gel treated Group 6.

The results of this study show there are no local or systemic effects at 28 days after intra-articular injection of 1.5 ml of the HA-VS-PEG-(SH)$_2$ alone or combined with 2 mg/ml of Triamcinolone Acetonide, HA-VS-PEG-(SH)$_2$-TA, into the knee joint of a goat. The effect on the cartilage of the addition of the triamcinolone acetonide to the HA-VS-PEG-(SH)$_2$ gel was less than the effect of injecting an equivalent dose or a higher dose of the triamcinolone acetonide alone.

The glycosaminoglycan specific staining with Safranin-O demonstrated that the effect of triamcinolone acetonide at 2 mg/mL (3 mg) when formulated in the HA-VS-PEG-(SH)$_2$ gel on the cartilage was lower than both the 2 mg/mL (3 mg) and 8 mg/mL (12 mg) bolus dose of triamcinolone acetonide at the 14 day and 28 day time points.

Figure 12:
FIG. 12 and FIG. 13 illustrate representative medial femoral condyle histology with Safranin-O staining (40×) at Day 14 (FIG. 12) and Day 28 (FIG. 13) post-injection, respectively, as described in detail in Example 34.
Figure 12:
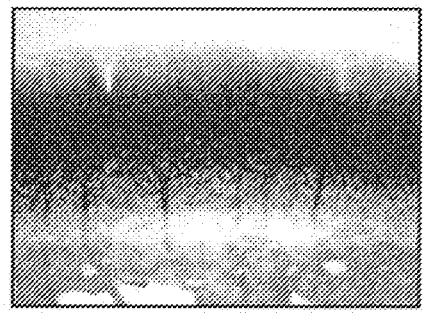
Figure 12:
Figure 12:
Figure 12:
Figure 12:
Figure 12:
Figure 12:
Figure 13:
Figure 13:
Figure 13:
Figure 13:
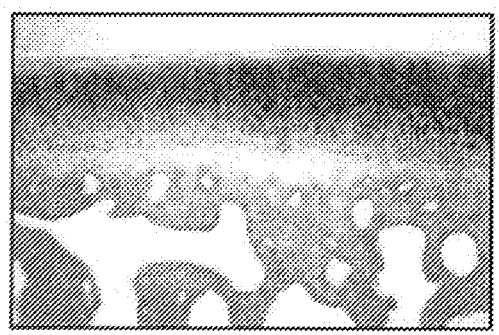
Figure 13:
Figure 13:
Figure 13:
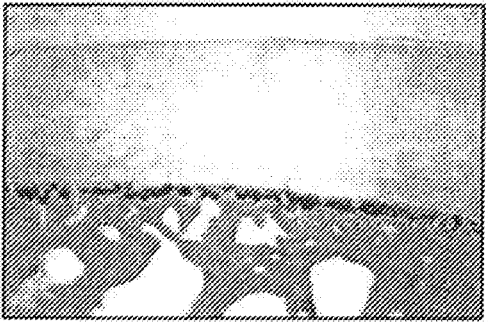
Figure 13:

FIGS. 12 and 13 illustrate representative medial femoral condyle histology with Safranin-O staining (40×) at Day 14 (FIG. 12) and Day 28 (FIG. 13) post-injection. The figures show that there is more safranin-O staining for the cartilage sample from the joints treated with the triamcinolone acetonide incorporated into the hydrogel than for the cartilage sample treated with an equivalent dose of triamcinolone acetonide that was injected directly into the joint (i.e. not incorporated into a hydrogel).

Example 35

Measurement of Extrusion Force

The force required to extrude the HA-VS/PEG-(SH)$_2$/HA product (Example 5, Example 41) and the HA-VS/PEG-(SH)$_2$/HA with triamcinilone acetonide (Example 38) was measured using a Chatillon motorized force tester (Chatillon LTCM-6 motorizedtester with a Chatillon DFE-025 digital force gauge, Ametec TCl Division). A fixture to hold a 10 mL syringe was attached to the base plate of the motorized tester such that the force gauge was directly over the plunger rod of the syringe. The force tester was turned on and the travel speed was set to 3 inches per minute by adjusting the rotary speed control dial to "3". The motorized tester arm was moved to its upper most point. The end-cap of the mL glass syringe that contained the formulation to be tested was removed and a 21 gauge needle was attached to he uncapped luer end tip. The syringe as placed in the syringe holder and the motorized tester arm was moved slowly downwards until the force gauge lightly touched the syringe plunger rod. A 16 mL test tube was placed under the end of the 21 gauge needle. The force gauge was set to record the maximum force. The force gauge was zeroed. The toggle switch of the motorized tested was then pressed such that the plunged of the syringe was depressed and the contents of the syringe were extruded through the 21 gauge needle. The motorized tester was stopped just prior to syringe stopper reaching the bottom of the syringe. The maximum extrusion force displayed on the force gauge screen was recorded. The results from the various formulations tested are shown below:

TABLE 14

| | Extrusion Force (lbs) | | |
|---|---|---|---|
| Sample # | HA-VS/PEG-(SH)$_2$ with HA (Lot NB30: 16) | HA-VS/PEG-(SH)$_2$ with HA (Lot M0229) | HA-VS/PEG-(SH)$_2$/TA with HA (Lot M0231) |
| 1 | 6.9 | 10.52 | 6.06 |
| 2 | 7.9 | 10.21 | 7.78 |
| 3 | 6.1 | 10.36 | 8.14 |
| 4 | 7.2 | | |
| 5 | 6.9 | | |
| 6 | 7.3 | | |
| Average | 7.1 | 10.36 | 7.33 |
| STD | 0.6 | 0.16 | 1.11 |

Example 36

Stability of Extrusion Force of HA-VS/PEG-(SH)$_2$ with HA Over Time

The force required to extrude the HA-VS/PEG-(SH)$_2$/HA product (example 5) as a function of time was measured using a Chatillon motorized force tester (Chatillon LTCM-6 motorized tester with a Chatillon DFE-025 digital force gauge, Ametec TCl Division). The extrusion force was measured after the product was made and then at 1 month and 3 months after that initial measurement. The samples were stored at room temperature over the 3 month time period. The extrusion force was measured for each sample as follows: A fixture to hold a 10 mL syringe was attached to the base plate of the motorized tester such that the force gauge was directly over the plunger rod of the syringe. The force tester was turned on and the travel speed was set to 3 inches per minute by adjusting the rotary speed control dial to "3". The motorized tester arm was moved to its upper most point. The end-cap of the 10 mL glass syringe that contained the formulation to be tested was removed and a 21 gauge needle was attached to he uncapped luer end tip. The syringe as placed in the syringe holder and the motorized tester arm was moved slowly downwards until the force gauge lightly touched the syringe plunger rod. A 16 mL test tube was placed under the end of the 21 gauge needle. The force gauge was set to record the maximum force. The force gauge was zeroed. The toggle switch of the motorized tested was then pressed such that the plunged of the syringe was depressed and the contents of the syringe were extruded through the 21 gauge needle. The motorized tester was stopped just prior to syringe stopper reaching the bottom of the syringe. The maximum extrusion force displayed on the force gauge screen was recorded. The results for Lot NB30:16 are shown below and show that there is no real change in the force required to extrude the product through a 21 gauge needle over 3 months.

TABLE 15

| | Extrusion Force (lbs) | | |
|---|---|---|---|
| Sample # | T = 0 | T = 1 month | T = 3 months |
| 1 | 10.31 | 6.87 | 9.46 |
| 2 | 8.7 | 7.62 | 7.14 |
| 3 | 8.72 | 10.55 | 11.57 |
| 4 | 9.47 | 7.53 | 7.36 |
| 5 | 10.43 | 8.25 | 7.65 |
| 6 | 9.63 | 8.3 | 8.95 |
| Average | 9.54 | 8.19 | 8.69 |
| STD | 0.75 | 1.27 | 1.69 |

Example 37

Preparation of HA-VS/PEG-(SH)$_2$/TA Gel with HA 170.8 mg, 341.3 mg, 511.7 mg, and 682.7 mg sterile triamcinolone acetonide were weighted out in 4 separate sterile 125 mL plastic bottles, which were labeled as TA 10 mg, TA 20 mg, TA 30 mg, and TA 40 mg, respectively. Each bottle containing the TA was tared on a balance and 14.98 g, 14.99 g, 14.99 g, and 15.01 g of sterile filtered (filtered though 0.2 um sterile filters, PVDF membrane) 14 mg/mL HA-VS in water were added to each of the 4 bottles in the order of TA 10 mg to 40 mg. TA powder and HA-VS solution were mixed by stirring until the resultant solutions appeared visually homogeneous. 0.375 mL of sterile filtered (through 0.2 um sterile filter) 1M Sodium Phosphate, pH 7.4, was added to each of the bottles, and the resultant mixtures were mixed well. 0.543 mL of 50 mg/mL of PEG-dithiol 3350 [PEG(SH)$_2$] (sterile filtered through 0.2 um sterile filter) was added to each container and mix thoroughly. The above steps were performed in a biohood. The mixtures were placed in a 37° C. oven overnight. The formulations were removed from the oven, the exterior of the containers were wiped down with 70/30 IPA/water and then transferred into a biohood. Each gel was broken up using a sterile spatula. 86.23 g, 86.25 g, 86.40 g, and 86.23 g of 7.83 mg/mL of HA in 0.9% saline (filtered though 0.2 um sterile filter, PVDF membrane) was added to the containers labeled TA 10 mg, 20 mg, 30 mg, and 40 mg, respectively. Each mixture was allowed to swell at room temperature for 3 hours. Each mixture was then passed through a 0.85 um mesh in a filter housing [A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved.]. The collected meshed mixture was then passed through a 0.85 um mesh for a second time. The collected mixture was then stored in a plastic container.

Example 38

Packaging of HA-VS/PEG-(SH)$_2$/TA Gel with HA 6 mL of each formulation from Example 37 was then aliquoted into a 10 mL glass syringe (BD Hypak glass syringe, P/N 47262119) that had a syringe cap. A plunger rod was screwed into the back of a sterile stopper (BD, P/N 47318319) after which the stopper/plunger was inserted into the neck of the syringe. The syringe was inverted and the syringe cap was opens slightly. The plunger was depressed until the excess air was expelled. The syringe cap was then tightened. The above steps were performed in a biohood. The process was repeated until all the product was packaged.

Example 39

Determining Particle Size

Deionized Water Wash

Stainless steel sieves of 2.36 mm (USA standard test sieve #8), 1.4 mm (USA standard test sieve #14), 1 mm (USA standard test sieve #18), 0.85 mm (USA standard test sieve #20), 0.6 mm (USA standard test sieve #30), 0.425 mm (USA standard test sieve #40), 0.25 mm (USA standard test sieve #60), and 0.150 mm (USA standard test sieve #100) were washed with DI water, and wiped dry using Kimwipes. After measuring the weight of each sieve, the sieves was placed on top of another going from the smallest size (#100) on the bottom to the largest size (#8) at the top. 100 mL of the HA-VS/PEG-(SH)$_2$/TA with HA formulation (Example 37) was slowly poured into the top sieve. Once most of the liquid component of the sample had passed through the top sieve, approx. 50 mL deionized water was slowly added to the top sieve to rinse the gel component that was retained by that sieve. Once the liquid component has passed trough the sieve, the sieve was removed from the stack. This process was repeated until each sieve had been washed and removed from the stack. Excess water droplets that remained on each sieve was wiped away using a paper towel. The total weight of each sieve (sieve plus collected gel) was measured. The weight of gel particles collected on each sieve was calculated by subtracting the initial sieve weight from the total sieve weight. The percentage gel collected by each sieve was calculated by taking the weight of gel collected on a particular sieve and then dividing by the total weight of the gel collected by all the sieves.

TABLE 16

| Sieve size # | Sieve size (mm) | Gel collected in each sieve (%) | | | |
|---|---|---|---|---|---|
| | | TA 10 | TA 20 | TA 30 | TA 40 |
| 8 | 2.36 | 0.1 | 0.3 | 0.5 | 0.0 |
| 14 | 1.40 | 11.4 | 14.7 | 19.4 | 7.6 |
| 18 | 1.00 | 44.9 | 48.0 | 34.2 | 35.2 |
| 20 | 0.85 | 29.4 | 23.1 | 22.0 | 28.0 |
| 30 | 0.60 | 7.4 | 7.8 | 14.7 | 14.7 |
| 40 | 0.425 | 3.7 | 2.7 | 4.4 | 7.8 |
| 60 | 0.25 | 1.5 | 1.7 | 2.9 | 4.2 |
| 100 | 0.15 | 1.7 | 1.7 | 2.0 | 2.6 |

Example 40

Determining Particle Size

Saline Wash

Stainless steel sieves of 2.36 mm (USA standard test sieve #8), 1.4 mm (USA standard test sieve #14), 1 mm (USA standard test sieve #18), 0.85 mm (USA standard test sieve #20), 0.6 mm (USA standard test sieve #30), 0.425 mm (USA standard test sieve #40), 0.25 mm (USA standard test sieve #60), and 0.150 mm (USA standard test sieve #100) were washed with DI water, and wiped dry using Kimwipes. After measuring the weight of each sieve, the sieves was placed on top of another going from the smallest size (#100) on the bottom to the largest size (#8) at the top. 100 mL of the HA-VS/PEG-(SH)$_2$/TA with HA (TA 10) formulation (Example 37) was slowly poured into the top sieve. Once most of the liquid component of the sample had passed through the top sieve, approx. 50 mL 0.9% saline was slowly added to the top sieve to rinse the gel component that was retained by that sieve. Once the liquid component has passed trough the sieve, the sieve was removed from the stack. This process was repeated until each sieve had been washed and removed from the stack. Excess saline droplets that remained on each sieve was wiped away using a paper towel. The total weight of each sieve (sieve plus collected gel) was measured. The weight of gel particles collected on each sieve was calculated by subtracting the initial sieve weight from the total sieve weight. The percentage gel collected by each sieve was calculated by taking the weight of gel collected on a particular sieve and then dividing by the total weight of the gel collected by all the sieves.

TABLE 17

| Sieve size # | Sieve size (mm) | Gel collected in each sieve (%) | | | | |
|---|---|---|---|---|---|---|
| | | Run-1 | Run-2 | Run-3 | Ave | SD |
| 8 | 2.36 | 0.0 | 0.4 | 0.7 | 0.4 | 0.3 |
| 14 | 1.40 | 9.0 | 3.4 | 10.5 | 7.6 | 3.8 |
| 18 | 1.00 | 50.6 | 50.1 | 48.8 | 49.9 | 0.9 |
| 20 | 0.85 | 20.5 | 23.2 | 18.6 | 20.8 | 2.3 |
| 30 | 0.60 | 10.9 | 12.8 | 10.9 | 11.6 | 1.1 |
| 40 | 0.425 | 4.8 | 5.2 | 5.7 | 5.3 | 0.4 |
| 60 | 0.25 | 2.7 | 3.5 | 3.1 | 3.1 | 0.4 |
| 100 | 0.15 | 1.3 | 1.1 | 1.7 | 1.4 | 0.3 |

Example 41

HA-VS/PEG-(SH)$_2$ Gel Slurry with Hyaluronic Acid

HA Swelling

Three of sterile 125 mL bottles were tared on a balance separately, and 14.97 g, 14.95 g, and 15.00 g of 14 mg/mL HA-VS in water (filtered through a 0.2 um sterile filter, PVDF membrane) were added to each of the three bottles. 0.375 mL of 1M Sodium Phosphate, pH 7.4 (sterile filtered through 0.2 um sterile filter) was added to each of the bottles, and mixed well. 0.543 mL of 50 mg/mL of PEG(SH)$_2$ (sterile filtered through 0.2 um sterile filter) was added to each container and mix thoroughly. The above steps were performed in a bio-hood. The mixtures were placed in a 37° C. oven overnight. The formulations were removed from the oven, the exterior of the containers were wiped down with 70/30 IPA/water and then transferred into a biohood. Each gel was broken up with a sterile spatula. Then 86.40 g, 86.21 g, and 86.31 g of 7.83 mg/mL of HA in 0.9% saline (filtered through a 0.2 um sterile filter, PVDF membrane) was added to the containers. The gels were swelled at room temperature for 3 hours. Each mixture was then passed through a 0.85 um mesh in a filter housing [A 23 mm diameter disc of a polyester mesh (McMaster Carr, Cat # 9218T13, Mesh Size: 20.3×20.3, Square/Rectangle Size: 0.0331", Micron Rating: 840 Microns, Percentage of Open Area: 46, Thread Diameter: 0.0157") was cut out using a 23 mm leather punch. The disc was inserted into a 25 mm syringe filter holder (Cole Palmer, Cat # EW-29550-42) and the filter holder was closed. The filter holder that contained the mesh was autoclaved.]. The collected meshed mixture was then passed through a 0.85 um mesh for a second time. The collected mixture was then stored in a plastic container.

Example 42

Packaging of HA-VS/PEG-(SH)$_2$ Gel Slurry with Hyaluronic Acid 6 mL of each formulation from Example 41 was then aliquoted into a 10 mL glass syringe (BD Hypak glass syringe, P/N 47262119) that had a syringe cap. A plunger rod was screwed into the back of a sterile stopper (BD, P/N 47318319) after which the stopper/plunger was inserted into the neck of the syringe. The syringe was inverted and the syringe cap was opens slightly. The plunger was depressed until the excess air was expelled. The syringe cap was then tightened. The above steps were performed in a biohood. The process was repeated until all the product was packaged.

Example 43

Determining Particle Size

Saline Wash

Stainless steel sieves of 2.36 mm (USA standard test sieve #8), 1.4 mm (USA standard test sieve #14), 1 mm (USA standard test sieve #18), 0.85 mm (USA standard test sieve #20), 0.6 mm (USA standard test sieve #30), 0.425 mm (USA standard test sieve #40), 0.25 mm (USA standard test sieve #60), and 0.150 mm (USA standard test sieve #100) were washed with DI water, and wiped dry using Kimwipes. After measuring the weight of each sieve, the sieves was placed on top of another going from the smallest size (#100) on the bottom to the largest size (#8) at the top. 100 mL of the HA-VS/PEG-(SH)$_2$ gel slurry with hyaluronic acid formulation (Example 41) was slowly poured into the top sieve. Once most of the liquid component of the sample had passed through the top sieve, approx. 50 mL 0.9% saline was slowly added to the top sieve to rinse the gel component that was retained by that sieve. Once the liquid component has passed trough the sieve, the sieve was removed from the stack. This process was repeated until each sieve had been washed and removed from the stack. Excess saline droplets that remained on each sieve was wiped away using a paper towel. The total weight of each sieve (sieve plus collected gel) was measured. The weight of gel particles collected on each sieve was calculated by subtracting the initial sieve weight from the total sieve weight. The percentage gel collected by each sieve was calculated by taking the weight of gel collected on a particular sieve and then dividing by the total weight of the gel collected by all the sieves.

TABLE 18

| Sieve Size # | Sieve size (mm) | Gel collected in each sieve (%) | | | | |
|---|---|---|---|---|---|---|
| | | Run-1 | Run-2 | Run-3 | Ave | SD |
| 8 | 2.36 | 2.2 | 2.5 | 2.0 | 2.3 | 0.3 |
| 14 | 1.40 | 9.7 | 9.8 | 9.2 | 9.6 | 0.3 |
| 18 | 1.00 | 33.2 | 29.1 | 27.2 | 29.8 | 3.1 |
| 20 | 0.85 | 25.4 | 22.1 | 24.9 | 24.1 | 1.8 |
| 30 | 0.60 | 14.4 | 19.1 | 19.1 | 17.5 | 2.7 |
| 40 | 0.425 | 10.0 | 8.5 | 10.3 | 9.6 | 1.0 |
| 60 | 0.25 | 3.4 | 5.7 | 5.1 | 4.7 | 1.2 |
| 100 | 0.15 | 1.8 | 3.1 | 2.3 | 2.4 | 0.7 |

Example 44

Sterility and Endotoxin Testing

The HA-VS/PEG-(SH)$_2$ gel with HA (Example 42, Example 5) and HA-VS/PEG-(SH)$_2$/TA gel with HA (Example 37, TA10) were tested for sterility and endotoxins by WuXi AppTec using protocol # BS210CBY.203 and BE215CBY.203 respectively. All the samples were sterile and had endotoxin levels of <0.5 EU/mL.

Example 45

In Vivo Biocompatibility Testing of HA-VS/PEG-(SH)$_2$ with HA

The following in-vivo study was undertaken to examine the in-vivo biocompatibility of the test material relative to a commercially available viscosupplement product in goats.

Materials used for study:

Test Material Hydros—HA-VS/PEG-(SH)$_2$ with HA [Lot NB51:119]

Control Material Synvisc—Commercially available viscosupplement product

A total of 6 skeletally mature female goats were used for this study. They were acquired from an approved USDA source. Animals weighed between 65 to 99 lbs at the start of the study. Goats were determined to be Caprine Arthritis Encephalitis (CAE) and Johne's negative prior to being placed in this study. Each animal was given a general health evaluation (subject to visual observation for attitude, ease in respiration, and freedom from diarrhea and nasal discharge) by a qualified veterinarian prior to being placed in the study. The animals were examined for any evidence of disease or lameness. Acceptability into the study was contingent on being disease free, clinically sound, and no history of prior use of the stifle joint. The goats were conditioned for an appropriate period of time as determined by the institution. Animal housing conditions conformed with applicable laws and regulations relating to laboratory animals, i.e., Animal Welfare Act, Public Law 89-544 as amended in Public Law 99-198, Federal Register 52:16, United States Department of Agriculture—Animal and Plant Inspection Service (USDA- APHIS), 1985 and Public Health Service Policy on Humane Care of Laboratory Animals, Office for Protection Against Research Risks/National Institutes of Health (OPRR/NIH), September, 1986. The goats were maintained in large indoor runs (pens) following injection. The goats had unrestricted activity at all times. All animals received approximately 2 lbs. of small ruminant diet per day as well as loose hay. Tap water was provided ad libitum. Feed was withheld approximately 12-24 hours prior to anesthesia and water was withheld approximately 12 hours prior to injections. A unique ear tag identified each animal.

Treatment

The study was designed as follows.

TABLE 19

Group and Treatment Assignment

| Group | Ear Tag | Right Stifle (1.5 ml) | Left Stifle (1.5 ml) | Sacrifice Time after R/L Injection |
|---|---|---|---|---|
| 1A | 3750 | Test Material Hydros Test Material | Control Material Synvisc | 24 ± 1 hours |
| 1A | 3751 | Test Material Hydros Test Material | Control Material Synvisc | 24 ± 1 hours |
| 1A | 3752 | Test Material Hydros Test Material | Control Material | 24 ± 1 hours |
| 1B | 3597 | Control Material Synvisc | Test Material Hydros Test Material | 24 ± 1 hours |
| 1B | 3753 | Control Material Synvisc | Test Material Hydros Test Material | 24 ± 1 hours |
| 1B | 3754 | Control Material Synvisc | Test Material Hydros Test Material | 24 ± 1 hours |
| Total | 6 | | | |

The basic injection procedure was identical for all subjects. All injections were performed under strict asepsis. The animals were anesthetized with an intravenous injection of Diazepam (0.1-0.5 mg/kg) and Ketamine (4.4-7.5 mg/kg) to effect. Each knee was physically examined for drawer, range of motion, swelling, temperature, crepitus, patella tracking, and valgus/varus abnormalities. All injections were conducted utilizing routine aseptic techniques. The left and right stifles were prepared for injection by clipping the areas, then cleansing them with chlorohexidine scrub. The animal was placed in dorsal recumbency. The right stifle was cleansed with chlorohexidine scrub alternating with 70% isopropyl alcohol three times and painted with iodine solution.

A standard technique was used to inject each stifle joint. A 2-inch by 21-gauge sized sterile needle was introduced into the intra-articular space via an anteromedial approach. The lateral intercondylar notch wall of the medial femoral condyle was felt and the needle backed slightly off. 1.5 ml of the Test Material was injected into the right joint for Group 1A or 1.5 ml of the Control Material for Group 1B. The injection needle was removed and pressure was maintained on the injection site. The injected stifle joint was then cycled 20-times through a full range of motion. Immediately following this, the left stifle joint was cleansed with chlorohexidine scrub alternating with 70% isopropyl alcohol three times and painted with iodine solution and 1.5 ml of the Control Material for Group 1A or 1.5 ml of the Test Material for Group 1B was injected into the left stifle joint in a similar manner as described above for the right stifle. The injection needle was removed and pressure maintained on the injection site. The injected stifle joint was then cycled 20-times through a full range of motion.

Post-injection checks were made for any animal displaying signs of distress and discomfort, and additional analgesics were given if needed. All treatments were recorded in the appropriate study documentation.

Animals were humanely sacrificed at 24±1 hours post initial injection with an intravenous injection consisting of Diazepam 0.22 mg/kg and Ketamine 10 mg/kg for induction of general anesthesia. Following this, the anesthetized animals were given an IV overdose of concentrated potassium chloride (KCl) until the cardiac arrest had been verified.

Analysis

Gross Morphological Observations

After collection of the knee joints, the joints were opened and gross evaluation as described in Table 20 of the injected stifle joints was done. Photodocumentation was performed. Degenerative joint changes were not evaluated.

TABLE 20

Gross Evaluation and Sample Collection

| Sample | Gross Evaluation | Sample collection | Photograph and/or Score |
|---|---|---|---|
| Synovial Fluid (left and right) | X | X | |
| Left and Right Knee joints | X | | X |
| Left and Right synovium | X | | X |

Additionally, semi-quantitative grading of the joint by a single observer as outline in Table 21 was performed.

TABLE 21

Gross Joint Evaluation Grading Scale

| Score | Coloration | Hyperemia | Edema |
|---|---|---|---|
| 0 | Normal | None | None |
| 1 | Slightly yellow | Slight | Slight |
| 2 | Yellow | Moderate | Moderate |
| 3 | | Marked | Marked |

The total joint gross evaluation score was the sum of the coloration, hyperemia, and edema scores (0-8 points).

Synovial Fluid Evaluation

After collection of the synovial fluid from the opened joints, the total volume was recorded. The fluid was grossly evaluated for viscosity, clarity and color and semi-quantitatively graded as per Table 22. With a hemocytometer, total white cell counts were done. Additionally, a synovial fluid smear was made for differential microscopic analysis. Remaining synovial fluid was preserved frozen in individually labeled cryovials at −80° C. A synovial fluid smear was retained for potential future analysis.

TABLE 22

Description and Score for Synovial Fluid

| Score | Color | Clarity | String |
|---|---|---|---|
| 0 | S = STRAW | C = CLEAR | N = NORMAL |
| 1 | P = PINK | H = HAZY | A = ABNORMAL |
| 2 | Y = YELLOW/R = RED | D = CLOUDY | W = WATERY |
| 3 | B = BLOODY | T = TURBID | |

Total synovial fluid score is the sum of the color, clarity and string scores (0-8 points).

Results

Figure 14:
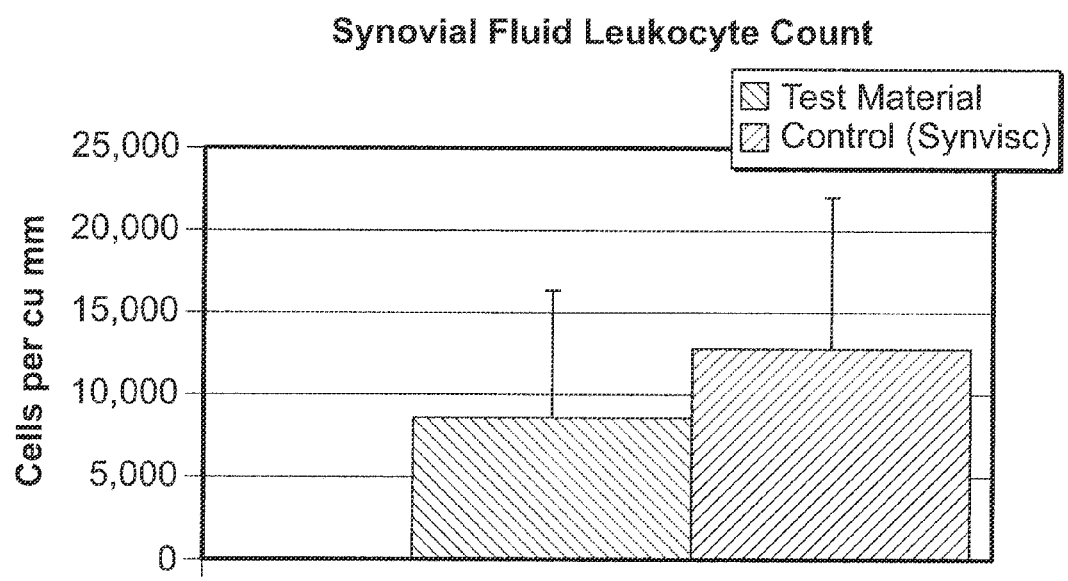
FIG. 14 provides a graphical representation of mean synovial fluid leukocyte count (mean±sd) for all animals relative to the Test Material and Control Material evaluated 24 hours after 1.5 ml intra-articular injection as described in detail in Example 45.

The tables below, along with FIG. 14, show that the HA-VS/PEG-(SH)$_2$ with HA is biocompatible in the joint at 24 hrs in the goat model.

TABLE 23

Synovial Fluid and Joint Gross Scores Evaluations
(Sorted relative to Test Material (TM) and Control Material)

| Ear Tag | Group | Test Article | Total Joint Score | Volume | color; clarity; string | Total Synovial Fluid Score | Grand Total Score |
|---|---|---|---|---|---|---|---|
| 3750 | 1A | TM | 0 | 1.6 | SHN | 1 | 1 |
| 3751 | 1A | TM | 0 | 1.4 | SHN | 1 | 1 |
| 3752 | 1A | TM | 0 | 1 | SHN | 1 | 1 |
| 3597 | 1B | TM | 0 | 1.1 | SHN | 1 | 1 |
| 3753 | 1B | TM | 0 | 0.75 | PHN | 2 | 2 |
| 3754 | 1B | TM | 0 | 0.45 | SHN | 1 | 1 |
| mean | | | 0.0 | 1.1 | | 1.2 | 1.2 |
| sd | | | 0.0 | 0.4 | | 0.4 | 0.4 |
| 3597 | 1B | Control | 0 | 2.2 | SHN | 1 | 1 |
| 3753 | 1B | Control | 0 | 1.9 | PHN | 2 | 2 |
| 3754 | 1B | Control | 0 | 1.5 | SHN | 1 | 1 |
| 3750 | 1A | Control | 0 | 1.3 | SHN | 1 | 1 |
| 3751 | 1A | Control | 0 | 0.8 | SHN | 1 | 1 |
| 3752 | 1A | Control | 1 | 1.85 | SHN | 1 | 2 |
| mean | | | 0.2 | 1.6 | | 1.2 | 1.3 |
| sd | | | 0.4 | 0.5 | | 0.4 | 0.5 |

Color: S = straw colored (0), Y = yellow (2), P = pink (1), R = red (2), B = bloody (3)
Clarity: C = clear (0), H = hazy (1), D = cloudy (2)
String (viscosity): N = normal (0), A = abnormal (1), W = watery (2)
TM = Test Material

TABLE 24

Synovial fluid cell differential and leukocyte (WBC) count

| | | | | Percent Cells in Synovial Fluid | | | | | | | | |
|---|---|---|---|---|---|---|---|---|---|---|---|---|
| Ear Tag | Group | Test Material | WBC/ mm$^3$ | % PMN | % Lymphocytes | % Monocytes | % Eosinophils | % Basophils | TM present | TM with surface cells | Macro/mono Phagocytosis of TM | Absolute WBC |
| 3750 | 1A | TM | 23,890 | 82 | 0 | 18 | 0 | 0 | + | + v few | + | 38,224,000 |
| 3751 | 1A | TM | 7,210 | 90 | 0 | 10 | 0 | 0 | + | + v few | + | 10,094,000 |
| 3752 | 1A | TM | 7,127 | 89 | 2 | 9 | 0 | 0 | + | + v few | + | 7,127,000 |
| 3597 | 1B | TM | 6,922 | 77 | 4 | 19 | 0 | 0 | + | + v few | + | 7,614,200 |
| 3753 | 1B | TM | 3,789 | 74 | 3 | 23 | 0 | 0 | + | + v few | + | 2,841,750 |
| 3754 | 1B | TM | 2,200 | 63 | 3 | 34 | 0 | 0 | + | + v few | + | 990,000 |
| mean | | | 8,523 | 79.2 | 2.0 | 18.8 | 0.0 | 0.0 | | | | 11,148,492 |
| sd | | | 7,807 | 10.1 | 1.7 | 9.2 | 0.0 | 0.0 | | | | 13,675,201 |
| 3750 | 1A | Control | 22,409 | 71 | 7 | 22 | 0 | 0 | + | + mod | + | 29,131,700 |
| 3751 | 1A | Control | 7,830 | 87 | 5 | 8 | 0 | 0 | + | + many | + | 6,264,000 |
| 3752 | 1A | Control | 26,700 | 72 | 2 | 26 | 0 | 0 | + | + many | + | 49,395,000 |
| 3597 | 1B | Control | 6,130 | 74 | 2 | 24 | 0 | 0 | + | + mod | + | 13,486,000 |
| 3753 | 18 | Control | 5,467 | 53 | 5 | 41 | 1 | 0 | + | + many | + | 10,387,300 |
| 3754 | 1B | Control | 8,100 | 53 | 2 | 45 | 0 | 0 | + | + many | + | 12,150,000 |
| mean | | | 12,773 | 68.3 | 3.8 | 27.7 | 0.2 | 0.0 | | | | 20,135,667 |
| sd | | | 9,280 | 13.2 | 2.1 | 13.5 | 0.4 | 0.0 | | | | 16,324,705 |

(Sorted relative to Test Material (TM) and Control Material)
PMN = polymorphonuclear leukocytes
WBC = White Blood Cells
TM = Test Material It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims. Any combination of the above-described elements in all possible variations thereof is encompassed by the invention unless otherwise indicated herein or otherwise clearly contradicted by context.

It is claimed:

1. A composition comprising crosslinked hydrogel particles in a solution of hyaluronic acid in saline, where the hydrogel particles are formed by reaction of polyethylene glycol dithiol (PEG-dithiol) with hyaluronic acid having 1-10% of its hydroxyl groups derivatized with 2-(vinylsulfonyl)ethoxy groups.

2. The composition of claim 1, wherein the crosslinked hydrogel particles are suspended in the solution of hyaluronic acid in saline.

3. The composition of claim 1, wherein the composition is sterile.

4. The composition of claim 1 packaged in a syringe.

5. The composition of claim 1 where the hydrogel particles further comprise a corticosteroid.

6. The composition of claim 1, wherein the hyaluronic acid having 1-10% of its hydroxyl groups derivatized with 2-(vinylsulfonyl)ethoxy possesses a molecular weight ranging from about 5000 to about 3 million daltons.

7. The composition of claim 1, wherein the PEG dithiol possesses a molecular weight ranging from about 250 to about 20,000 daltons.

8. The composition of claim 5, wherein the corticosteroid is triamcinolone acetonide.

9. The composition of claim 8, wherein the hydrogel particles comprise from about 0.1 to 1% percent by weight (wt/wt) triamcinolone acetonide.

10. The composition of claim 1, wherein the hydrogel particles have sizes ranging from about 0.10 to 3.0 millimeters.

11. The composition of claim 1, wherein the hydrogel particles possess a percent by weight (wt/wt) of polymer to water ranging from about 0.5 to 5.0 percent.

12. The composition of claim 1, extrudable through a 21 gauge needle.

13. The composition of claim 8, which when administered into an intra-articular space of a joint, has reduced undesirable side effects on the cartilage as compared to the intra-administration into an intra-articular space of a joint of an equivalent amount of triamcinolone acetonide absent of hydrogel incorporation, as indicated by a relatively lower degree of proteoglycan specific staining loss of the cartilage.

14. A method of administering a therapeutic composition, comprising administering the composition of claim 1 into an intra-articular space of a joint of a subject.

15. The method of claim 14, where the hydrogel particles of the composition of claim 1 further comprise triamcinolone acetonide.

16. A method for reducing one or more undesirable side effects on cartilage upon administration of triamcinolone acetonide into an intra-articular space of a joint of a subject suffering from osteoarthritis by incorporating the triamcinolone acetonide into a cross-linked hydrogel composition in accordance with claim 8.

17. A method for forming a composition in accordance with claim 1, comprising reacting a solution of hyaluronic acid having 1-10% of its hydroxyl groups derivatized with 2-(vinylsulfonyl)ethoxy groups with PEG dithiol under reaction conditions effective to form crosslinked hydrogel particles, and suspending the hydrogel particles in a saline solution of hyaluronic acid.

18. The method of claim 17, comprising:

reacting (i) a solution of hyaluronic acid having 1-10% of its hydroxyl groups derivatized with 2-(vinylsulfonyl) ethoxy groups, wherein the solution comprises particles of triamcinolone acetonide, with (ii) PEG dithiol, under reaction conditions effective to form crosslinked hydrogel particles comprising triamcinolone acetonide, and suspending the hydrogel particles in a saline solution of hyaluronic acid.

19. The method of claim 17, carried out under aseptic conditions in which all the solution components are sterile filtered prior to the reacting step to thereby form a sterile composition.

20. The method of claim 18, carried out under aseptic conditions in which all the solution components are sterile filtered prior to the reacting step, and wherein the triamcinolone acetonide is sterile, to thereby form a sterile composition.

\* \* \* \* \*